(12) United States Patent
Hedhammar et al.

(10) Patent No.: US 11,484,624 B2
(45) Date of Patent: Nov. 1, 2022

(54) SPIDER SILK COATING OF SOLID SURFACES

(71) Applicant: SPIBER TECHNOLOGIES AB, Stockholm (SE)

(72) Inventors: My Hedhammar, Stockholm (SE); Linnea Nilebäck, Täby (SE)

(73) Assignee: SPIBER TECHNOLOGIES AB, Stockholm (SE)

( * ) Notice: Subject to any disclaimer, the term of this patent is extended or adjusted under 35 U.S.C. 154(b) by 823 days.

(21) Appl. No.: 16/301,819

(22) PCT Filed: May 16, 2017

(86) PCT No.: PCT/EP2017/061712
§ 371 (c)(1),
(2) Date: Nov. 15, 2018

(87) PCT Pub. No.: WO2017/198655
PCT Pub. Date: Nov. 23, 2017

(65) Prior Publication Data
US 2019/0151505 A1 May 23, 2019

(30) Foreign Application Priority Data

May 16, 2016 (EP) .................................. 16169789
Oct. 5, 2016 (EP) .................................. 16192443

(51) Int. Cl.
| A61L 27/36 | (2006.01) |
| A61L 27/22 | (2006.01) |
| A61L 27/34 | (2006.01) |
| A61L 27/02 | (2006.01) |
| A61L 27/12 | (2006.01) |
| C12N 5/00  | (2006.01) |

(52) U.S. Cl.
CPC .......... *A61L 27/3604* (2013.01); *A61L 27/02* (2013.01); *A61L 27/12* (2013.01); *A61L 27/227* (2013.01); *A61L 27/34* (2013.01); *C12N 5/0018* (2013.01); *C12N 5/0068* (2013.01); *A61L 2400/12* (2013.01); *A61L 2420/02* (2013.01); *C12N 2533/50* (2013.01)

(58) Field of Classification Search
CPC .................................................. C12N 5/0068
See application file for complete search history.

(56) References Cited

U.S. PATENT DOCUMENTS

2011/0230911 A1    9/2011   Scheibel et al.

FOREIGN PATENT DOCUMENTS

| WO |    2007016524 A2 † | 2/2007 |         |
| WO | WO 2007/016524 A2  | 2/2007 |         |
| WO | WO 2007/078239 A2  | 7/2007 |         |
| WO | WO-2007078239 A2 * | 7/2007 | ....... C07K 14/43518 |
| WO | WO 2012/055854 A1  | 5/2012 |         |
| WO |    2015023798 A1 † | 2/2015 |         |
| WO |    2015134865 A1 † | 9/2015 |         |

OTHER PUBLICATIONS

Junghans et al., Appl. Phys. A 2006, 82:253-260.*
Wohlrab et al., J. Mater. Chem., 2012, 22:22050-22054.*
Jones et al., Biomacromolecules, 2015, 16:1418-1425.*
Hedhammar, M., et al. "Structural Properties of Recombinant Nonrepetitive and Repetitive Parts of Major Ampullate Spidroin 1 from Euprosthenops australis: Implications for Fiber Formation," Biochemistry, 2008, vol. 47, pp. 3407-3417.
Jansson, R., et al. "Recombinant Spider Silk Genetically Functionalized with Affinity Domains," Biomacromolecules, 2014, vol. 15, pp. 1696-1706.
Goodman et al., "The Future of Biologic Coatings for Orthopaedic Implants", Biomaterials, vol. 34, No. 13, Apr. 2013, pp. 3174-3183.
International Search Report (PCT/ISA/210) issued in PCT/EP2017/061712, dated Apr. 9, 2017.
Pouchkina-Stantcheva et al., "Molecular studies of a novel dragline silk from a nursery web spider, *Euprosthenops* sp. (Pisauridae)", ELSEVIER, Comparative Biochemistry and Physiology, Part B, vol. 138, 2004, pp. 371-376.
Vidal et al., "Enhanced cellular adhesion on titanium by silk functionalized with titanium binding and RGD peptides", Acta Biomaterialia, vol. 9, 2013, pp. 4935-4943.
Written Opinion (PCT/ISA/237) issued in PCT/EP2017/061712, dated Apr. 9, 2017.
Zeplin et al., "Spider Silk Coatings as a Bioshield to Reduce Periprosthetic Fibrous Capsule Formation", Advanced Functional Materials, vol. 24, 2014, pp. 2658-2666.
Eisoldt, et al. "Decoding the secrets of spider silk." Materials Today 14, No. 3 (2011): 80-86.†

(Continued)

*Primary Examiner* — Bin Shen
(74) *Attorney, Agent, or Firm* — Birch, Stewart, Kolasch & Birch, LLP

(57) ABSTRACT

A method for coating a solid surface with a recombinant spider silk protein capable of forming polymeric, solid structures is provided. The method is comprising the following steps: exposing the solid surface to an aqueous solution of the recombinant spider silk protein and thereby forming a surface layer of the recombinant spider silk protein adsorbed on the solid surface without formation of covalent bonds between the recombinant spider silk protein and the solid surface; and further exposing the surface layer of the solid surface to an aqueous solution of the recombinant spider silk protein and thereby forming an assembled silk structure layer of the recombinant spider silk protein on the surface layer; wherein the method does not include drying-in of spider silk protein.

10 Claims, 15 Drawing Sheets

Specification includes a Sequence Listing.

(56) References Cited

OTHER PUBLICATIONS

Rammensee, et al.. "Assembly mechanism of recombinant spider silk proteins." Proceedings of the National Academy of Sciences 105, No. 18 (2008): 6590-6595.†

Zeplin, et al. "Spider silk coatings as a bioshield to reduce periprosthetic fibrous capsule formation." Advanced Functional Materials 24, No. 18 (2014): 2658-2666.†

\* cited by examiner
† cited by third party

Fig 3
A
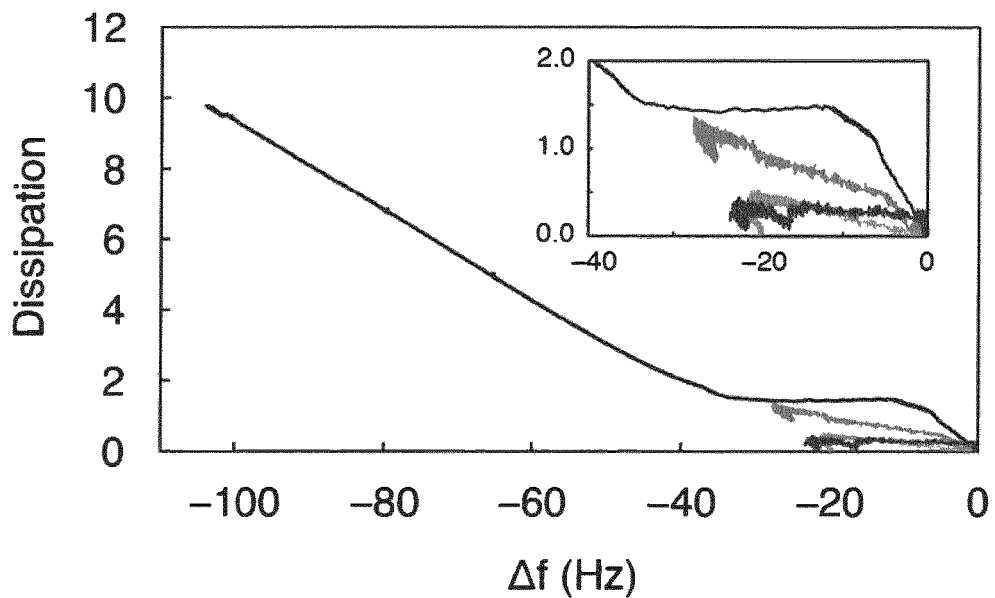
Viscoelastic propertes
B
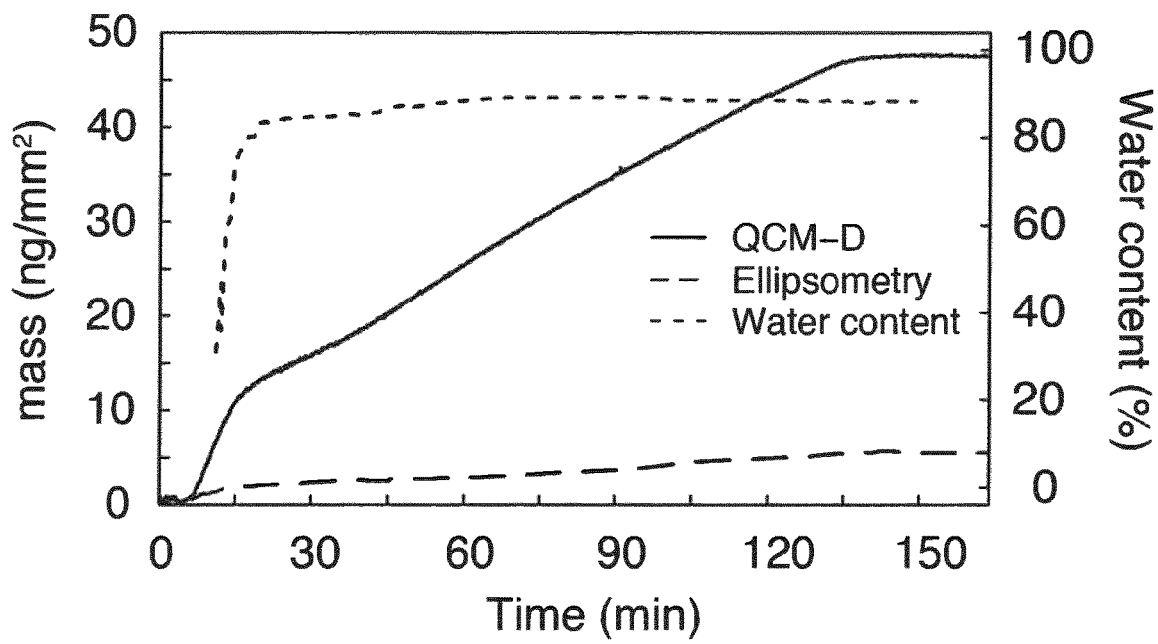
Adsorbed mass

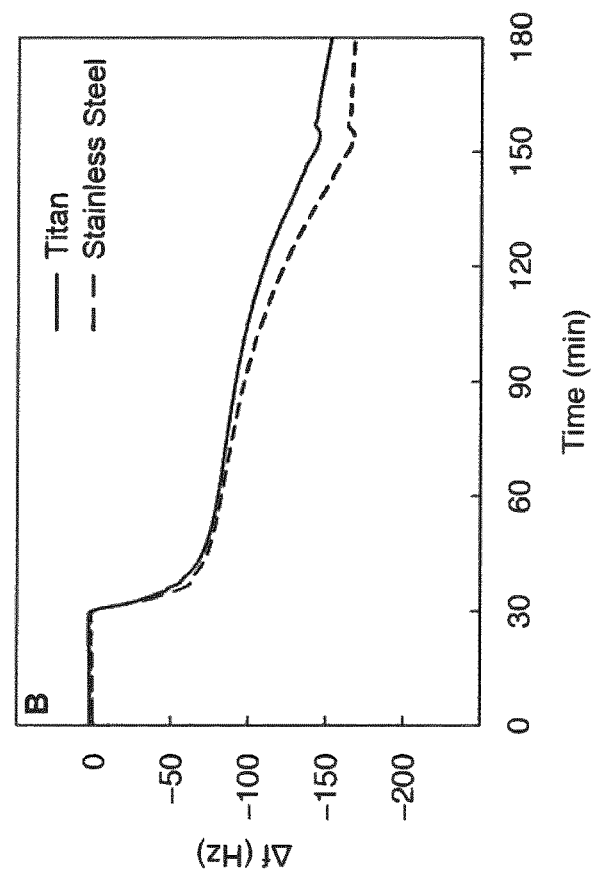
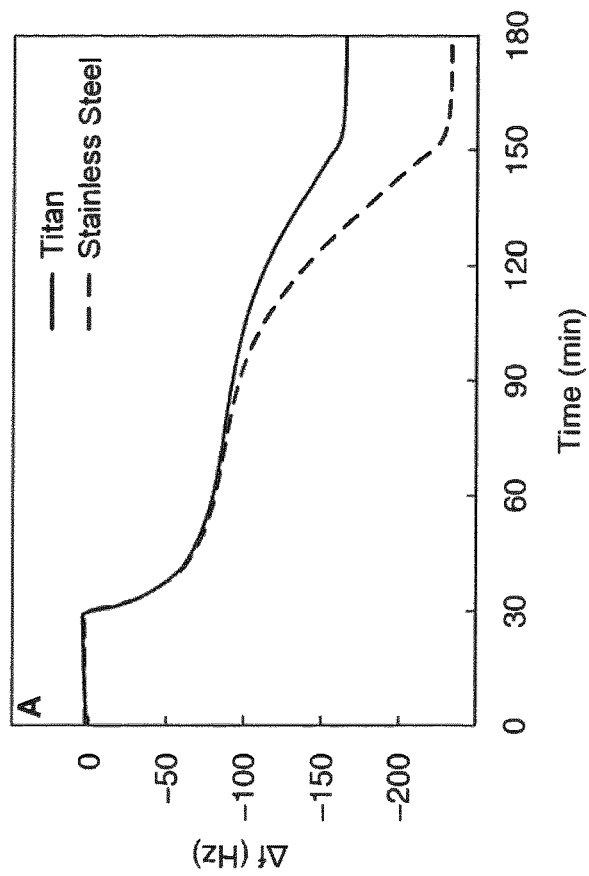
Fig 6

Fig 7
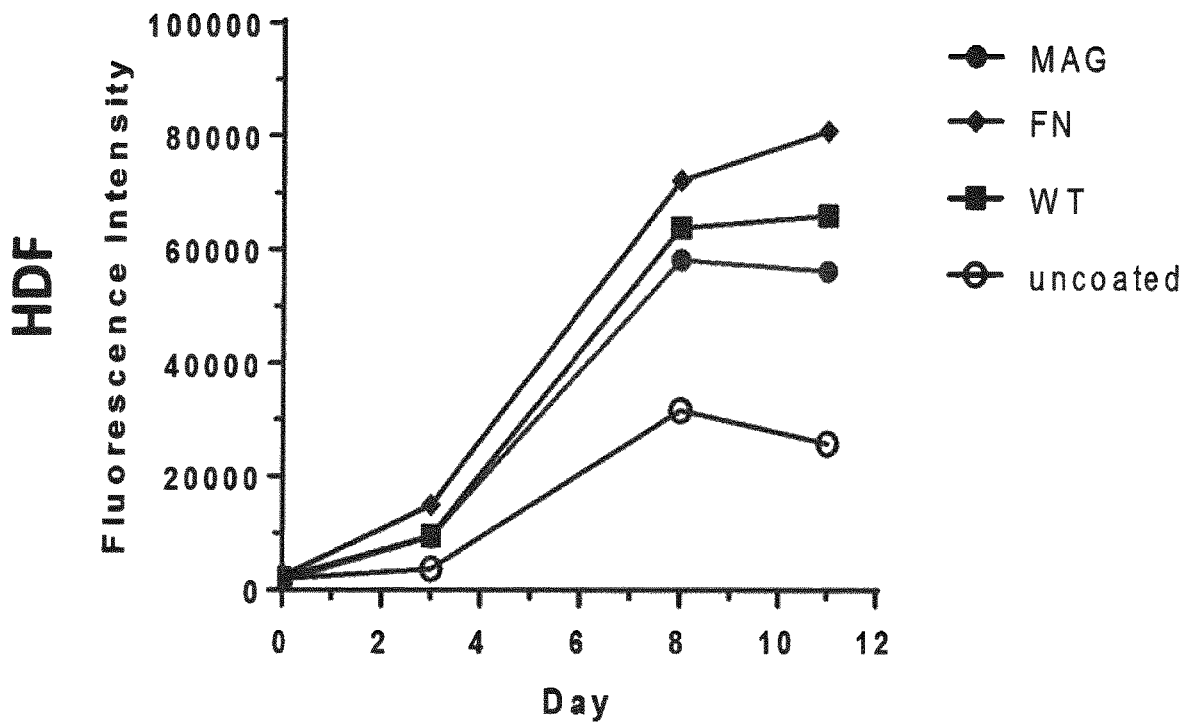
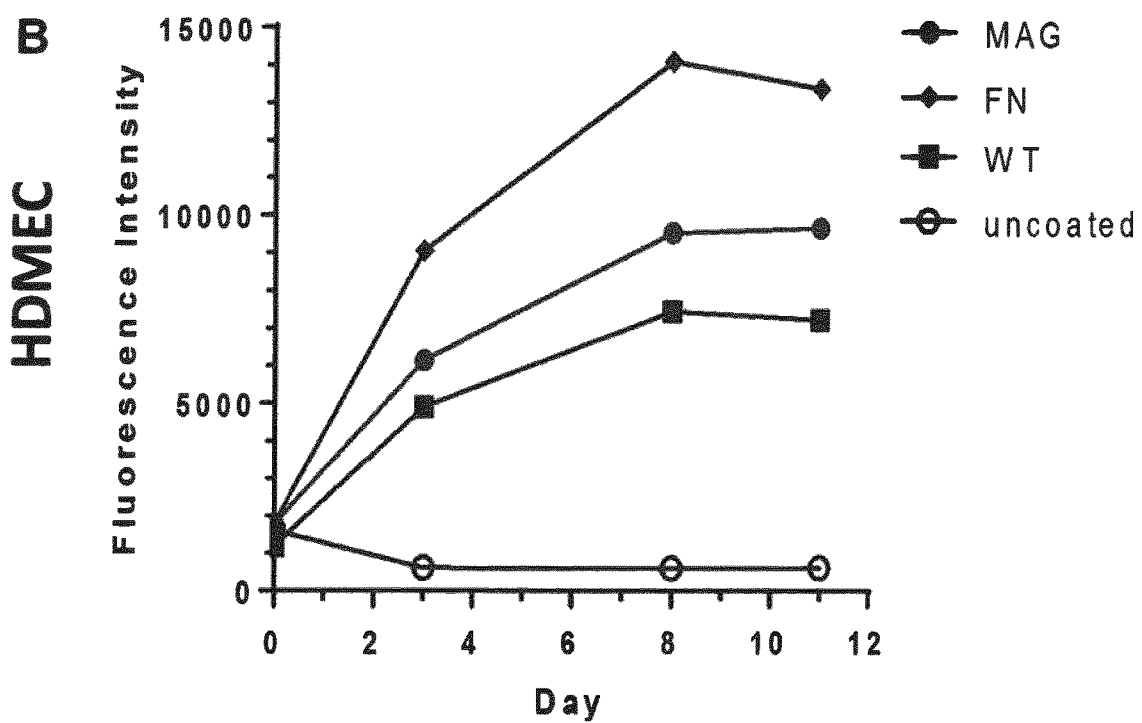

Fig 7, cont.
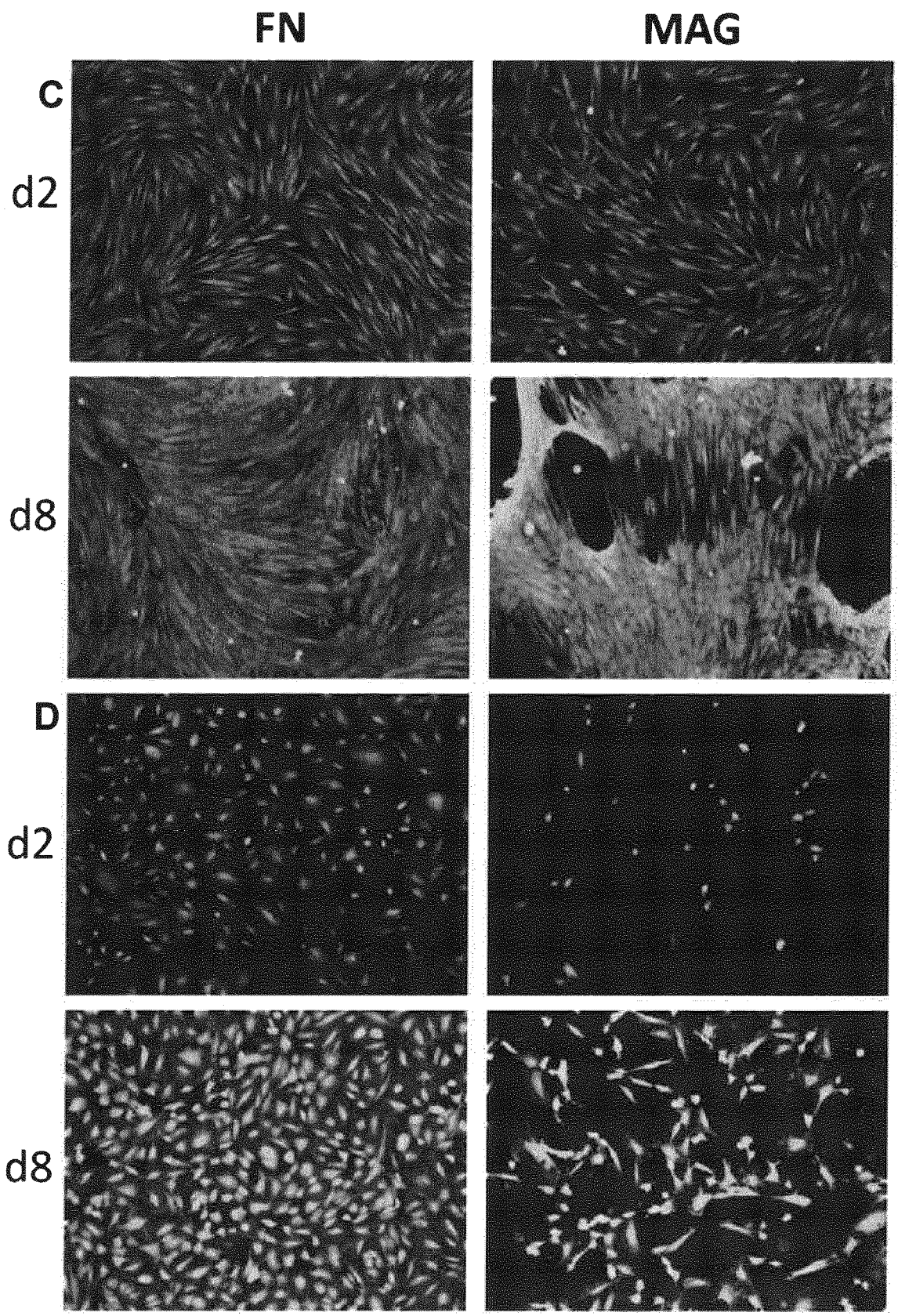

Fig 8
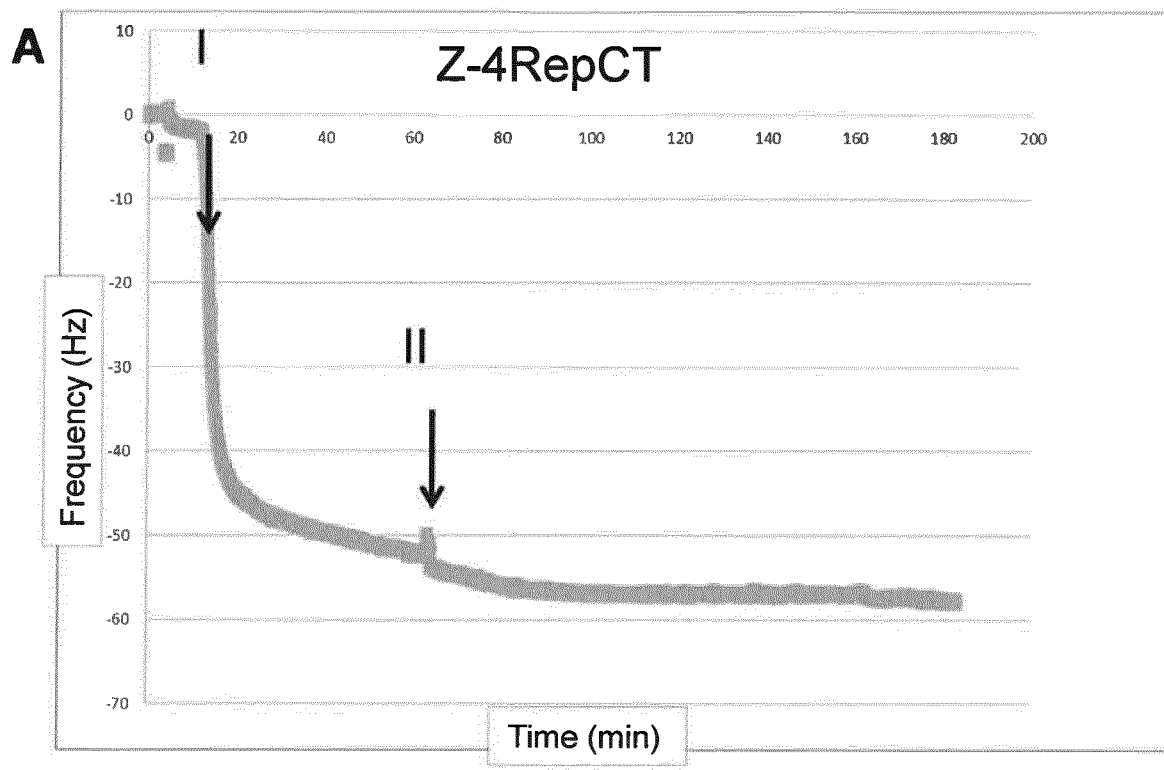
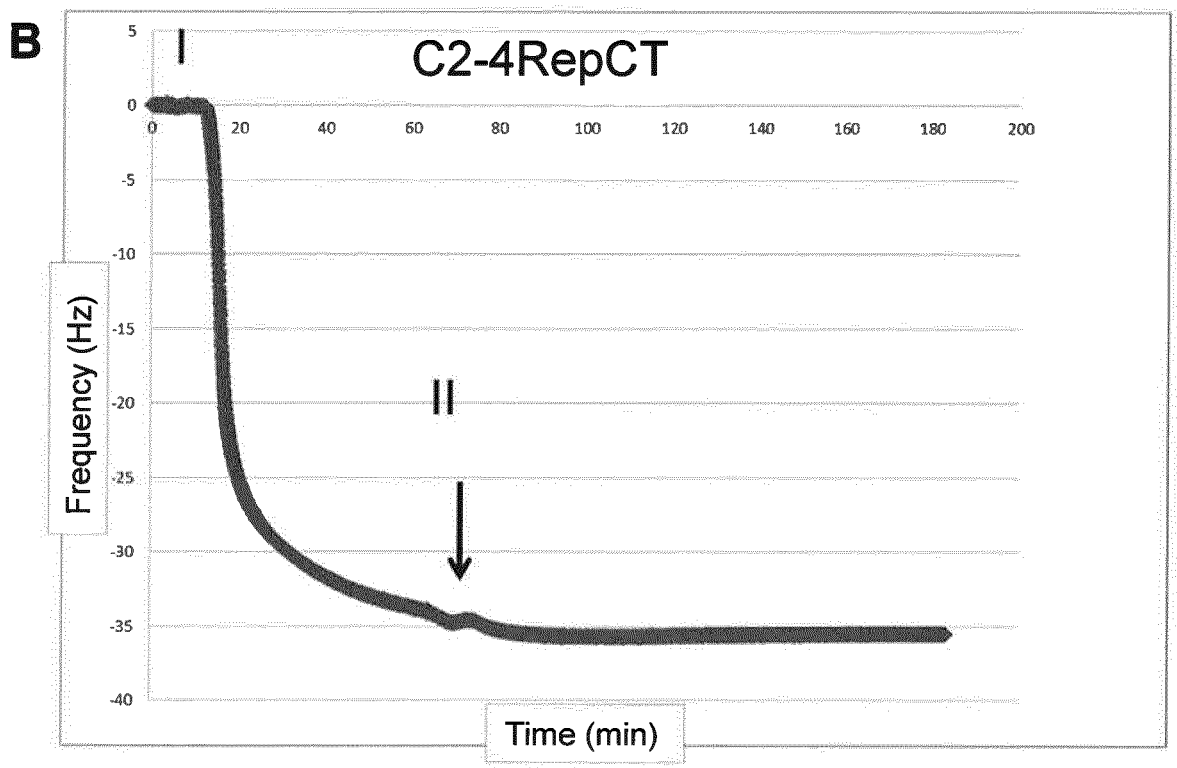

Fig 8, cont.
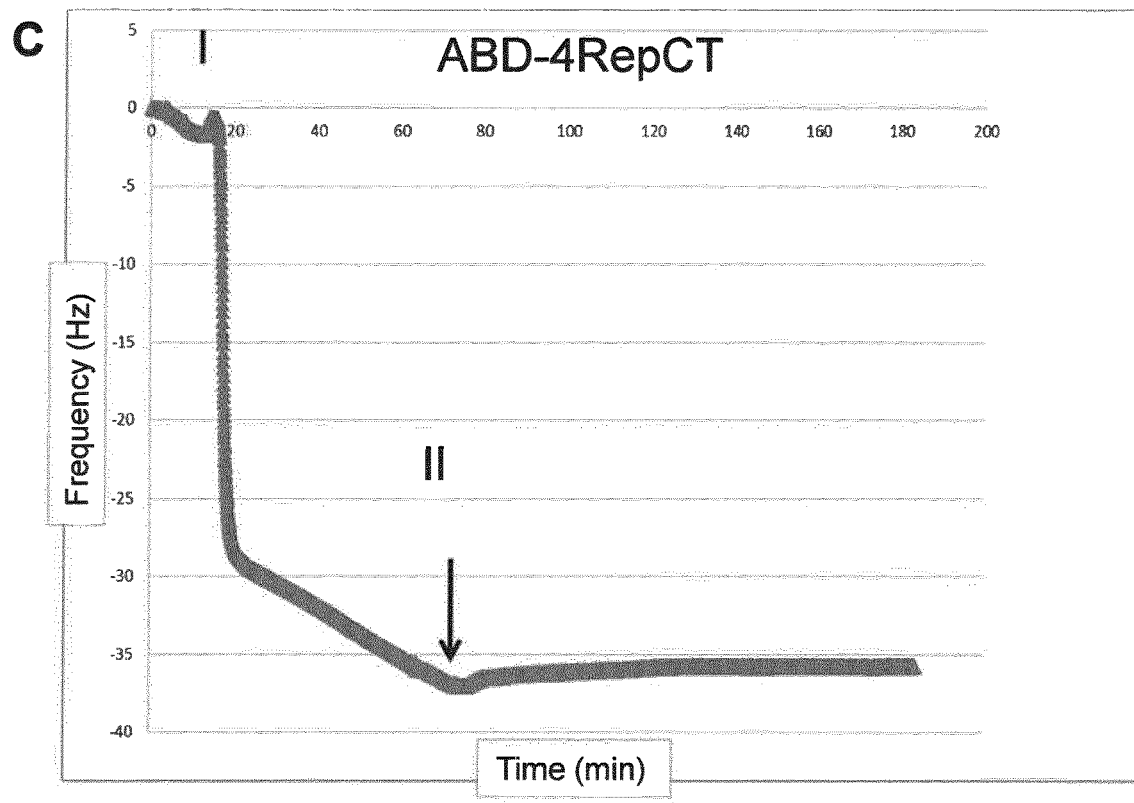
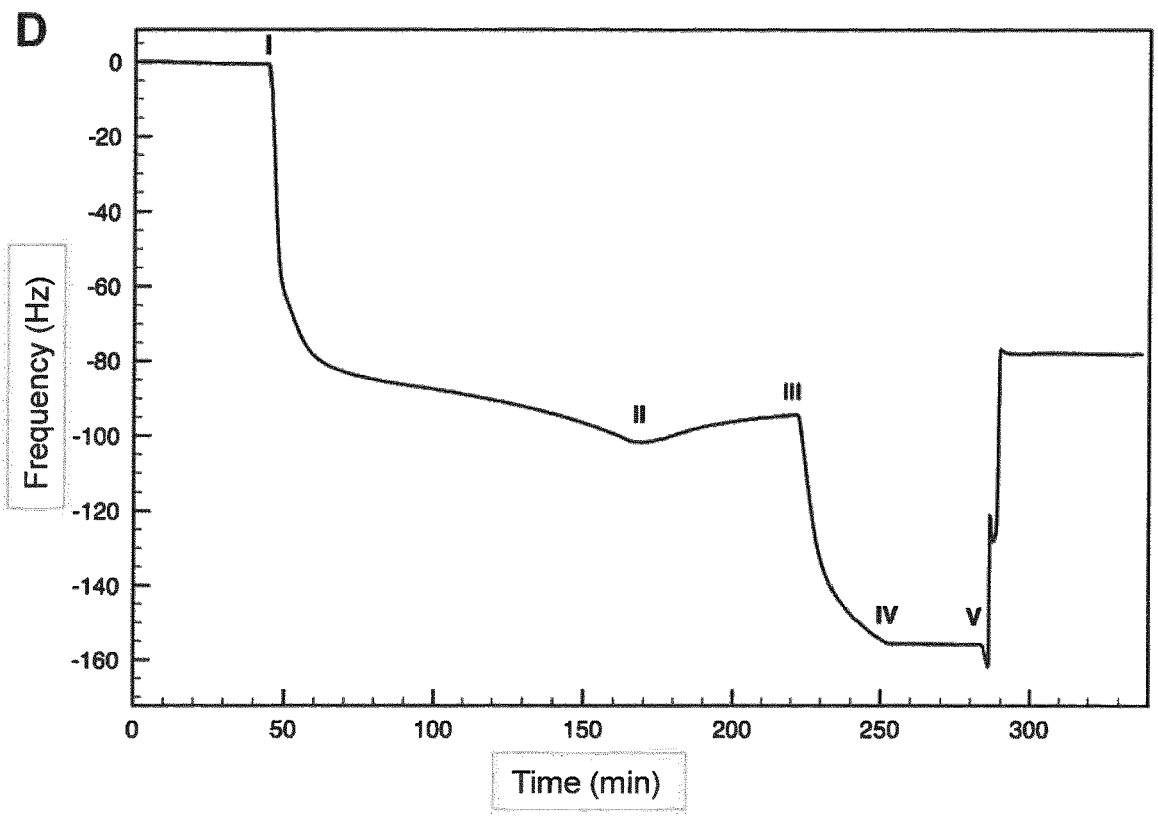

| | |
|---|---|
| CThyb_Esp | SRLSSPEASS RVSSAVSNLV SSG-PTNSAA LSSTISNVVS QIGASNPGLS |
| CTnat_Eau | SRLSSPSAVS RVSSAVSSLV SNG-QVNMAA LPNIISNISS SVSASAPGAS |
| AF350266_At1 | SRLSSPGAAS RVSSAVTSLV SSGGPTNSAA LSNTISNVVS QISSSNPGLS |
| AY666062_Cm1 | SHLSSPEASS RVSSAVSNLV SSG-STNSAA LPNTISNVVS QISSSNPGLS |
| AF350273_Lg1 | SALAAPATSA RISSHASTLL SNG-PTNPAS ISNVISNAVS QISSSNPGAS |
| AY953074_Lh1 | SALSAPATSA RISSHASALL SSG-PTNPAS ISNVISNAVS QISSSNPGAS |
| AY666068_Mh1 | SHLSSPEASS RVSSAVSNLV SGG-STNSAA LPNTISNVVS QISSSNPGLS |
| U20329_Nc1 | SRLSSPQASS RVSSAVSNLV ASG-PTNSAA LSSTISNVVS QIGASNPGLS |
| AY666076_Np1 | SRLSSPEASS RVSSAVSNLV SSG-PTNSAA LSNTISNVVS QISSSNPGLS |
| AF350277_Nm1 | SRLSSPQASS RVSSAVSNLV ASG-PTNSAA LSSTISNAVS QIGASNPGLS |
| AF350279_Ns1 | SRLSSPEASS RVSSAVSNLV SSG-PTNSAA LSSTISNVVS QIGASNPGLS |
| AY666057_Ov1 | SRLSSPEASS RVSSAVSNLV SSG-PTNSAA LSNTISNVVS QISSSNPGLS |
| AY666064_Ps1 | SRLSSPEASS RVSSAVSNLV SSG-PTNSAA LPNTISNVVS QISSSNPGLS |
| AF350285_Tk1 | SLLSSPASNA RISSAVSALA SGA-ASGPGY LSSVISNVVS QVSSNSGGLV |
| AF350286_Tv1 | SRLSSPASNA RISSAVSALA SGG-ASSPGY LSSIISNVVS QVSSNNDGLS |
| ABU20328_Ab2 | SRLSSSAASS RVSSAVSSLV SSG-PTTPAA LSNTISSAVS QISASNPGLS |
| AY365016_Aam2 | -RLSSPQASS RVSSAVSTLV SSG-PTNPAS LSNAIGSVVS QVSASNPGLP |
| AF350263_Aau2 | SRLSSPQASS RVSSAVSTLV SSG-PTNPAA LSNAISSVVS QVSASNPGLS |
| AF350267_At2 | SRLSSPQASS RVSSAVSTLV SSG-PTNPAS LSNAISSVVS QVSSSNPGLS |
| AF350272_Gm2 | SRLSSPQAGA RVSSAVSALV ASG-PTSPAA VSSAISNVAS QISASNPGLS |
| AF350275_Lg2 | SALSSPTTHA RISSHASTLL SSG-PTNSAA ISNVISNAVS QVSASNPGSS |
| AY953075_Lh2 | SALSSPTTHA RISSHASTLL SSG-PTNAAA LSNVISNAVS QVSASNPGSS |
| AY654293_Nc2 | SRLASPDSGA RVASAVSNLV SSG-PTSSAA LSSVISNAVS QIGASNPGLS |
| AF350278_Nm2 | SRLASPDSGA RVASAVSNLV SSG-PTSSAA LSSVISNAVS QIGASNPGLS |
| AF350280_Ns2 | SRLASPDSGA RVASAVSNLV SSG-PTSSAA LSSVIXNAVS QIGASNPGLS |
| AF350269_DtFb1 | SRLSSPEAAS RVSSAVSSLV SNG-QVNVDA LPSIISNLSS SISASATTAS |
| AF350270_DtFb2 | SRLSSPQAAS RVSSAVSSLV SNG-QVNVAA LPSIISSLSS SISASSTAAS |
| U47853_ADF1 | NRLSSAGAAS RVSSNVAAIA SAG----AAA LPNVISNIYS GVLSS--GVS |
| U47854_ADF2 | SRLSSPSAAA RVSSAVS-LV SNGGPTSPAA LSSSISNVVS QISASNPGLS |
| U47855_ADF3 | SRLSSPAASS RVSSAVSSLV SSG-PTKHAA LSNTISSVVS QVSASNPGLS |
| U47856_ADF4 | SVYLRLQPRL EVSSAVSSLV SSG-PTNGAA VSGALNSLVS QISASNPGLS |
| | |
| Consensus | SRLSSPQASS RVSSAVSNLV SSG-PTNSAA LSNTISNVVS QISASNPGLS |

Fig 10

```
CThyb_Esp       GCDVLVQALL EVVSALIHIL GSSSIGQVNY GSAGQATQLV GQSVYQALGE F
CTnat_Eau       GCEVIVQALL EVITALVQIV SSSSVGYINP SAVNQITNVV ANAMAQVMG- -
AF350266_At1    GCDVLVQALL EIVSALVHIL GSANIGQVNS SGVGRSASIV GQSINQAFS- -
AY666062_Cm1    GCDVLVQALL EVVSALIHIL GSSSIGQVNY GSAGQATQIV ---------- -
AF350273_Lg1    SCDVLVQALL ELVTALLTII GSSNVGNVNY DSSGQYAQVV SQSVQNAFV- -
AY953074_Lh1    ACDVLVQALL ELVTALLTII GSSNIGSVNY DSSGQYAQVV TQSVQNVFG- -
AY666068_Mh1    GCDVLVQALL EVVSALIHIL GSSSIGQVDY GSAGQATQIV GQSA------ -
U20329_Nc1      GCDVLIQALL EVVSALIQIL GSSSIGQVNY GSAGQATQIV GQSVYQALG- -
AY666076_Np1    GCDVLVQALL EVVSALIHIL GSSSIGQVNY GSAGQATQIV ---------- -
AF350277_Nm1    GCDVLIQALL EVVSALIHIL GSSSIGQVNY GSAGQATQ-- ---------- -
AF350279_Ns1    GCDVLIQALL EVVSALVHIL GSSSIGQVNY GSAGQATQ-- ---------- -
AY666057_Ov1    GCDVLVQALL EVVSAPIHIL GSSSIGQVNY GSAGQATQIV ---------- -
AY666064_Ps1    GCDVLVQALL EVVSALIHIL GSSSIGQVNY GSAGQATQIV ---------- -
AF350285_Tk1    GCDTLVQALL EAAAALVHVL ASSSGGQVNL NTAGYTSQL- ---------- -
AF350286_Tv1    GCDTVVQALL EVAAALVHVL ASSNIGQVNL NTAGYTSQL- ---------- -
ABU20328_Ab2    GCDVLVQALL EVVSALVHIL GSSSVGQINY GASAQYAQMV ---------- -
AY365016_Aam2   SCDVLVQALL EIVSALVHIL GSSSIGQINY SASSQYARLV GQSIAQALG- -
AF350263_Aau2   GCDVLVQALL ELVSALVHIL GSSSIGQINY AAS------- ---------- -
AF350267_At2    GCDVLVQALL EIVSALVHIL GSSSIGQINY AASSQYAQLV GQSLTQALG- -
AF350272_Gm2    GCDVLVQALL EIVSALVSIL SSASIGQINY GASGQYAAMI ---------- -
AF350275_Lg2    SCDVLVQALL ELITALISIV DSSNIGQVNY GSSGQYAQMV G--------- -
AY953075_Lh2    SCDVLVQALL EIITALISIL DSSSVGQVNY GSSGQYAQIV GQSMQQAMG- -
AY654293_Nc2    GCDVLIQALL EIVSACVTIL SSSSIGQVNY GAASQFAQVV GQSVLSAF-- -
AF350278_Nm2    GCDVLIQALL EIVSACVTIL SSSSIGQVNY GAA------- ---------- -
AF350280_Ns2    GCDVLIXALL EIVSACVTIL SSSSIGQVNY GAA------- ---------- -
AF350269_DtFb1  DCEVLVQVLL EVVSALVQIV CS-------- ---------- ---------- -
AF350270_DtFb2  DCEVLVQVLL EIVSALVQIV SSANVGYINP EASGSLN-AV GSALAAAMG- -
U47853_ADF1     SSEALIQALL EVISALIHVL GSASIGNVSS VGVNSALNAV QNAVGAYAG- -
U47854_ADF2     GCDILVQALL EIISALVHIL GSANIGPVNS SSAGQSASIV GQSVYRALS- -
U47855_ADF3     GCDVLVQALL EVVSALVSIL GSSSIGQINY GASAQYTQMV GQSVAQALA- -
U47856_ADF4     GCDALVQALL ELVSALVAIL SSASIGQVNV SSVSQSTQMI SQALS----- -

Consensus       GCDVLVQALL EVVSALVHIL GSSSIGQVNY GSAGQATQIV GQSVAQALGE F
```

Fig 10 (continued)

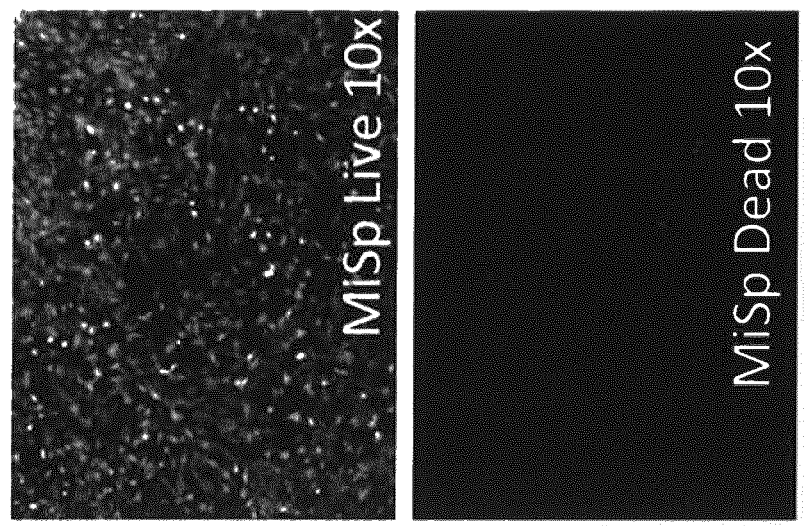
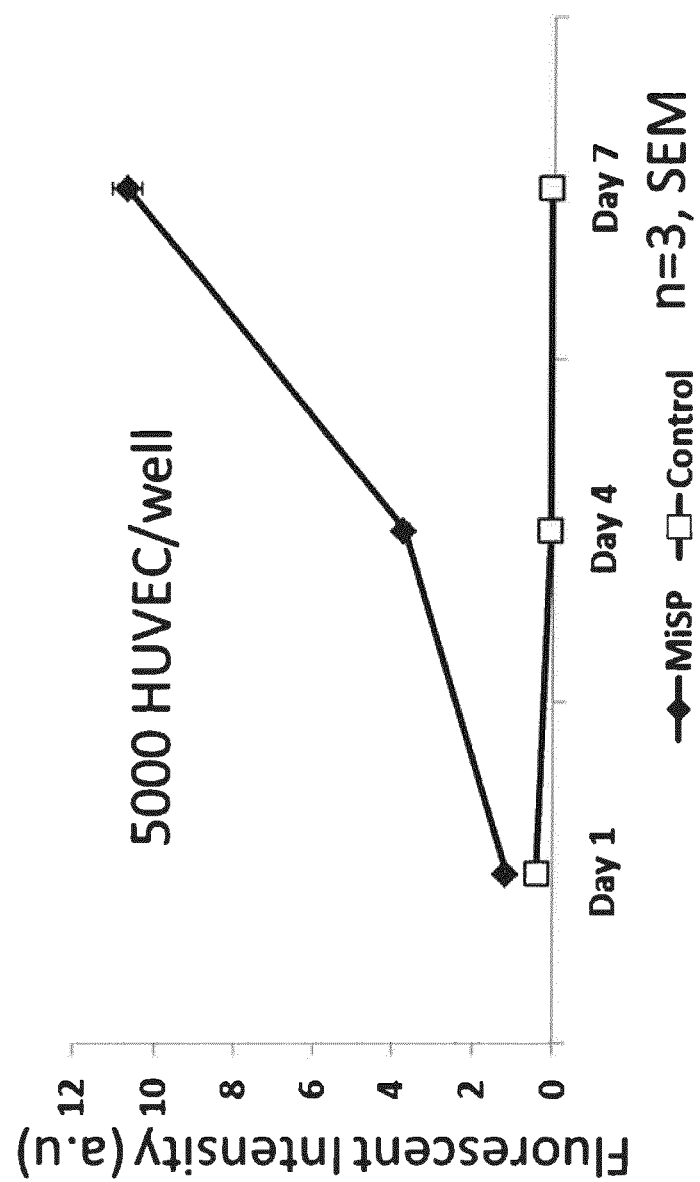
Fig 11

Fig 12
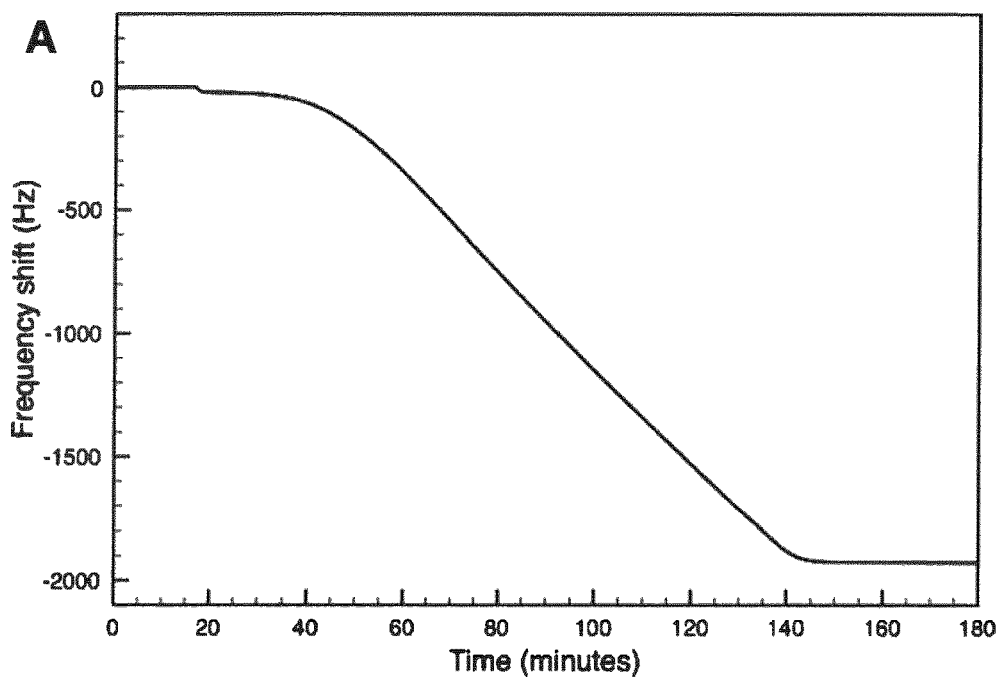
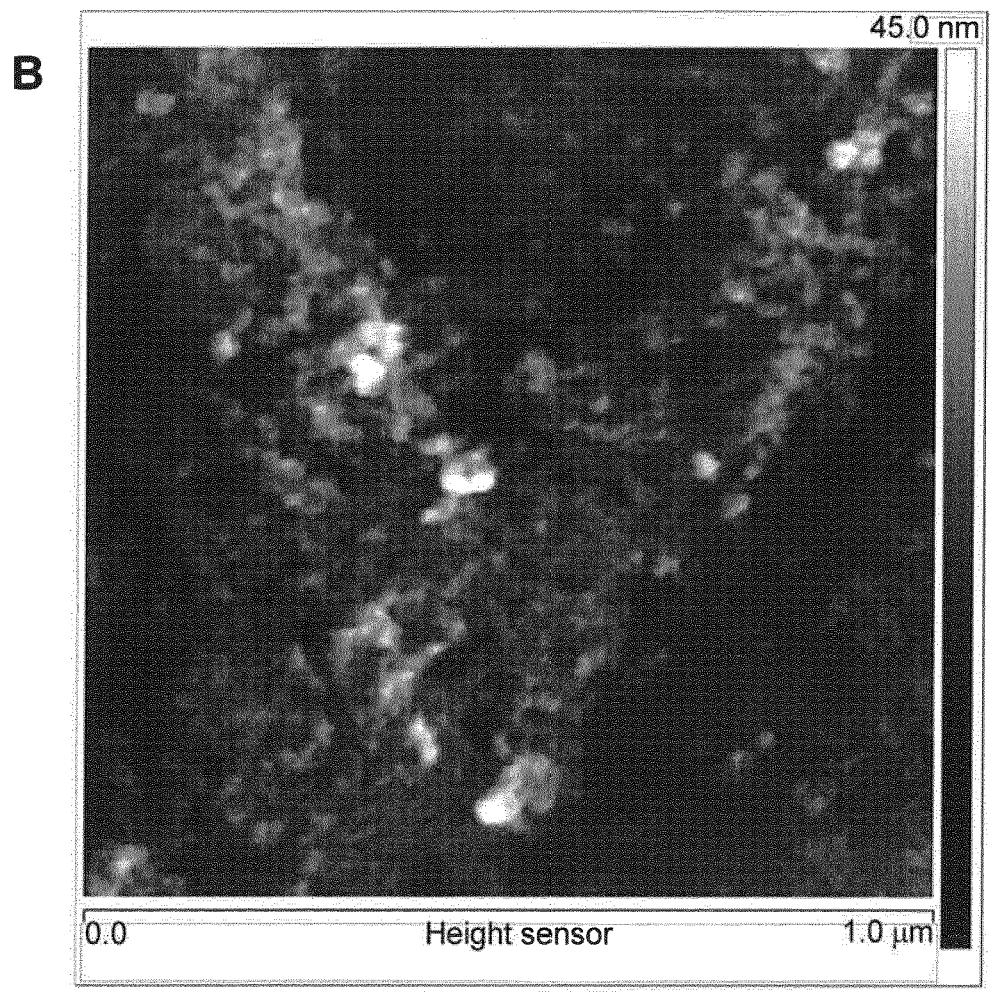

SEQUENCE LISTING

<160> NUMBER OF SEQ ID NOS: 72

<210> SEQ ID NO 1
<211> LENGTH: 789
<212> TYPE: DNA
<213> ORGANISM: Euprosthenops australis

<400> SEQUENCE: 1

```
ggtccgaatt caggtcaagg aggatatggt ggactaggtc aaggagggta tggacaaggt      60
gcaggaagtt ctgcagccgc tgccgccgcc gcagcagccg ccgcagcagg tggacaaggt     120
ggacaaggtc aaggaggata tggacaaggt tcaggaggtt ctgcagccgc cgccgccgcc     180
gcagcagcag cagcagctgc agcagctgga cgaggtcaag gaggatatgg ccaaggttct     240
ggaggtaatg ctgctgccgc agccgctgcc gccgccgccg ccgctgcagc agccggacag     300
ggaggtcaag gtggatatgg tagacaaagc caaggtgctg gttccgctgc tgctgctgct     360
gctgctgctg ccgctgctgc tgctgcagga tctggacaag gtggatacgg tggacaaggt     420
caaggaggtt atggtcagag tagtgcttct gcttcagctg ctgcgtcagc tgctagtact     480
gtagctaatt cggtgagtcg cctctcatcg ccttccgcag tatctcgagt tcttcagca     540 gtttctagct tggtttcaaa tggtcaagtg aatatggcag cgttacctaa tatcatttcc     600
aacatttctt cttctgtcag tgcatctgct cctggtgctt ctggatgtga ggtcatagtg     660
caagctctac tcgaagtcat cactgctctt gttcaaatcg ttagttcttc tagtgttgga     720
tatattaatc catctgctgt gaaccaaatt actaatgttg ttgctaatgc catggctcaa     780
gtaatgggc                                                             789
```

<210> SEQ ID NO 2
<211> LENGTH: 263
<212> TYPE: PRT
<213> ORGANISM: Euprosthenops australis
<220> FEATURE:
<221> NAME/KEY: DOMAIN
<222> LOCATION: (1)..(158)
<223> OTHER INFORMATION: REP fragment
<220> FEATURE:
<221> NAME/KEY: DOMAIN
<222> LOCATION: (159)..(165)
<223> OTHER INFORMATION: Spacer fragment
<220> FEATURE:
<221> NAME/KEY: DOMAIN
<222> LOCATION: (166)..(263)
<223> OTHER INFORMATION: CT fragment

<400> SEQUENCE: 2

```
Gly Pro Asn Ser Gly Gln Gly Gly Tyr Gly Gly Leu Gly Gln Gly Gly
1               5                  10                  15

Tyr Gly Gln Gly Ala Gly Ser Ser Ala Ala Ala Ala Ala Ala Ala Ala
            20                  25                  30

Ala Ala Ala Ala Gly Gly Gln Gly Gly Gln Gly Gln Gly Gly Tyr Gly
        35                  40                  45

Gln Gly Ser Gly Gly Ser Ala Ala Ala Ala Ala Ala Ala Ala Ala Ala
    50                  55                  60

Ala Ala Ala Ala Ala Gly Arg Gly Gln Gly Gly Tyr Gly Gln Gly Ser
65                  70                  75                  80

Gly Gly Asn Ala Ala Ala Ala Ala Ala Ala Ala Ala Ala Ala Ala Ala
                85                  90                  95

Ala Ala Gly Gln Gly Gly Gln Gly Gly Tyr Gly Arg Gln Ser Gln Gly
            100                 105                 110

Ala Gly Ser Ala Ala Ala Ala Ala Ala Ala Ala Ala Ala Ala Ala Ala
        115                 120                 125

Ala Gly Ser Gly Gln Gly Gly Tyr Gly Gly Gln Gly Gln Gly Gly Tyr
    130                 135                 140

Gly Gln Ser Ser Ala Ser Ala Ser Ala Ala Ala Ser Ala Ala Ser Thr
```

```
                145                 150                 155                 160
Val Ala Asn Ser Val Ser Arg Leu Ser Ser Pro Ser Ala Val Ser Arg
                165                 170                 175

Val Ser Ser Ala Val Ser Ser Leu Val Ser Asn Gly Gln Val Asn Met
            180                 185                 190

Ala Ala Leu Pro Asn Ile Ile Ser Asn Ile Ser Ser Val Ser Ala
        195                 200                 205

Ser Ala Pro Gly Ala Ser Gly Cys Glu Val Ile Val Gln Ala Leu Leu
        210                 215                 220

Glu Val Ile Thr Ala Leu Val Gln Ile Val Ser Ser Ser Val Gly
225                 230                 235                 240

Tyr Ile Asn Pro Ser Ala Val Asn Gln Ile Thr Asn Val Val Ala Asn
                245                 250                 255

Ala Met Ala Gln Val Met Gly
            260

<210> SEQ ID NO 3
<211> LENGTH: 98
<212> TYPE: PRT
<213> ORGANISM: Euprosthenops australis

<400> SEQUENCE: 3

Ser Arg Leu Ser Ser Pro Ser Ala Val Ser Arg Val Ser Ser Ala Val
1               5                   10                  15

Ser Ser Leu Val Ser Asn Gly Gln Val Asn Met Ala Ala Leu Pro Asn
            20                  25                  30

Ile Ile Ser Asn Ile Ser Ser Val Ser Ala Ser Pro Gly Ala
        35                  40                  45

Ser Gly Cys Glu Val Ile Val Gln Ala Leu Leu Glu Val Ile Thr Ala
    50                  55                  60

Leu Val Gln Ile Val Ser Ser Ser Val Gly Tyr Ile Asn Pro Ser
65                  70                  75                  80

Ala Val Asn Gln Ile Thr Asn Val Val Ala Asn Ala Met Ala Gln Val
                85                  90                  95

Met Gly

<210> SEQ ID NO 4
<211> LENGTH: 100
<212> TYPE: PRT
<213> ORGANISM: Artificial Sequence
<220> FEATURE:
<223> OTHER INFORMATION: Consensus sequence derived from known MaSp1 and
      MaSp2 proteins
<220> FEATURE:
<221> NAME/KEY: MISC_FEATURE
<222> LOCATION: (1)..(71)
<223> OTHER INFORMATION: Sequence length present in known species
      variants
<220> FEATURE:
<221> NAME/KEY: VARIANT
<222> LOCATION: (7)..(7)
<223> OTHER INFORMATION: Glu

<400> SEQUENCE: 4

Ser Arg Leu Ser Ser Pro Gln Ala Ser Ser Arg Val Ser Ser Ala Val
1               5                   10                  15

Ser Asn Leu Val Ser Gly Pro Thr Asn Ser Ala Ala Leu Ser Asn
            20                  25                  30

Thr Ile Ser Asn Val Val Ser Gln Ile Ser Ala Ser Asn Pro Gly Leu
        35                  40                  45
```

```
Ser Gly Cys Asp Val Leu Val Gln Ala Leu Leu Glu Val Val Ser Ala
        50                  55                  60

Leu Val His Ile Leu Gly Ser Ser Ser Ile Gly Gln Val Asn Tyr Gly
 65                  70                  75                  80

Ser Ala Gly Gln Ala Thr Gln Ile Val Gly Gln Ser Val Ala Gln Ala
                 85                  90                  95

Leu Gly Glu Phe
            100

<210> SEQ ID NO 5
<211> LENGTH: 1110
<212> TYPE: PRT
<213> ORGANISM: Euprosthenops australis
<220> FEATURE:
<221> NAME/KEY: REPEAT
<222> LOCATION: (7)..(19)
<220> FEATURE:
<221> NAME/KEY: REPEAT
<222> LOCATION: (20)..(42)
<220> FEATURE:
<221> NAME/KEY: REPEAT
<222> LOCATION: (43)..(56)
<220> FEATURE:
<221> NAME/KEY: REPEAT
<222> LOCATION: (57)..(70)
<220> FEATURE:
<221> NAME/KEY: REPEAT
<222> LOCATION: (71)..(83)
<220> FEATURE:
<221> NAME/KEY: REPEAT
<222> LOCATION: (84)..(106)
<220> FEATURE:
<221> NAME/KEY: REPEAT
<222> LOCATION: (107)..(120)
<220> FEATURE:
<221> NAME/KEY: REPEAT
<222> LOCATION: (121)..(134)
<220> FEATURE:
<221> NAME/KEY: REPEAT
<222> LOCATION: (135)..(147)
<220> FEATURE:
<221> NAME/KEY: REPEAT
<222> LOCATION: (148)..(170)
<220> FEATURE:
<221> NAME/KEY: REPEAT
<222> LOCATION: (171)..(183)
<220> FEATURE:
<221> NAME/KEY: REPEAT
<222> LOCATION: (184)..(197)
<220> FEATURE:
<221> NAME/KEY: REPEAT
<222> LOCATION: (198)..(211)
<220> FEATURE:
<221> NAME/KEY: REPEAT
<222> LOCATION: (212)..(234)
<220> FEATURE:
<221> NAME/KEY: REPEAT
<222> LOCATION: (235)..(248)
<220> FEATURE:
<221> NAME/KEY: REPEAT
<222> LOCATION: (249)..(265)
<220> FEATURE:
<221> NAME/KEY: REPEAT
<222> LOCATION: (266)..(279)
<220> FEATURE:
<221> NAME/KEY: REPEAT
<222> LOCATION: (280)..(293)
<220> FEATURE:
<221> NAME/KEY: REPEAT
<222> LOCATION: (294)..(306)
<220> FEATURE:
<221> NAME/KEY: REPEAT
<222> LOCATION: (307)..(329)
<220> FEATURE:
```

```
<221> NAME/KEY: REPEAT
<222> LOCATION: (330)..(342)
<220> FEATURE:
<221> NAME/KEY: REPEAT
<222> LOCATION: (343)..(356)
<220> FEATURE:
<221> NAME/KEY: REPEAT
<222> LOCATION: (357)..(370)
<220> FEATURE:
<221> NAME/KEY: REPEAT
<222> LOCATION: (371)..(393)
<220> FEATURE:
<221> NAME/KEY: REPEAT
<222> LOCATION: (394)..(406)
<220> FEATURE:
<221> NAME/KEY: REPEAT
<222> LOCATION: (407)..(420)
<220> FEATURE:
<221> NAME/KEY: REPEAT
<222> LOCATION: (421)..(434)
<220> FEATURE:
<221> NAME/KEY: REPEAT
<222> LOCATION: (435)..(457)
<220> FEATURE:
<221> NAME/KEY: REPEAT
<222> LOCATION: (458)..(470)
<220> FEATURE:
<221> NAME/KEY: REPEAT
<222> LOCATION: (471)..(488)
<220> FEATURE:
<221> NAME/KEY: REPEAT
<222> LOCATION: (489)..(502)
<220> FEATURE:
<221> NAME/KEY: REPEAT
<222> LOCATION: (503)..(516)
<220> FEATURE:
<221> NAME/KEY: REPEAT
<222> LOCATION: (517)..(529)
<220> FEATURE:
<221> NAME/KEY: REPEAT
<222> LOCATION: (530)..(552)
<220> FEATURE:
<221> NAME/KEY: REPEAT
<222> LOCATION: (553)..(566)
<220> FEATURE:
<221> NAME/KEY: REPEAT
<222> LOCATION: (567)..(580)
<220> FEATURE:
<221> NAME/KEY: REPEAT
<222> LOCATION: (581)..(594)
<220> FEATURE:
<221> NAME/KEY: REPEAT
<222> LOCATION: (595)..(617)
<220> FEATURE:
<221> NAME/KEY: REPEAT
<222> LOCATION: (618)..(630)
<220> FEATURE:
<221> NAME/KEY: REPEAT
<222> LOCATION: (631)..(647)
<220> FEATURE:
<221> NAME/KEY: REPEAT
<222> LOCATION: (648)..(661)
<220> FEATURE:
<221> NAME/KEY: REPEAT
<222> LOCATION: (662)..(675)
<220> FEATURE:
<221> NAME/KEY: REPEAT
<222> LOCATION: (676)..(688)
<220> FEATURE:
<221> NAME/KEY: REPEAT
<222> LOCATION: (689)..(711)
<220> FEATURE:
<221> NAME/KEY: REPEAT
<222> LOCATION: (712)..(725)
<220> FEATURE:
<221> NAME/KEY: REPEAT
<222> LOCATION: (726)..(739)
<220> FEATURE:
<221> NAME/KEY: REPEAT
```

```
<222> LOCATION: (740)..(752)
<220> FEATURE:
<221> NAME/KEY: REPEAT
<222> LOCATION: (753)..(775)
<220> FEATURE:
<221> NAME/KEY: REPEAT
<222> LOCATION: (776)..(789)
<220> FEATURE:
<221> NAME/KEY: REPEAT
<222> LOCATION: (790)..(803)
<220> FEATURE:
<221> NAME/KEY: REPEAT
<222> LOCATION: (804)..(816)
<220> FEATURE:
<221> NAME/KEY: REPEAT
<222> LOCATION: (817)..(839)
<220> FEATURE:
<221> NAME/KEY: REPEAT
<222> LOCATION: (840)..(853)
<220> FEATURE:
<221> NAME/KEY: REPEAT
<222> LOCATION: (854)..(867)
<220> FEATURE:
<221> NAME/KEY: REPEAT
<222> LOCATION: (868)..(880)
<220> FEATURE:
<221> NAME/KEY: REPEAT
<222> LOCATION: (881)..(903)
<220> FEATURE:
<221> NAME/KEY: REPEAT
<222> LOCATION: (904)..(917)
<220> FEATURE:
<221> NAME/KEY: REPEAT
<222> LOCATION: (918)..(931)
<220> FEATURE:
<221> NAME/KEY: REPEAT
<222> LOCATION: (932)..(945)
<220> FEATURE:
<221> NAME/KEY: REPEAT
<222> LOCATION: (946)..(968)
<220> FEATURE:
<221> NAME/KEY: REPEAT
<222> LOCATION: (969)..(981)
<220> FEATURE:
<221> NAME/KEY: REPEAT
<222> LOCATION: (982)..(998)
<220> FEATURE:
<221> NAME/KEY: REPEAT
<222> LOCATION: (999)..(1013)
<220> FEATURE:
<221> NAME/KEY: REPEAT
<222> LOCATION: (1014)..(1027)
<220> FEATURE:
<221> NAME/KEY: REPEAT
<222> LOCATION: (1028)..(1042)
<220> FEATURE:
<221> NAME/KEY: REPEAT
<222> LOCATION: (1043)..(1059)
<220> FEATURE:
<221> NAME/KEY: REPEAT
<222> LOCATION: (1060)..(1073)
<220> FEATURE:
<221> NAME/KEY: REPEAT
<222> LOCATION: (1074)..(1092)

<400> SEQUENCE: 5

Gln Gly Ala Gly Gly Asn Ala Ala Ala Ala Ala Ala Ala Ala
  1               5                  10                  15

Ala Ala Ala Gly Gln Gly Gly Gln Gly Gly Tyr Gly Gly Leu Gly Gln
                 20                  25                  30

Gly Gly Tyr Gly Gln Gly Ala Gly Ser Ser Ala Ala Ala Ala Ala
            35                  40                  45

Ala Ala Ala Ala Ala Ala Ala Ala Gly Arg Gly Gln Gly Gly Tyr Gly
        50                  55                  60
```

```
Gln Gly Ser Gly Gly Asn Ala Ala Ala Ala Ala Ala Ala Ala
 65                  70                  75                  80

Ala Ala Ser Gly Gln Gly Gly Gln Gly Gly Gln Gly Gly Gln
                 85                  90                  95

Gly Gly Tyr Gly Gln Gly Ala Gly Ser Ser Ala Ala Ala Ala Ala
                100                 105                 110

Ala Ala Ala Ala Ala Ala Ala Gly Gln Gly Gln Gly Arg Tyr Gly
            115                 120                 125

Gln Gly Ala Gly Gly Asn Ala Ala Ala Ala Ala Ala Ala Ala
    130                 135                 140

Ala Ala Ala Gly Gln Gly Gly Gln Gly Gly Gln Gly Leu Gly Gln
145                 150                 155                 160

Gly Gly Tyr Gly Gln Gly Ala Gly Ser Ser Ala Ala Ala Ala Ala
                165                 170                 175

Ser Ala Ala Ala Ala Ala Ala Gly Arg Gly Gln Gly Gly Tyr Gly Gln
            180                 185                 190

Gly Ala Gly Gly Asn Ala Ala Ala Ala Ala Ala Ala Ala Ala
            195                 200                 205

Ala Ala Ala Gly Gln Gly Gly Gln Gly Gly Tyr Gly Gly Leu Gly Gln
    210                 215                 220

Gly Gly Tyr Gly Gln Gly Ala Gly Ser Ser Ala Ala Ala Ala Ala
225                 230                 235                 240

Ala Ala Ala Ala Ala Ala Gly Gly Gln Gly Gln Gly Gln Gly Gly
                245                 250                 255

Arg Tyr Gly Gln Gly Ala Gly Ser Ser Ala Ala Ala Ala Ala Ala
            260                 265                 270

Ala Ala Ala Ala Ala Ala Gly Gln Gly Gln Gly Tyr Gly Gln
            275                 280                 285

Gly Ala Gly Gly Asn Ala Ala Ala Ala Ala Ala Ala Ala Ala
    290                 295                 300

Ala Ala Gly Gln Gly Gly Gln Gly Gly Gln Gly Leu Gly Gln Gly
305                 310                 315                 320

Gly Tyr Gly Gln Gly Ala Gly Ser Ser Ala Ala Ala Ala Ala Ala
                325                 330                 335

Ala Ala Ala Ala Ala Ala Gly Arg Gly Gln Gly Gly Tyr Gly Gln Gly
            340                 345                 350

Ala Gly Gly Asn Ala Ala Ala Ala Ala Ala Ala Glu Ala Ala
        355                 360                 365

Ala Ala Gly Gln Gly Gly Gln Gly Gly Tyr Gly Gly Leu Gly Gln Gly
    370                 375                 380

Gly Tyr Gly Gln Gly Ala Gly Ser Ser Ala Ala Ala Ala Ala Ala
385                 390                 395                 400

Ala Ala Ala Ala Ala Ala Gly Arg Gly Gln Gly Gly Tyr Gly Gln Gly
            405                 410                 415

Ala Gly Gly Asn Ala Ala Ala Ala Ala Ala Ala Ala Ala Ala
        420                 425                 430

Ala Ala Gly Gln Gly Gly Gln Gly Gly Tyr Gly Gly Leu Gly Gln Gly
    435                 440                 445

Gly Tyr Gly Gln Gly Ala Gly Ser Ser Ala Ala Ala Ala Ala Ala
    450                 455                 460

Ala Ala Ala Ala Ala Ala Gly Gly Gln Gly Gln Gly Gln Gly Arg
465                 470                 475                 480

Tyr Gly Gln Gly Ala Gly Ser Ser Ala Ala Ala Ala Ala Ala Ala
```

```
                   485                 490                 495
Ala Ala Ala Ala Ala Gly Arg Gly Gln Gly Gly Tyr Gly Gln Gly
                500                 505                 510

Ser Gly Gly Asn Ala Ala Ala Ala Ala Ala Ala Ala Ala Ala Ala
            515                 520                 525

Ser Gly Gln Gly Ser Gln Gly Gly Gln Gly Gln Gly Gly Gly Gly
        530                 535                 540

Tyr Gly Gln Gly Ala Gly Ser Ser Ala Ala Ala Ala Ala Ala Ala
545                 550                 555                 560

Ala Ala Ala Ala Ala Ser Gly Arg Gly Gln Gly Gly Tyr Gly Gln Gly
                565                 570                 575

Ala Gly Gly Asn Ala Ala Ala Ala Ala Ala Ala Ala Ala Ala Ala
            580                 585                 590

Ala Ala Gly Gln Gly Gly Gln Gly Gly Tyr Gly Gly Leu Gly Gln Gly
            595                 600                 605

Gly Tyr Gly Gln Gly Ala Gly Ser Ser Ala Ala Ala Ala Ala Ala
        610                 615                 620

Ala Ala Ala Ala Ala Gly Gly Gln Gly Gln Gly Gln Gly Gln Gly Tyr
625                 630                 635                 640

Gly Gln Gly Ala Gly Ser Ser Ala Ala Ala Ala Ala Ala Ala Ala
                645                 650                 655

Ala Ala Ala Ala Ala Gly Arg Gly Gln Gly Gly Tyr Gly Gln Gly Ser
                660                 665                 670

Gly Gly Asn Ala Ala Ala Ala Ala Ala Ala Ala Ala Ala Ala Ser
        675                 680                 685

Gly Gln Gly Gly Gln Gly Gly Gln Gly Gly Gln Gly Gly Gly Tyr
    690                 695                 700

Gly Gln Gly Ala Gly Ser Ser Ala Ala Ala Ala Ala Ala Ala Ala
705                 710                 715                 720

Ala Ala Ala Ala Ala Gly Gln Gly Gln Gly Gly Tyr Gly Gln Gly Ala
                725                 730                 735

Gly Gly Asn Ala Ala Ala Ala Ala Ala Ala Ala Ala Ala Ala Ala
            740                 745                 750

Gly Gln Gly Gly Gln Gly Gly Gln Gly Gly Leu Gly Gln Gly Gly Tyr
        755                 760                 765

Gly Gln Gly Ala Gly Ser Ser Ala Ala Ala Ala Ala Ala Ala Ala
    770                 775                 780

Ala Ala Ala Ala Ala Gly Arg Gly Gln Gly Gly Tyr Gly Gln Gly Val
785                 790                 795                 800

Gly Gly Asn Ala Ala Ala Ala Ala Ala Ala Ala Ala Ala Ala Ala
            805                 810                 815

Gly Gln Gly Gly Gln Gly Gly Gln Gly Gly Leu Gly Gln Gly Gly Tyr
        820                 825                 830

Gly Gln Gly Ala Gly Ser Ser Ala Ala Ala Ala Ala Ala Ala Ala
    835                 840                 845

Ala Ala Ala Ala Ala Gly Arg Gly Gln Gly Gly Tyr Gly Gln Gly Ser
850                 855                 860

Gly Gly Asn Ala Ala Ala Ala Ala Ala Ala Ala Ala Ala Ala Ser
865                 870                 875                 880

Gly Gln Gly Ser Gln Gly Gly Gln Gly Gly Gln Gly Gly Gly Tyr
        885                 890                 895

Gly Gln Gly Ala Gly Ser Ser Ala Ala Ala Ala Ala Ala Ala Ala
    900                 905                 910
```

-continued

```
Ala Ala Ala Ala Ser Gly Arg Gly Gln Gly Gly Tyr Gly Gln Gly Ala
        915                 920                 925

Gly Gly Asn Ala Ala Ala Ala Ala Ala Ala Ala Ala Ala Ala Ala
    930                 935                 940

Ala Gly Gln Gly Gln Gly Gly Tyr Gly Gly Leu Gly Gln Gly Gly
945                 950                 955                 960

Tyr Gly Gln Gly Ala Gly Ser Ser Ala Ala Ala Ala Ala Ala Ala
                965                 970                 975

Ala Ala Ala Ala Gly Gly Gln Gly Gly Gln Gly Gln Gly Gly Tyr Gly
            980                 985                 990

Gln Gly Ser Gly Gly Ser Ala Ala Ala Ala Ala Ala Ala Ala Ala Ala
        995                 1000                1005

Ala Ala Ala Ala Ala Gly Arg Gly Gln Gly Gly Tyr Gly Gln Gly
    1010                1015                1020

Ser Gly Gly Asn Ala Ala Ala Ala Ala Ala Ala Ala Ala Ala Ala
    1025                1030                1035

Ala Ala Ala Ala Gly Gln Gly Gly Gln Gly Gly Tyr Gly Arg Gln
    1040                1045                1050

Ser Gln Gly Ala Gly Ser Ala Ala Ala Ala Ala Ala Ala Ala Ala
    1055                1060                1065

Ala Ala Ala Ala Ala Gly Ser Gly Gln Gly Gly Tyr Gly Gly Gln
    1070                1075                1080

Gly Gln Gly Gly Tyr Gly Gln Ser Ser Ala Ser Ala Ser Ala Ala
    1085                1090                1095

Ala Ser Ala Ala Ser Thr Val Ala Asn Ser Val Ser
    1100                1105                1110

<210> SEQ ID NO 6
<211> LENGTH: 23
<212> TYPE: PRT
<213> ORGANISM: Artificial Sequence
<220> FEATURE:
<223> OTHER INFORMATION: Consensus sequence derived from internal
      repeats of Euprosthenops australis MaSp1
<220> FEATURE:
<221> NAME/KEY: VARIANT
<222> LOCATION: (4)..(4)
<223> OTHER INFORMATION: Ser
<220> FEATURE:
<221> NAME/KEY: VARIANT
<222> LOCATION: (8)..(8)
<223> OTHER INFORMATION: Tyr
<220> FEATURE:
<221> NAME/KEY: VARIANT
<222> LOCATION: (11)..(11)
<223> OTHER INFORMATION: Gln

<400> SEQUENCE: 6

Gly Gln Gly Gly Gln Gly Gly Gln Gly Gly Leu Gly Gln Gly Gly Tyr
1               5                   10                  15

Gly Gln Gly Ala Gly Ser Ser
            20

<210> SEQ ID NO 7
<211> LENGTH: 17
<212> TYPE: PRT
<213> ORGANISM: Artificial Sequence
<220> FEATURE:
<223> OTHER INFORMATION: Consensus sequence derived from internal
      repeats of Euprosthenops australis MaSp1
<220> FEATURE:
<221> NAME/KEY: VARIANT
```

```
<222> LOCATION: (9)..(9)
<223> OTHER INFORMATION: Arg
<220> FEATURE:
<221> NAME/KEY: VARIANT
<222> LOCATION: (14)..(14)
<223> OTHER INFORMATION: Ser
<220> FEATURE:
<221> NAME/KEY: VARIANT
<222> LOCATION: (16)..(16)
<223> OTHER INFORMATION: Gly

<400> SEQUENCE: 7

Gly Gln Gly Gly Gln Gly Gln Gly Gly Tyr Gly Gln Gly Ala Gly Ser
1               5                   10                  15

Ser

<210> SEQ ID NO 8
<211> LENGTH: 14
<212> TYPE: PRT
<213> ORGANISM: Artificial Sequence
<220> FEATURE:
<223> OTHER INFORMATION: Consensus sequence derived from internal
      repeats of Euprosthenops australis MaSp1
<220> FEATURE:
<221> NAME/KEY: VARIANT
<222> LOCATION: (2)..(2)
<223> OTHER INFORMATION: Gln
<220> FEATURE:
<221> NAME/KEY: VARIANT
<222> LOCATION: (6)..(6)
<223> OTHER INFORMATION: Arg
<220> FEATURE:
<221> NAME/KEY: VARIANT
<222> LOCATION: (11)..(11)
<223> OTHER INFORMATION: Ser
<220> FEATURE:
<221> NAME/KEY: VARIANT
<222> LOCATION: (11)..(11)
<223> OTHER INFORMATION: Val

<400> SEQUENCE: 8

Gly Arg Gly Gln Gly Gly Tyr Gly Gln Gly Ala Gly Gly Asn
1               5                   10

<210> SEQ ID NO 9
<211> LENGTH: 290
<212> TYPE: PRT
<213> ORGANISM: Artificial Sequence
<220> FEATURE:
<223> OTHER INFORMATION: Fusion protein

<400> SEQUENCE: 9

Gly Pro Asn Ser Gly Ile Gly Lys Phe Leu His Ser Ala Gly Lys Phe
1               5                   10                  15

Gly Lys Ala Phe Val Gly Glu Ile Met Lys Ser Gly Ser Ala Ser Gly
                20                  25                  30

Gln Gly Gly Tyr Gly Gly Leu Gly Gln Gly Gly Tyr Gly Gln Gly Ala
            35                  40                  45

Gly Ser Ser Ala Ala Ala Ala Ala Ala Ala Ala Ala Ala Ala Ala Gly
    50                  55                  60

Gly Gln Gly Gly Gln Gly Gln Gly Gly Tyr Gly Gln Gly Ser Gly Gly
65                  70                  75                  80

Ser Ala Ala Ala Ala Ala Ala Ala Ala Ala Ala Ala Ala Ala Ala Ala
                85                  90                  95

Gly Arg Gly Gln Gly Gly Tyr Gly Gln Gly Ser Gly Gly Asn Ala Ala
                100                 105                 110
```

```
Ala Ala Ala Ala Ala Ala Ala Ala Ala Ala Gly Gln Gly
        115                 120                 125

Gly Gln Gly Gly Tyr Gly Arg Gln Ser Gln Ala Gly Ser Ala Ala
    130                 135                 140

Ala Ala Ala Ala Ala Ala Ala Ala Ala Ala Gly Ser Gly Gln
145                 150                 155                 160

Gly Gly Tyr Gly Gly Gln Gly Gln Gly Tyr Gly Gln Ser Ala
            165                 170                 175

Ser Ala Ser Ala Ala Ser Ala Ala Ser Thr Val Ala Asn Ser Val
        180                 185                 190

Ser Arg Leu Ser Ser Pro Ser Ala Val Ser Arg Val Ser Ser Ala Val
        195                 200                 205

Ser Ser Leu Val Ser Asn Gly Gln Val Asn Met Ala Ala Leu Pro Asn
        210                 215                 220

Ile Ile Ser Asn Ile Ser Ser Val Ser Ala Ser Ala Pro Gly Ala
225                 230                 235                 240

Ser Gly Cys Glu Val Ile Val Gln Ala Leu Leu Glu Val Ile Thr Ala
                245                 250                 255

Leu Val Gln Ile Val Ser Ser Ser Val Gly Tyr Ile Asn Pro Ser
        260                 265                 270

Ala Val Asn Gln Ile Thr Asn Val Val Ala Asn Ala Met Ala Gln Val
        275                 280                 285

Met Gly
    290

<210> SEQ ID NO 10
<211> LENGTH: 870
<212> TYPE: DNA
<213> ORGANISM: Artificial Sequence
<220> FEATURE:
<223> OTHER INFORMATION: Fusion protein

<400> SEQUENCE: 10
ggtccgaatt caggaattgg taaattttg cactcagcag gaaaatttgg aaaagctttt      60
gtgggagaga taatgaaatc aggatccgct agcggtcaag gaggatatgg tggactaggt     120
caaggagggt atggacaagg tgcaggaagt tctgcagccg ctgccgccgc cgcagcagcc     180
gccgcagcag gtgacaagg tggacaaggt caaggaggat atggacaagg ttcaggaggt     240
tctgcagccg ccgccgccgc cgcagcagca gcagcagctg cagcagctgg acgaggtcaa     300
ggaggatatg gccaaggttc tggaggtaat gctgctgccg cagccgctgc cgccgccgcc     360
gccgctgcag cagccggaca gggaggtcaa ggtggatatg gtagacaaag ccaaggtgct     420
ggttccgctg ctgctgctgc tgctgctgct gccgctgctg ctgctgcagg atctggacaa     480
ggtggatacg gtggacaagg tcaaggaggt tatggtcaga gtagtgcttc tgcttcagct     540
gctgcgtcag ctgctagtac tgtagctaat tcggtgagtc gcctctcatc gccttccgca     600
gtatctcgag tttcttcagc agtttctagc ttggtttcaa atggtcaagt gaatatggca     660
gcgttaccta atatcattc caacattct tcttctgtca gtgcatctgc tcctggtgct       720
tctggatgtg aggtcatagt gcaagctcta ctcgaagtca tcactgctct tgttcaaatc     780
gttagttctt ctagtgttgg atatattaat ccatctgctg tgaaccaaat tactaatgtt     840
gttgctaatg ccatggctca agtaatgggc                                      870

<210> SEQ ID NO 11
<211> LENGTH: 277
```

```
<212> TYPE: PRT
<213> ORGANISM: Artificial Sequence
<220> FEATURE:
<223> OTHER INFORMATION: Fusion protein
<220> FEATURE:
<221> NAME/KEY: DISULFID
<222> LOCATION: (5)..(14)

<400> SEQUENCE: 11

Gly Pro Asn Ser Cys Thr Gly Arg Gly Asp Ser Pro Ala Cys Gly Ser
1               5                   10                  15

Ala Ser Gly Gln Gly Gly Tyr Gly Gly Leu Gly Gln Gly Gly Tyr Gly
            20                  25                  30

Gln Gly Ala Gly Ser Ala Ala Ala Ala Ala Ala Ala Ala Ala Ala Ala
        35                  40                  45

Ala Ala Gly Gly Gln Gly Gly Gln Gly Gln Gly Gly Tyr Gly Gln Gly
    50                  55                  60

Ser Gly Gly Ser Ala Ala Ala Ala Ala Ala Ala Ala Ala Ala Ala Ala
65                  70                  75                  80

Ala Ala Ala Gly Arg Gly Gln Gly Gly Tyr Gly Gln Gly Ser Gly Gly
                85                  90                  95

Asn Ala Ala Ala Ala Ala Ala Ala Ala Ala Ala Ala Ala Ala Ala Ala
            100                 105                 110

Gly Gln Gly Gly Gln Gly Gly Tyr Gly Arg Gln Ser Gln Gly Ala Gly
        115                 120                 125

Ser Ala Ala Ala Ala Ala Ala Ala Ala Ala Ala Ala Ala Ala Ala Gly
    130                 135                 140

Ser Gly Gln Gly Gly Tyr Gly Gly Gln Gly Gly Tyr Gly Gly Tyr Gly Gln
145                 150                 155                 160

Ser Ser Ala Ser Ala Ser Ala Ala Ala Ser Ala Ala Ser Thr Val Ala
                165                 170                 175

Asn Ser Val Ser Arg Leu Ser Ser Pro Ser Ala Val Ser Arg Val Ser
            180                 185                 190

Ser Ala Val Ser Ser Leu Val Ser Asn Gly Gln Val Asn Met Ala Ala
        195                 200                 205

Leu Pro Asn Ile Ile Ser Asn Ile Ser Ser Val Ser Ala Ser Ala
    210                 215                 220

Pro Gly Ala Ser Gly Cys Glu Val Ile Val Gln Ala Leu Leu Glu Val
225                 230                 235                 240

Ile Thr Ala Leu Val Gln Ile Val Ser Ser Ser Val Gly Tyr Ile
                245                 250                 255

Asn Pro Ser Ala Val Asn Gln Ile Thr Asn Val Val Ala Asn Ala Met
            260                 265                 270

Ala Gln Val Met Gly
        275

<210> SEQ ID NO 12
<211> LENGTH: 831
<212> TYPE: DNA
<213> ORGANISM: Artificial Sequence
<220> FEATURE:
<223> OTHER INFORMATION: Fusion protein

<400> SEQUENCE: 12
ggtccgaatt catgcacagg tcgtggtgat tctccggcgt gcggatccgc tagcggtcaa     60
ggaggatatg gtggactagg tcaaggaggg tatggacaag gtgcaggaag ttctgcagcc    120
gctgccgccg ccgcagcagc cgccgcagca ggtggacaag gtggacaagg tcaaggagga    180
```

```
tatggacaag gttcaggagg ttctgcagcc gccgccgccg ccgcagcagc agcagcagct    240
gcagcagctg gacgaggtca aggaggatat ggccaaggtt ctggaggtaa tgctgctgcc    300
gcagccgctg ccgccgccgc cgccgctgca gcagccggac agggaggtca aggtggatat    360
ggtagacaaa gccaaggtgc tggttccgct gctgctgctg ctgctgctgc tgccgctgct    420
gctgctgcag gatctggaca aggtggatac ggtggacaag gtcaaggagg ttatggtcag    480
agtagtgctt ctgcttcagc tgctgcgtca gctgctagta ctgtagctaa ttcggtgagt    540
cgcctctcat cgccttccgc agtatctcga gtttcttcag cagtttctag cttggtttca    600
aatggtcaag tgaatatggc agcgttacct aatatcattt ccaacatttc ttcttctgtc    660
agtgcatctg ctcctggtgc ttctggatgt gaggtcatag tgcaagctct actcgaagtc    720
atcactgctc ttgttcaaat cgttagttct tctagtgttg gatatattaa tccatctgct    780
gtgaaccaaa ttactaatgt tgttgctaat gccatggctc aagtaatggg c            831
```

<210> SEQ ID NO 13
<211> LENGTH: 339
<212> TYPE: PRT
<213> ORGANISM: Artificial Sequence
<220> FEATURE:
<223> OTHER INFORMATION: Fusion protein

<400> SEQUENCE: 13

```
Met Gly Ser Ser Gly His His His His His Met Val Asp Asn Lys
1               5                   10                  15

Phe Asn Lys Glu Gln Gln Asn Ala Phe Tyr Glu Ile Leu His Leu Pro
            20                  25                  30

Asn Leu Asn Glu Glu Gln Arg Asn Ala Phe Ile Gln Ser Leu Lys Asp
        35                  40                  45

Asp Pro Ser Gln Ser Ala Asn Leu Leu Ala Glu Ala Lys Lys Leu Asn
    50                  55                  60

Asp Ala Gln Ala Pro Lys Leu Glu Ala Leu Phe Gln Gly Pro Asn Ser
65                  70                  75                  80

Gly Gln Gly Gly Tyr Gly Gly Leu Gly Gln Gly Gly Tyr Gly Gln Gly
                85                  90                  95

Ala Gly Ser Ser Ala Ala Ala Ala Ala Ala Ala Ala Ala Ala Ala Ala
            100                 105                 110

Gly Gly Gln Gly Gly Gln Gly Gln Gly Gly Tyr Gly Gln Gly Ser Gly
        115                 120                 125

Gly Ser Ala Ala Ala Ala Ala Ala Ala Ala Ala Ala Ala Ala
    130                 135                 140

Ala Gly Arg Gly Gln Gly Gly Tyr Gly Gln Gly Ser Gly Gly Asn Ala
145                 150                 155                 160

Ala Ala Ala Ala Ala Ala Ala Ala Ala Ala Ala Ala Ala Ala Gly Gln
                165                 170                 175

Gly Gly Gln Gly Gly Tyr Gly Arg Gln Ser Gln Gly Ala Gly Ser Ala
            180                 185                 190

Ala Ala Ala Ala Ala Ala Ala Ala Ala Ala Ala Ala Ala Gly Ser Gly
        195                 200                 205

Gln Gly Gly Tyr Gly Gly Gln Gly Gln Gly Gly Tyr Gly Gln Ser Ser
    210                 215                 220

Ala Ser Ala Ser Ala Ala Ala Ser Ala Ala Ser Thr Val Ala Asn Ser
225                 230                 235                 240

Val Ser Arg Leu Ser Ser Pro Ser Ala Val Ser Arg Val Ser Ser Ala
```

```
                    245                 250                 255
Val Ser Ser Leu Val Ser Asn Gly Gln Val Asn Met Ala Ala Leu Pro
            260                 265                 270

Asn Ile Ile Ser Asn Ile Ser Ser Val Ser Ala Ser Ala Pro Gly
        275                 280                 285

Ala Ser Gly Cys Glu Val Ile Val Gln Ala Leu Leu Glu Val Ile Thr
    290                 295                 300

Ala Leu Val Gln Ile Val Ser Ser Ser Val Gly Tyr Ile Asn Pro
305                 310                 315                 320

Ser Ala Val Asn Gln Ile Thr Asn Val Val Ala Asn Ala Met Ala Gln
                325                 330                 335

Val Met Gly

<210> SEQ ID NO 14
<211> LENGTH: 1017
<212> TYPE: DNA
<213> ORGANISM: Artificial Sequence
<220> FEATURE:
<223> OTHER INFORMATION: Fusion protein

<400> SEQUENCE: 14
atgggcagca gcggccatca tcatcatcat catatggtag acaacaaatt caacaaagaa      60
caacaaaacg cgttctatga gatcttacat ttacctaact aaacgaaga caacgaaac      120 gccttcatcc aaagtttaaa agatgaccca agccaaagcg ctaacttgct agcagaagct      180
aaaaagctaa atgatgctca ggcgccgaaa ctggaagctc tgttccaggg tccgaattca      240
ggtcaaggtg gatatggtgg actaggtcaa ggaggatatg gacaaggtgc aggaagttct      300
gcagccgctg ccgccgccgc agcagccgcc gcagcaggtg acaaggtgg acaaggtcaa      360 ggaggatatg gacaaggttc aggaggttct gcagccgccg ccgccgccgc agcagcagca      420
gcagctgcag cagctggacg aggtcaagga ggatatggtc aaggttctgg aggtaatgct      480
gctgccgcag ccgctgccgc cgccgccgcc gctgcagcag ccggacaggg aggtcaaggt      540
ggatatggta gacaaagcca aggtgctggt tccgctgctg ctgctgctgc tgctgctgcc      600
gctgctgctg ctgcaggatc tggacaaggt ggatacggtg acaaggtca aggaggttat      660 ggtcagagta gtgcttctgc ttcagctgct gcgtcagctg ctagtactgt agctaattcg      720
gtgagtcgcc tctcatcgcc ttccgcagta tctcgagttt cttcagcagt ttctagcttg      780
gtttcaaatg gtcaagtgaa tatggcagcg ttacctaata tcatttccaa catttcttct      840
tctgtcagtg catctgctcc tggtgcttct ggatgtgagg tcatagtgca agctctactc      900
gaagtcatca ctgctcttgt tcaaatcgtt agttcttcta gtgttggata tattaatcca      960
tctgctgtga accaaattac taatgttgtt gctaatgcca tggctcaagt aatgggc      1017

<210> SEQ ID NO 15
<211> LENGTH: 336
<212> TYPE: PRT
<213> ORGANISM: Artificial Sequence
<220> FEATURE:
<223> OTHER INFORMATION: Fusion protein

<400> SEQUENCE: 15

Met Gly Ser Ser Gly His His His His His His Met Thr Tyr Lys Leu
1               5                   10                  15

Val Ile Asn Gly Lys Thr Leu Lys Gly Glu Thr Thr Thr Glu Ala Val
            20                  25                  30
```

```
Asp Ala Ala Thr Ala Glu Lys Val Phe Lys Gln Tyr Ala Asn Asp Asn
             35                  40                  45
Gly Val Asp Gly Glu Trp Thr Tyr Asp Ala Thr Lys Thr Phe Thr
 50                  55                  60
Val Thr Glu Leu Glu Ala Leu Phe Gln Gly Pro Asn Ser Gly Gln Gly
 65                  70                  75                  80
Gly Tyr Gly Gly Leu Gly Gln Gly Gly Tyr Gly Gln Gly Ala Gly Ser
                 85                  90                  95
Ser Ala Ala Ala Ala Ala Ala Ala Ala Ala Ala Gly Gly Gln
            100                 105                 110
Gly Gly Gln Gly Gln Gly Gly Tyr Gly Gln Gly Ser Gly Gly Ser Ala
            115                 120                 125
Ala Ala Ala Ala Ala Ala Ala Ala Ala Ala Ala Ala Gly Arg
            130                 135                 140
Gly Gln Gly Gly Tyr Gly Gln Gly Ser Gly Gly Asn Ala Ala Ala Ala
145                 150                 155                 160
Ala Ala Ala Ala Ala Ala Ala Ala Ala Ala Gly Gln Gly Gly Gln
            165                 170                 175
Gly Gly Tyr Gly Arg Gln Ser Gln Gly Ala Gly Ser Ala Ala Ala Ala
            180                 185                 190
Ala Ala Ala Ala Ala Ala Ala Ala Gly Ser Gly Gln Gly Gly
            195                 200                 205
Tyr Gly Gly Gln Gly Gln Gly Gly Tyr Gly Gln Ser Ala Ser Ala
            210                 215                 220
Ser Ala Ala Ala Ser Ala Ala Ser Thr Val Ala Asn Ser Val Ser Arg
225                 230                 235                 240
Leu Ser Ser Pro Ser Ala Val Ser Arg Val Ser Ser Ala Val Ser Ser
                245                 250                 255
Leu Val Ser Asn Gly Gln Val Asn Met Ala Ala Leu Pro Asn Ile Ile
                260                 265                 270
Ser Asn Ile Ser Ser Ser Val Ser Ala Ser Ala Pro Gly Ala Ser Gly
                275                 280                 285
Cys Glu Val Ile Val Gln Ala Leu Leu Glu Val Ile Thr Ala Leu Val
            290                 295                 300
Gln Ile Val Ser Ser Ser Ser Val Gly Tyr Ile Asn Pro Ser Ala Val
305                 310                 315                 320
Asn Gln Ile Thr Asn Val Val Ala Asn Ala Met Ala Gln Val Met Gly
                325                 330                 335
```

<210> SEQ ID NO 16
<211> LENGTH: 1008
<212> TYPE: DNA
<213> ORGANISM: Artificial Sequence
<220> FEATURE:
<223> OTHER INFORMATION: Fusion protein

<400> SEQUENCE: 16

| | | |
|---|---|---|
| atgggcagca gcggccatca tcatcatcat catatgactt acaaacttgt tattaatggt | 60 |
| aaaacattga aggcgaaac aactactgaa gctgttgatg ctgctactgc agaaaaagtc | 120 |
| ttcaaacaat acgctaacga caacggtgtt gacggtgaat ggacttacga cgatgcgact | 180 |
| aagacctta cagttactga actggaagct ctgttccagg gtccgaattc aggtcaaggt | 240 |
| ggatatggtg gactaggtca aggaggatat ggacaaggtg caggaagttc tgcagccgct | 300 |
| gccgccgccg cagcagccgc cgcagcaggt ggacaaggtg acaaggtca aggaggatat | 360 |

```
ggacaaggtt caggaggttc tgcagccgcc gccgccgccg cagcagcagc agcagctgca    420
gcagctggac gaggtcaagg aggatatggt caaggttctg gaggtaatgc tgctgccgca    480
gccgctgccg ccgccgccgc cgctgcagca gccggacagg gaggtcaagg tggatatggt    540
agacaaagcc aaggtgctgg ttccgctgct gctgctgctg ctgctgctgc cgctgctgct    600
gctgcaggat ctggacaagg tggatacggt ggacaaggtc aaggaggtta tggtcagagt    660
agtgcttctg cttcagctgc tgcgtcagct gctagtactg tagctaattc ggtgagtcgc    720
ctctcatcgc cttccgcagt atctcgagtt tcttcagcag tttctagctt ggtttcaaat    780
ggtcaagtga atatggcagc gttacctaat atcatttcca acatttcttc ttctgtcagt    840
gcatctgctc ctggtgcttc tggatgtgag gtcatagtgc aagctctact cgaagtcatc    900
actgctcttg ttcaaatcgt tagttcttct agtgttggat atattaatcc atctgctgtg    960
aaccaaatta ctaatgttgt tgctaatgcc atggctcaag taatgggc                 1008
```

<210> SEQ ID NO 17
<211> LENGTH: 327
<212> TYPE: PRT
<213> ORGANISM: Artificial Sequence
<220> FEATURE:
<223> OTHER INFORMATION: Fusion protein

<400> SEQUENCE: 17

```
Met Gly Ser Ser Gly His His His His His Met Leu Ala Glu Ala
1               5                   10                  15

Lys Val Leu Ala Asn Arg Glu Leu Asp Lys Tyr Gly Val Ser Asp Tyr
            20                  25                  30

Tyr Lys Asn Leu Ile Asn Asn Ala Lys Thr Val Glu Gly Val Lys Ala
        35                  40                  45

Leu Ile Asp Glu Ile Leu Ala Ala Leu Pro Leu Glu Ala Leu Phe Gln
    50                  55                  60

Gly Pro Asn Ser Gly Gln Gly Gly Tyr Gly Gly Leu Gly Gln Gly Gly
65                  70                  75                  80

Tyr Gly Gln Gly Ala Gly Ser Ser Ala Ala Ala Ala Ala Ala Ala Ala
                85                  90                  95

Ala Ala Ala Ala Gly Gly Gln Gly Gly Gln Gly Gly Tyr Gly
            100                 105                 110

Gln Gly Ser Gly Gly Ser Ala Ala Ala Ala Ala Ala Ala Ala Ala Ala
        115                 120                 125

Ala Ala Ala Ala Ala Gly Arg Gly Gln Gly Gly Tyr Gly Gln Gly Ser
    130                 135                 140

Gly Gly Asn Ala Ala Ala Ala Ala Ala Ala Ala Ala Ala Ala Ala Ala
145                 150                 155                 160

Ala Ala Gly Gln Gly Gly Gln Gly Gly Tyr Gly Arg Gln Ser Gln Gly
                165                 170                 175

Ala Gly Ser Ala Ala Ala Ala Ala Ala Ala Ala Ala Ala Ala Ala Ala
            180                 185                 190

Ala Gly Ser Gly Gln Gly Gly Tyr Gly Gly Gln Gly Gln Gly Gly Tyr
        195                 200                 205

Gly Gln Ser Ser Ala Ser Ala Ser Ala Ala Ala Ser Ala Ala Ser Thr
    210                 215                 220

Val Ala Asn Ser Val Ser Arg Leu Ser Ser Pro Ser Ala Val Ser Arg
225                 230                 235                 240

Val Ser Ser Ala Val Ser Ser Leu Val Ser Asn Gly Gln Val Asn Met
                245                 250                 255
```

```
Ala Ala Leu Pro Asn Ile Ile Ser Asn Ile Ser Ser Val Ser Ala
            260                 265                 270

Ser Ala Pro Gly Ala Ser Gly Cys Glu Val Ile Val Gln Ala Leu Leu
        275                 280                 285

Glu Val Ile Thr Ala Leu Val Gln Ile Val Ser Ser Ser Val Gly
    290                 295                 300

Tyr Ile Asn Pro Ser Ala Val Asn Gln Ile Thr Asn Val Val Ala Asn
305                 310                 315                 320

Ala Met Ala Gln Val Met Gly
                325
```

<210> SEQ ID NO 18
<211> LENGTH: 981
<212> TYPE: DNA
<213> ORGANISM: Artificial Sequence
<220> FEATURE:
<223> OTHER INFORMATION: Fusion protein

<400> SEQUENCE: 18

```
atgggcagca gcggccatca tcatcatcat catatgttag ctgaagctaa agtcttagct    60
aacagagaac ttgacaaata tggagtaagt gactattaca agaacctaat caacaatgcc   120
aaaactgttg aaggtgtaaa agcactgata gatgaaattt tagctgcatt acctctggaa   180
gctctgttcc agggtccgaa ttcaggtcaa ggtggatatg gtggactagg tcaaggagga   240
tatggacaag gtgcaggaag ttctgcagcc gctgccgccg ccgcagcagc cgccgcagca   300
ggtggacaag gtggacaagg tcaaggagga tatggacaag gttcaggagg ttctgcagcc   360
gccgccgccg ccgcagcagc agcagcagct gcagcagctg acgaggtcaa ggaggatat   420
ggtcaaggtt ctggaggtaa tgctgctgcc gcagccgctg ccgccgccgc cgccgctgca   480
gcagccggac agggaggtca aggtggatat ggtagacaaa gccaaggtgc tggttccgct   540
gctgctgctg ctgctgctgc tgccgctgct gctgctgcag atctggaca aggtggatac   600
ggtggacaag gtcaaggagg ttatggtcag agtagtgctt ctgcttcagc tgctgcgtca   660
gctgctagta ctgtagctaa ttcggtgagt cgcctctcat cgccttccgc agtatctcga   720
gtttcttcag cagtttctag cttggtttca atggtcaag tgaatatggc agcgttacct   780
aatatcattt ccaacatttc ttcttctgtc agtgcatctg ctcctggtgc ttctggatgt   840
gaggtcatag tgcaagctct actcgaagtc atcactgctc ttgttcaaat cgttagttct   900
tctagtgttg gatatattaa tccatctgct gtgaaccaaa ttactaatgt tgttgctaat   960
gccatggctc aagtaatggg c                                             981
```

<210> SEQ ID NO 19
<211> LENGTH: 429
<212> TYPE: PRT
<213> ORGANISM: Artificial Sequence
<220> FEATURE:
<223> OTHER INFORMATION: Fusion protein

<400> SEQUENCE: 19

```
Met His His His His His His Gly Gln Gly Gly Tyr Gly Gly Leu Gly
1               5                   10                  15

Gln Gly Gly Tyr Gly Gln Gly Ala Gly Ser Ser Ala Ala Ala Ala Ala
                20                  25                  30

Ala Ala Ala Ala Ala Ala Ala Gly Gly Gln Gly Gly Gln Gly Gln Gly
        35                  40                  45
```

-continued

```
Gly Tyr Gly Gln Gly Ser Gly Ser Ala Ala Ala Ala Ala Ala
         50              55              60
Ala Ala Ala Ala Ala Ala Ala Gly Arg Gly Gln Gly Gly Tyr Gly
 65                  70                  75              80
Gln Gly Ser Gly Gly Asn Ala Ala Ala Ala Ala Ala Ala Ala
             85                  90                  95
Ala Ala Ala Ala Gly Gln Gly Gly Gln Gly Gly Tyr Gly Arg Gln
        100                 105                 110
Ser Gln Gly Ala Gly Ser Ala Ala Ala Ala Ala Ala Ala Ala
        115                 120                 125
Ala Ala Ala Gly Ser Gly Gln Gly Gly Tyr Gly Gly Gln Gly Gln
    130                 135                 140
Gly Gly Tyr Gly Gln Ser Ser Ala Ser Ala Ser Ala Ala Ser Ala
145                 150                 155                 160
Ala Ser Thr Val Ala Asn Ser Val Ser Arg Leu Ser Pro Ser Ala
                165                 170                 175
Val Ser Arg Val Ser Ser Ala Val Ser Ser Leu Val Ser Asn Gly Gln
            180                 185                 190
Val Asn Met Ala Ala Leu Pro Asn Ile Ile Ser Asn Ile Ser Ser Ser
        195                 200                 205
Val Ser Ala Ser Ala Pro Gly Ala Ser Gly Cys Glu Val Ile Val Gln
    210                 215                 220
Ala Leu Leu Glu Val Ile Thr Ala Leu Val Gln Ile Val Ser Ser Ser
225                 230                 235                 240
Ser Val Gly Tyr Ile Asn Pro Ser Ala Val Asn Gln Ile Thr Asn Val
                245                 250                 255
Val Ala Asn Ala Met Ala Gln Val Met Gly Asn Ser Gly Ser Gly
            260                 265                 270
Ser Gly Ser Ala Ala Gly Ser Ile Thr Thr Leu Pro Ala Leu Pro Glu
        275                 280                 285
Asp Gly Gly Ser Gly Ala Phe Pro Pro Gly His Phe Lys Asp Pro Lys
    290                 295                 300
Arg Leu Tyr Cys Lys Asn Gly Gly Phe Phe Leu Arg Ile His Pro Asp
305                 310                 315                 320
Gly Arg Val Asp Gly Val Arg Glu Lys Ser Asp Pro His Ile Lys Leu
                325                 330                 335
Gln Leu Gln Ala Glu Glu Arg Gly Val Val Ser Ile Lys Gly Val Cys
            340                 345                 350
Ala Asn Arg Tyr Leu Ala Met Lys Glu Asp Gly Arg Leu Leu Ala Ser
        355                 360                 365
Lys Cys Val Thr Asp Glu Cys Phe Phe Phe Glu Arg Leu Glu Ser Asn
    370                 375                 380
Asn Tyr Asn Thr Tyr Arg Ser Arg Lys Tyr Thr Ser Trp Tyr Val Ala
385                 390                 395                 400
Leu Lys Arg Thr Gly Gln Tyr Lys Leu Gly Ser Lys Thr Gly Pro Gly
                405                 410                 415
Gln Lys Ala Ile Leu Phe Leu Pro Met Ser Ala Lys Ser
            420                 425
```

<210> SEQ ID NO 20
<211> LENGTH: 1287
<212> TYPE: DNA
<213> ORGANISM: Artificial Sequence
<220> FEATURE:
<223> OTHER INFORMATION: Fusion protein

<400> SEQUENCE: 20

```
atgcatcatc atcatcatca tggtcaaggt ggatatggtg gactaggtca aggaggatat      60
ggacaaggtg caggaagttc tgcagccgct gccgccgccg cagcagccgc cgcagcaggt     120
ggacaaggtg acaaggtca aggaggatat ggacaaggtt caggaggttc tgcagccgcc     180
gccgccgccg cagcagcagc agcagctgca gcagctggac gaggtcaagg aggatatggt     240
caaggttctg gaggtaatgc tgctgccgca gccgctgccg ccgccgccgc cgctgcagca     300
gccggacagg gaggtcaagg tggatatggt agacaaagcc aaggtgctgg ttccgctgct     360
gctgctgctg ctgctgctgc cgctgctgct gctgcaggat ctggacaagg tggatacggt     420
ggacaaggtc aaggaggtta tggtcagagt agtgcttctg cttcagctgc tgcgtcagct     480
gctagtactg tagctaattc ggtgagtcgc ctctcatcgc cttccgcagt atctcgagtt     540
tcttcagcag tttctagctt ggtttcaaat ggtcaagtga atatggcagc gttacctaat     600
atcatttcca acatttcttc ttctgtcagt gcatctgctc ctggtgcttc tggatgtgag     660
gtcatagtgc aagctctact cgaagtcatc actgctcttg ttcaaatcgt tagttcttct     720
agtgttggat atattaatcc atctgctgtg aaccaaatta ctaatgttgt tgctaatgcc     780
atggctcaag taatgggcgg gaattcaggt agcggcagcg tagcgcagc cgggagcatc     840
accacgctgc cgccttgcc cgaggatggc ggcagcggcg ccttcccgcc cggccacttc     900
aaggacccca gcggctgta ctgcaaaaac gggggcttct tcctgcgcat ccaccccgac     960
ggccgagttg acgggtccg ggagaagagc gaccctcaca tcaagctaca acttcaagca    1020
gaagagagag gagttgtgtc tatcaaagga gtgtgtgcta accgttacct ggctatgaag    1080
gaagatggaa gattactggc ttctaaatgt gttacggatg agtgtttctt ttttgaacga    1140
ttggaatcta ataactacaa tacttaccgg tcaaggaaat acaccagttg gtatgtggca    1200
ctgaaacgaa ctgggcagta taacttgga tccaaaacag gacctgggca gaaagctata    1260
cttttcttc caatgtctgc taagagc                                         1287
```

<210> SEQ ID NO 21
<211> LENGTH: 427
<212> TYPE: PRT
<213> ORGANISM: Artificial Sequence
<220> FEATURE:
<223> OTHER INFORMATION: Fusion protein

<400> SEQUENCE: 21

```
Met Gly Ser Ser Gly His His His His His Met Met Gly Lys Ile
1               5                   10                  15

Ser Ser Leu Pro Thr Gln Leu Phe Lys Cys Cys Phe Cys Asp Phe Leu
            20                  25                  30

Lys Val Lys Met His Thr Met Ser Ser His Leu Phe Tyr Leu Ala
        35                  40                  45

Leu Cys Leu Leu Thr Phe Thr Ser Ser Ala Thr Ala Gly Pro Glu Thr
    50                  55                  60

Leu Cys Gly Ala Glu Leu Val Asp Ala Leu Gln Phe Val Cys Gly Asp
65                  70                  75                  80

Arg Gly Phe Tyr Phe Asn Lys Pro Thr Gly Tyr Gly Ser Ser Ser Arg
                85                  90                  95

Arg Ala Pro Gln Thr Gly Ile Val Asp Glu Cys Cys Phe Arg Ser Cys
            100                 105                 110

Asp Leu Arg Arg Leu Glu Met Tyr Cys Ala Pro Leu Lys Pro Ala Lys
```

```
            115                 120                 125
Ser Ala Arg Ser Val Arg Ala Gln Arg His Thr Asp Met Pro Lys Thr
        130                 135                 140

Gln Lys Glu Val His Leu Lys Asn Ala Ser Arg Gly Ser Ala Gly Asn
145                 150                 155                 160

Lys Asn Tyr Arg Met Pro Asn Ser Gly Gln Gly Tyr Gly Gly Leu
                165                 170                 175

Gly Gln Gly Gly Tyr Gly Gln Gly Ala Gly Ser Ser Ala Ala Ala
            180                 185                 190

Ala Ala Ala Ala Ala Ala Ala Gly Gly Gln Gly Gly Gln Gly Gln
        195                 200                 205

Gly Gly Tyr Gly Gln Gly Ser Gly Ser Ala Ala Ala Ala Ala
        210                 215                 220

Ala Ala Ala Ala Ala Ala Ala Ala Gly Arg Gly Gln Gly Gly Tyr
225                 230                 235                 240

Gly Gln Gly Ser Gly Gly Asn Ala Ala Ala Ala Ala Ala Ala
                245                 250                 255

Ala Ala Ala Ala Ala Ala Gly Gln Gly Gly Gln Gly Gly Tyr Gly Arg
            260                 265                 270

Gln Ser Gln Gly Ala Gly Ser Ala Ala Ala Ala Ala Ala Ala Ala
        275                 280                 285

Ala Ala Ala Ala Ala Gly Ser Gly Gln Gly Gly Tyr Gly Gly Gln Gly
        290                 295                 300

Gln Gly Gly Tyr Gly Gln Ser Ser Ala Ser Ala Ser Ala Ala Ala Ser
305                 310                 315                 320

Ala Ala Ser Thr Val Ala Asn Ser Val Ser Arg Leu Ser Ser Pro Ser
                325                 330                 335

Ala Val Ser Arg Val Ser Ser Ala Val Ser Ser Leu Val Ser Asn Gly
                340                 345                 350

Gln Val Asn Met Ala Ala Leu Pro Asn Ile Ile Ser Asn Ile Ser Ser
            355                 360                 365

Ser Val Ser Ala Ser Ala Pro Gly Ala Ser Gly Cys Glu Val Ile Val
370                 375                 380

Gln Ala Leu Leu Glu Val Ile Thr Ala Leu Val Gln Ile Val Ser Ser
385                 390                 395                 400

Ser Ser Val Gly Tyr Ile Asn Pro Ser Ala Val Asn Gln Ile Thr Asn
                405                 410                 415

Val Val Ala Asn Ala Met Ala Gln Val Met Gly
            420                 425

<210> SEQ ID NO 22
<211> LENGTH: 1281
<212> TYPE: DNA
<213> ORGANISM: Artificial Sequence
<220> FEATURE:
<223> OTHER INFORMATION: Fusion protein

<400> SEQUENCE: 22
atgggcagca gcggccatca tcatcatcat catatgatgg gaaaaatcag cagtcttcca      60
acccaattat ttaagtgctg cttttgtgat ttcttgaagg tgaagatgca caccatgtcc     120
tcctcgcatc tcttctacct ggcgctgtgc ctgctcacct tcaccagctc tgccacggct     180
ggaccggaga cgctctgcgg ggctgagctg gtggatgctc ttcagttcgt gtgtggagac     240 agggctttt atttcaacaa gcccacaggg tatgctcca gcagtcggag ggcgcctcag     300
```

```
acaggtatcg tggatgagtg ctgcttccgg agctgtgatc taaggaggct ggagatgtat    360
tgcgcacccc tcaagcctgc caagtcagct cgctctgtcc gtgcccagcg ccacaccgac    420
atgcccaaga cccagaagga agtacatttg aagaacgcaa gtagagggag tgcaggaaac    480
aagaactaca ggatgccgaa ttcaggtcaa ggtggatatg gtggactagg tcaaggagga    540
tatggacaag gtgcaggaag ttctgcagcc gctgccgccg ccgcagcagc cgccgcagca    600
ggtggacaag gtgacaaggt caaggaggat atgggacaag gttcaggagg ttctgcagcc    660
gccgccgccg ccgcagcagc agcagcagct gcagcagctg gacgaggtca aggaggatat    720
ggtcaaggtt ctggaggtaa tgctgctgcc gcagccgctg ccgccgccgc cgccgctgca    780
gcagccggac agggaggtca aggtggatat ggtagacaaa gccaaggtgc tggttccgct    840
gctgctgctg ctgctgctgc tgccgctgct gctgctgcag atctggaca aggtggatac     900
ggtggacaag gtcaaggagg ttatggtcag agtagtgctt ctgcttcagc tgctgcgtca    960
gctgctagta ctgtagctaa ttcggtgagt cgcctctcat cgccttccgc agtatctcga   1020
gtttcttcag cagtttctag cttggtttca aatggtcaag tgaatatggc agcgttacct   1080
aatatcattt ccaacatttc ttcttctgtc agtgcatctg ctcctggtgc ttctggatgt   1140
gaggtcatag tgcaagctct actcgaagtc atcactgctc ttgttcaaat cgttagttct   1200
tctagtgttg gatatattaa tccatctgct gtgaaccaaa ttactaatgt tgttgctaat   1260
gccatggctc aagtaatggg c                                              1281

<210> SEQ ID NO 23
<211> LENGTH: 641
<212> TYPE: PRT
<213> ORGANISM: Artificial Sequence
<220> FEATURE:
<223> OTHER INFORMATION: Fusion protein

<400> SEQUENCE: 23

Met Gly Ser Ser Gly His His His His His Met Asn Cys Cys Val
1               5                  10                  15

Lys Gly Asn Ser Ile Tyr Pro Gln Lys Thr Ser Thr Lys Gln Thr Gly
                20                  25                  30

Leu Met Leu Asp Ile Ala Arg His Phe Tyr Ser Pro Glu Val Ile Lys
            35                  40                  45

Ser Phe Ile Asp Thr Ile Ser Leu Ser Gly Gly Asn Phe Leu His Leu
        50                  55                  60

His Phe Ser Asp His Glu Asn Tyr Ala Ile Glu Ser His Leu Leu Asn
65                  70                  75                  80

Gln Arg Ala Glu Asn Ala Val Gln Gly Lys Asp Gly Ile Tyr Ile Asn
                85                  90                  95

Pro Tyr Thr Gly Lys Pro Phe Leu Ser Tyr Arg Gln Leu Asp Asp Ile
            100                 105                 110

Lys Ala Tyr Ala Lys Ala Lys Gly Ile Glu Leu Ile Pro Glu Leu Asp
        115                 120                 125

Ser Pro Asn His Met Thr Ala Ile Phe Lys Leu Val Gln Lys Asp Arg
    130                 135                 140

Gly Val Lys Tyr Leu Gln Gly Leu Lys Ser Arg Gln Val Asp Asp Glu
145                 150                 155                 160

Ile Asp Ile Thr Asn Ala Asp Ser Ile Thr Phe Met Gln Ser Leu Met
                165                 170                 175

Ser Glu Val Ile Asp Ile Phe Gly Asp Thr Ser Gln His Phe His Ile
            180                 185                 190
```

```
Gly Gly Asp Glu Phe Gly Tyr Ser Val Glu Ser Asn His Glu Phe Ile
        195                 200                 205

Thr Tyr Ala Asn Lys Leu Ser Tyr Phe Leu Glu Lys Lys Gly Leu Lys
        210                 215                 220

Thr Arg Met Trp Asn Asp Gly Leu Ile Lys Asn Thr Phe Glu Gln Ile
225                 230                 235                 240

Asn Pro Asn Ile Glu Ile Thr Tyr Trp Ser Tyr Asp Gly Asp Thr Gln
                245                 250                 255

Asp Lys Asn Glu Ala Ala Glu Arg Arg Asp Met Arg Val Ser Leu Pro
                260                 265                 270

Glu Leu Leu Ala Lys Gly Phe Thr Val Leu Asn Tyr Asn Ser Tyr Tyr
            275                 280                 285

Leu Tyr Ile Val Pro Lys Ala Ser Pro Thr Phe Ser Gln Asp Ala Ala
        290                 295                 300

Phe Ala Ala Lys Asp Val Ile Lys Asn Trp Asp Leu Gly Val Trp Asp
305                 310                 315                 320

Gly Arg Asn Thr Lys Asn Arg Val Gln Asn Thr His Glu Ile Ala Gly
                325                 330                 335

Ala Ala Leu Ser Ile Trp Gly Glu Asp Ala Lys Ala Leu Lys Asp Glu
            340                 345                 350

Thr Ile Gln Lys Asn Thr Lys Ser Leu Leu Glu Ala Val Ile His Lys
        355                 360                 365

Thr Asn Gly Asp Glu Gly Pro Ala Ala Leu Gly Pro Asn Ser Gly Gln
370                 375                 380

Gly Gly Tyr Gly Gly Leu Gly Gln Gly Gly Tyr Gly Gln Gly Ala Gly
385                 390                 395                 400

Ser Ser Ala Ala Ala Ala Ala Ala Ala Ala Ala Ala Ala Ala Gly Gly
                405                 410                 415

Gln Gly Gly Gln Gly Gln Gly Gly Tyr Gly Gln Gly Ser Gly Gly Ser
            420                 425                 430

Ala Ala Ala Ala Ala Ala Ala Ala Ala Ala Ala Ala Ala Ala Ala Gly
        435                 440                 445

Arg Gly Gln Gly Gly Tyr Gly Gln Gly Ser Gly Gly Asn Ala Ala Ala
        450                 455                 460

Ala Ala Ala Ala Ala Ala Ala Ala Ala Ala Ala Gly Gln Gly Gly Gly
465                 470                 475                 480

Gln Gly Gly Tyr Gly Arg Gln Ser Gln Gly Ala Gly Ser Ala Ala Ala
                485                 490                 495

Ala Ala Ala Ala Ala Ala Ala Ala Ala Ala Gly Ser Gly Gln Gly Gly
                500                 505                 510

Gly Tyr Gly Gly Gln Gly Gln Gly Gly Tyr Gly Gln Ser Ser Ala Ser
            515                 520                 525

Ala Ser Ala Ala Ala Ser Ala Ala Ser Thr Val Ala Asn Ser Val Ser
        530                 535                 540

Arg Leu Ser Ser Pro Ser Ala Val Ser Arg Val Ser Ser Ala Val Ser
545                 550                 555                 560

Ser Leu Val Ser Asn Gly Gln Val Asn Met Ala Ala Leu Pro Asn Ile
                565                 570                 575

Ile Ser Asn Ile Ser Ser Val Ser Ala Ser Ala Pro Gly Ala Ser
                580                 585                 590

Gly Cys Glu Val Ile Val Gln Ala Leu Leu Glu Val Ile Thr Ala Leu
            595                 600                 605
```

```
Val Gln Ile Val Ser Ser Ser Ser Val Gly Tyr Ile Asn Pro Ser Ala
    610             615                 620
Val Asn Gln Ile Thr Asn Val Val Ala Asn Ala Met Ala Gln Val Met
625             630                 635                 640
Gly

<210> SEQ ID NO 24
<211> LENGTH: 1923
<212> TYPE: DNA
<213> ORGANISM: Artificial Sequence
<220> FEATURE:
<223> OTHER INFORMATION: Fusion protein

<400> SEQUENCE: 24
atgggcagca gcggccatca tcatcatcat catatgaact gctgcgtgaa aggcaacagc      60
atttatccgc agaaaaccag caccaaacag accggcctga tgctggatat tgcgcgccat     120
ttttatagcc cggaagtgat taaaagcttt attgatacca ttagcctgag cggcggcaac     180
tttctgcatc tgcattttag cgatcatgaa actatgcga ttgaaagcca tctgctgaac      240
cagcgcgcgg aaaacgcggt gcagggcaaa gatggcattt atattaaccc gtataccggc     300
aaaccgtttc tgagctatcg ccagctggat gatattaaag cgtatgcgaa agcgaaaggc     360
attgaactga ttccggaact ggatagcccg aaccacatga ccgcgatttt taaactggtg     420
cagaaagatc gcggcgtgaa atatctgcag ggcctgaaaa ccgccaggt ggatgatgaa      480 attgatatta ccaacgcgga tagcattacc tttatgcaga gcctgatgag cgaagtgatt     540 gatattttg cgataccag ccagcatttt catattggcg cgatgaatt tggctatagc        600 gtggaaagca ccatgaatt tattacctat gcgaacaaac tgagctattt tctggaaaaa     660
aaaggcctga aacccgcat gtggaacgat ggcctgatta aaaacacctt gaacagatt       720 aacccgaaca ttgaaattac ctattggagc tatgatggcg atacccagga taaaaacgaa    780
gcggcggaac gccgcgatat gcgcgtgagc ctgccggaac tgctggcgaa aggctttacc    840
gtgctgaact ataacagcta ttatctgtat attgtgccga aagcgagccc gacctttagc    900
caggatgcgg cgtttgcggc gaaagatgtg attaaaaact gggatctggg cgtgtgggat    960
ggccgcaaca ccaaaaaccg cgtgcagaac acccatgaaa ttgcgggcgc ggcgctgagc   1020
atttggggcg aagatgcgaa agcgctgaaa atgaaaccca ttcagaaaaa caccaaaagc   1080
ctgctggaag cggtgattca taaaaccaac ggcgatgaag cccggcggc gctgggcccg    1140 aattcaggtc aaggtggata tggtggacta ggtcaaggag gatatggaca aggtgcagga   1200
agttctgcag ccgctgccgc cgccgcagca gccgccgcag caggtggaca aggtggacaa   1260
ggtcaaggag gatatggaca aggttcagga ggttctgcag ccgccgccgc cgccgcagca   1320
gcagcagcag ctgcagcagc tggacgaggt caaggaggat atggtcaagg ttctggaggt   1380
aatgctgctg ccgcagccgc tgccgccgcc gccgccgctg cagcagccgg acagggaggt   1440
caaggtggat atggtagaca aagccaaggt gctggttccg ctgctgctgc tgctgctgct   1500
gctgccgctg ctgctgctgc aggatctgga caaggtggat acggtggaca aggtcaagga   1560
ggttatggtc agagtagtgc ttctgcttca gctgctgcgt cagctgctag tactgtagct   1620
aattcggtga gtcgcctctc atcgccttcc gcagtatctc gagtttcttc agcagtttct   1680
agcttggttt caaatggtca agtgaatatg gcagcgttac ctaatatcat ttccaacatt   1740
tcttcttctg tcagtgcatc tgctcctggt gcttctggat gtgaggtcat agtgcaagct   1800
ctactcgaag tcatcactgc tcttgttcaa atcgttagtt cttctagtgt tggatatatt   1860
```

```
aatccatctg ctgtgaacca aattactaat gttgttgcta atgccatggc tcaagtaatg    1920
ggc                                                                  1923
```

<210> SEQ ID NO 25
<211> LENGTH: 286
<212> TYPE: PRT
<213> ORGANISM: Artificial Sequence
<220> FEATURE:
<223> OTHER INFORMATION: Fusion protein

<400> SEQUENCE: 25

```
Gly Pro Asn Ser Trp Trp Trp Gly Arg Arg Pro Arg Pro
1               5                  10              15

Arg Pro Gly Pro Ala Ala Leu Gly Ser Ala Ser Gly Gln Gly Gly Tyr
            20                  25                  30

Gly Gly Leu Gly Gln Gly Gly Tyr Gly Gln Gly Ala Gly Ser Ser Ala
        35                  40                  45

Ala Ala Ala Ala Ala Ala Ala Ala Ala Ala Gly Gly Gln Gly Gly
    50                  55                  60

Gln Gly Gln Gly Gly Tyr Gly Gln Gly Ser Gly Ser Ala Ala Ala
65                  70                  75                  80

Ala Ala Ala Ala Ala Ala Ala Ala Ala Ala Gly Arg Gly Gln
                85                  90                  95

Gly Gly Tyr Gly Gln Gly Ser Gly Gly Asn Ala Ala Ala Ala Ala
                100                 105                 110

Ala Ala Ala Ala Ala Ala Ala Gly Gln Gly Gly Gln Gly Gly
            115                 120                 125

Tyr Gly Arg Gln Ser Gln Gly Ala Gly Ser Ala Ala Ala Ala Ala
130                 135                 140

Ala Ala Ala Ala Ala Ala Ala Gly Ser Gly Gln Gly Gly Tyr Gly
145                 150                 155                 160

Gly Gln Gly Gln Gly Gly Tyr Gly Gln Ser Ser Ala Ser Ala Ser Ala
                165                 170                 175

Ala Ala Ser Ala Ala Ser Thr Val Ala Asn Ser Val Ser Arg Leu Ser
            180                 185                 190

Ser Pro Ser Ala Val Ser Arg Val Ser Ser Ala Val Ser Ser Leu Val
            195                 200                 205

Ser Asn Gly Gln Val Asn Met Ala Ala Leu Pro Asn Ile Ile Ser Asn
    210                 215                 220

Ile Ser Ser Ser Val Ser Ala Ser Ala Pro Gly Ala Ser Gly Cys Glu
225                 230                 235                 240

Val Ile Val Gln Ala Leu Leu Glu Val Ile Thr Ala Leu Val Gln Ile
                245                 250                 255

Val Ser Ser Ser Ser Val Gly Tyr Ile Asn Pro Ser Ala Val Asn Gln
                260                 265                 270

Ile Thr Asn Val Val Ala Asn Ala Met Ala Gln Val Met Gly
            275                 280                 285
```

<210> SEQ ID NO 26
<211> LENGTH: 858
<212> TYPE: DNA
<213> ORGANISM: Artificial Sequence
<220> FEATURE:
<223> OTHER INFORMATION: Fusion protein

<400> SEQUENCE: 26

```
ggtccgaatt catggtggtg gtggggccgc cgcccgcgcc cgcgcccgcg cccgggcccg    60
gcggcgctgg gatccgctag cggtcaagga ggatatggtg gactaggtca aggagggtat   120
ggacaaggtg caggaagttc tgcagccgct gccgccgccg cagcagccgc cgcagcaggt   180
ggacaaggtg gacaaggtca aggaggatat ggacaaggtt caggaggttc tgcagccgcc   240
gccgccgccg cagcagcagc agcagctgca gcagctggac gaggtcaagg aggatatggc   300
caaggttctg gaggtaatgc tgctgccgca gccgctgccg ccgccgccgc cgctgcagca   360
gccggacagg gaggtcaagg tggatatggt agacaaagcc aaggtgctgg ttccgctgct   420
gctgctgctg ctgctgctgc cgctgctgct gctgcaggat ctggacaagg tggatacggt   480
ggacaaggtc aaggaggtta tggtcagagt agtgcttctg cttcagctgc tgcgtcagct   540
gctagtactg tagctaattc ggtgagtcgc ctctcatcgc cttccgcagt atctcgagtt   600
tcttcagcag tttctagctt ggtttcaaat ggtcaagtga atatggcagc gttacctaat   660
atcatttcca acatttcttc ttctgtcagt gcatctgctc ctggtgcttc tggatgtgag   720
gtcatagtgc aagctctact cgaagtcatc actgctcttg ttcaaatcgt tagttcttct   780
agtgttggat atattaatcc atctgctgtg aaccaaatta ctaatgttgt tgctaatgcc   840
atggctcaag taatgggc                                                858
```

<210> SEQ ID NO 27
<211> LENGTH: 459
<212> TYPE: PRT
<213> ORGANISM: Artificial Sequence
<220> FEATURE:
<223> OTHER INFORMATION: Fusion protein

<400> SEQUENCE: 27

```
Met Gly Ser Ser Gly His His His His His His Met Ala Ser Thr Asp
1               5                   10                  15

Tyr Trp Gln Asn Trp Thr Asp Gly Gly Gly Ile Val Asn Ala Val Asn
            20                  25                  30

Gly Ser Gly Gly Asn Tyr Ser Val Asn Trp Ser Asn Thr Gly Asn Phe
        35                  40                  45

Val Val Gly Lys Gly Trp Thr Thr Gly Ser Pro Phe Arg Thr Ile Asn
    50                  55                  60

Tyr Asn Ala Gly Val Trp Ala Pro Asn Gly Asn Gly Tyr Leu Thr Leu
65                  70                  75                  80

Tyr Gly Trp Thr Arg Ser Pro Leu Ile Glu Tyr Tyr Val Val Asp Ser
                85                  90                  95

Trp Gly Thr Tyr Arg Pro Thr Gly Thr Tyr Lys Gly Thr Val Lys Ser
            100                 105                 110

Asp Gly Gly Thr Tyr Asp Ile Tyr Thr Thr Thr Arg Tyr Asn Ala Pro
        115                 120                 125

Ser Ile Asp Gly Asp Arg Thr Thr Phe Thr Gln Tyr Trp Ser Val Arg
    130                 135                 140

Gln Ser Lys Arg Pro Thr Gly Ser Asn Ala Thr Ile Thr Phe Ser Asn
145                 150                 155                 160

His Val Asn Ala Trp Lys Ser His Gly Met Asn Leu Gly Ser Asn Trp
                165                 170                 175

Ala Tyr Gln Val Met Ala Thr Glu Gly Tyr Gln Ser Ser Gly Ser Ser
            180                 185                 190

Asn Val Thr Val Trp Pro Asn Ser Gly Gln Gly Tyr Gly Gly Leu
        195                 200                 205
```

Gly Gln Gly Gly Tyr Gly Gln Gly Ala Gly Ser Ser Ala Ala Ala Ala
            210                 215                 220

Ala Ala Ala Ala Ala Ala Ala Gly Gly Gln Gly Gly Gln Gly Gln
225                 230                 235                 240

Gly Gly Tyr Gly Gln Gly Ser Gly Gly Ser Ala Ala Ala Ala Ala
            245                 250                 255

Ala Ala Ala Ala Ala Ala Ala Ala Gly Arg Gly Gln Gly Gly Tyr
            260                 265                 270

Gly Gln Gly Ser Gly Gly Asn Ala Ala Ala Ala Ala Ala Ala Ala
            275                 280                 285

Ala Ala Ala Ala Ala Gly Gln Gly Gln Gly Gly Tyr Gly Arg
290                 295                 300

Gln Ser Gln Gly Ala Gly Ser Ala Ala Ala Ala Ala Ala Ala Ala
305                 310                 315                 320

Ala Ala Ala Ala Ala Gly Ser Gly Gln Gly Gly Tyr Gly Gln Gly
            325                 330                 335

Gln Gly Gly Tyr Gly Gln Ser Ser Ala Ser Ala Ser Ala Ala Ser
            340                 345                 350

Ala Ala Ser Thr Val Ala Asn Ser Val Ser Arg Leu Ser Ser Pro Ser
            355                 360                 365

Ala Val Ser Arg Val Ser Ser Ala Val Ser Ser Leu Val Ser Asn Gly
            370                 375                 380

Gln Val Asn Met Ala Ala Leu Pro Asn Ile Ile Ser Asn Ile Ser Ser
385                 390                 395                 400

Ser Val Ser Ala Ser Ala Pro Gly Ala Ser Gly Cys Glu Val Ile Val
                    405                 410                 415

Gln Ala Leu Leu Glu Val Ile Thr Ala Leu Val Gln Ile Val Ser Ser
                    420                 425                 430

Ser Ser Val Gly Tyr Ile Asn Pro Ser Ala Val Asn Gln Ile Thr Asn
            435                 440                 445

Val Val Ala Asn Ala Met Ala Gln Val Met Gly
    450                 455

<210> SEQ ID NO 28
<211> LENGTH: 1377
<212> TYPE: DNA
<213> ORGANISM: Artificial Sequence
<220> FEATURE:
<223> OTHER INFORMATION: Fusion protein

<400> SEQUENCE: 28
atgggcagca gcggccatca tcatcatcat catatggcta gcacagacta ctggcaaaat    60
tggactgatg ggggcggtat agtaaacgct gtcaatgggt ctggcgggaa ttacagtgtt   120
aattggtcta ataccggaaa ttttgttgtt ggtaaaggtt ggactacagg ttcgccattt   180
aggacgataa actataatgc ggagtttggc gcgccgaatg caatggata tttaacttta    240 tatggttgga cgagatcacc tctcatagaa tattatgtag tggattcatg ggtactyat    300 agacctactg gaacgtataa aggtactgta aaaagtgatg ggggtacgta tgacatatat   360
acaactacac gttataacgc accttccatt gatggcgatc gcactacttt tacgcagtac   420
tggagtgttc gccagtcgaa gagaccaacc ggaagcaacg ctacaatcac tttcagcaat   480
catgtgaacg catggaagag ccatggaatg aatctgggca gtaattgggc ttaccaagtc   540
atggcgacag aaggatatca agtagtggaa gttctaacg taacagtgtg gccgaattca   600
ggtcaaggtg gatatggtgg actaggtcaa ggaggatatg gacaaggtgc aggaagttct   660

```
gcagccgctg ccgccgccgc agcagccgcc gcagcaggtg acaaggtgg acaaggtcaa      720 ggaggatatg acaaggttc aggaggttct gcagccgccg ccgccgccgc agcagcagca      780
gcagctgcag cagctggacg aggtcaagga ggatatggtc aaggttctgg aggtaatgct      840
gctgccgcag ccgctgccgc cgccgccgcc gctgcagcag ccggacaggg aggtcaaggt      900
ggatatggta gacaaagcca aggtgctggt tccgctgctg ctgctgctgc tgctgctgcc      960
gctgctgctg ctgcaggatc tggacaaggt ggatacggtg acaaggtca aggaggttat     1020 ggtcagagta gtgcttctgc ttcagctgct gcgtcagctg ctagtactgt agctaattcg     1080
gtgagtcgcc tctcatcgcc ttccgcagta tctcgagttt cttcagcagt ttctagcttg     1140
gtttcaaatg gtcaagtgaa tatggcagcg ttacctaata tcatttccaa catttcttct     1200
tctgtcagtg catctgctcc tggtgcttct ggatgtgagg tcatagtgca agctctactc     1260
gaagtcatca ctgctcttgt tcaaatcgtt agttcttcta gtgttggata tattaatcca     1320
tctgctgtga accaaattac taatgttgtt gctaatgcca tggctcaagt aatgggc       1377
```

<210> SEQ ID NO 29
<211> LENGTH: 433
<212> TYPE: PRT
<213> ORGANISM: Artificial Sequence
<220> FEATURE:
<223> OTHER INFORMATION: Fusion protein

<400> SEQUENCE: 29

```
Met Gly Ser Ser Gly His His His His His Met Asp Pro Ser Lys
1               5                   10                  15

Asp Ser Lys Ala Gln Val Ser Ala Ala Glu Ala Gly Ile Thr Gly Thr
            20                  25                  30

Trp Tyr Asn Gln Leu Gly Ser Thr Phe Ile Val Thr Ala Gly Ala Asp
        35                  40                  45

Gly Ala Leu Thr Gly Thr Tyr Glu Ser Ala Val Gly Asn Ala Glu Ser
    50                  55                  60

Arg Tyr Thr Leu Thr Gly Arg Tyr Asp Ser Ala Pro Ala Thr Asp Gly
65                  70                  75                  80

Ser Gly Thr Ala Leu Gly Trp Arg Val Ala Trp Lys Asn Asn Tyr Arg
                85                  90                  95

Asn Ala His Ser Ala Thr Thr Trp Ser Gly Gln Tyr Val Gly Gly Ala
            100                 105                 110

Glu Ala Arg Ile Asn Thr Gln Trp Thr Leu Thr Ser Gly Thr Thr Glu
        115                 120                 125

Ala Asn Ala Trp Lys Ser Thr Leu Arg Gly His Asp Thr Phe Thr Lys
    130                 135                 140

Val Lys Pro Ser Ala Ala Ser Ile Asp Ala Ala Lys Lys Ala Gly Val
145                 150                 155                 160

Asn Asn Gly Asn Pro Leu Asp Ala Val Gln Gln Gly Asn Ser Gly Gln
                165                 170                 175

Gly Gly Tyr Gly Gly Leu Gly Gln Gly Gly Tyr Gly Gln Gly Ala Gly
            180                 185                 190

Ser Ser Ala Ala Ala Ala Ala Ala Ala Ala Ala Ala Ala Gly Gly
        195                 200                 205

Gln Gly Gly Gln Gly Gln Gly Tyr Gly Gln Gly Ser Gly Gly Ser
    210                 215                 220

Ala Ala Ala Ala Ala Ala Ala Ala Ala Ala Ala Ala Ala Ala Gly
225                 230                 235                 240
```

```
Arg Gly Gln Gly Gly Tyr Gly Gln Gly Ser Gly Gly Asn Ala Ala Ala
                245                 250                 255

Ala Ala Ala Ala Ala Ala Ala Ala Ala Ala Ala Gly Gln Gly Gly
            260                 265                 270

Gln Gly Gly Tyr Gly Arg Gln Ser Gln Gly Ala Gly Ser Ala Ala Ala
                275                 280                 285

Ala Ala Ala Ala Ala Ala Ala Ala Ala Ala Gly Ser Gly Gln Gly
            290                 295                 300

Gly Tyr Gly Gly Gln Gly Gly Gly Tyr Gly Gln Ser Ser Ala Ser
305             310                 315                 320

Ala Ser Ala Ala Ala Ser Ala Ala Ser Thr Val Ala Asn Ser Val Ser
                325                 330                 335

Arg Leu Ser Ser Pro Ser Ala Val Ser Arg Val Ser Ser Ala Val Ser
                340                 345                 350

Ser Leu Val Ser Asn Gly Gln Val Asn Met Ala Ala Leu Pro Asn Ile
                355                 360                 365

Ile Ser Asn Ile Ser Ser Ser Val Ala Ser Ala Pro Gly Ala Ser
                370                 375                 380

Gly Cys Glu Val Ile Val Gln Ala Leu Leu Glu Val Ile Thr Ala Leu
385                 390                 395                 400

Val Gln Ile Val Ser Ser Ser Val Gly Tyr Ile Asn Pro Ser Ala
                405                 410                 415

Val Asn Gln Ile Thr Asn Val Val Ala Asn Ala Met Ala Gln Val Met
                420                 425                 430

Gly
```

<210> SEQ ID NO 30
<211> LENGTH: 1299
<212> TYPE: DNA
<213> ORGANISM: Artificial Sequence
<220> FEATURE:
<223> OTHER INFORMATION: Fusion protein

<400> SEQUENCE: 30

```
atgggcagca gcggccatca tcatcatcat catatggatc cgagcaaaga tagcaaagcg      60
caggtgagcg cggcggaaag cgggcattac cggcacctggt ataaccagct gggcagcacc    120
tttattgtga ccgcgggcgc ggatggcgcg ctgaccggca cctatgaaag cgcggtgggc    180
aacgcggaaa ccgctatac cctgaccggc cgctatgata gcgcgccggc gaccgatggc      240
agcggcaccg cgctgggctg cgcgtggcg tggaaaaaca actatcgcaa cgcgcatagc      300
gcgaccacct ggagcggcca gtatgtgggc ggcgcggaag cgcgcattaa cacccagtgg    360
accctgacca cgcgcaccac cgaagcgaac cgtggaaaaa gcaccctgcg cggccatgat    420
acctttacca aagtgaaacc gagcgcggcg agcattgatg cggcgaaaaa agcgggcgtg    480
aacaacggca acccgctgga tgcggtgcag caggggaatt caggtcaagg tggatatggt    540
ggactaggtc aaggaggata tggacaaggt gcaggaagtt ctgcagccgc tgccgccgcc    600
gcagcagccg ccgcagcagg tggacaaggt ggacaaggtc aaggaggata tggacaaggt    660
tcaggaggtt ctgcagccgc cgccgccgcc gcagcagcag cagcagctgc agcagctgga    720
cgaggtcaag gaggatatgg tcaaggttct ggaggtaatg ctgctgccgc agccgctgcc    780
gccgccgccg ccgctgcagc agccggacag ggaggtcaag gtggatatgg tagacaaagc    840
caaggtgctg gttccgctgc tgctgctgct gctgctgctg ccgctgctgc tgctgcagga    900
```

```
tctggacaag gtggatacgg tggacaaggt caaggaggtt atggtcagag tagtgcttct      960
gcttcagctg ctgcgtcagc tgctagtact gtagctaatt cggtgagtcg cctctcatcg     1020
ccttccgcag tatctcgagt ttcttcagca gtttctagct tggtttcaaa tggtcaagtg     1080
aatatggcag cgttacctaa tatcatttcc aacatttctt cttctgtcag tgcatctgct     1140
cctggtgctt ctggatgtga ggtcatagtg caagctctac tcgaagtcat cactgctctt     1200
gttcaaatcg ttagttcttc tagtgttgga tatattaatc catctgctgt gaaccaaatt     1260
actaatgttg ttgctaatgc catggctcaa gtaatgggc                            1299
```

```
<210> SEQ ID NO 31
<211> LENGTH: 18
<212> TYPE: PRT
<213> ORGANISM: Euprosthenops australis

<400> SEQUENCE: 31

Ala Ser Ala Ser Ala Ala Ala Ser Ala Ala Ser Thr Val Ala Asn Ser
1               5                   10                  15
Val Ser

<210> SEQ ID NO 32
<211> LENGTH: 8
<212> TYPE: PRT
<213> ORGANISM: Euprosthenops australis

<400> SEQUENCE: 32

Ala Ser Ala Ala Ser Ala Ala Ala
1               5

<210> SEQ ID NO 33
<211> LENGTH: 8
<212> TYPE: PRT
<213> ORGANISM: Euprosthenops australis

<400> SEQUENCE: 33

Gly Ser Ala Met Gly Gln Gly Ser
1               5

<210> SEQ ID NO 34
<211> LENGTH: 5
<212> TYPE: PRT
<213> ORGANISM: Euprosthenops australis

<400> SEQUENCE: 34

Ser Ala Ser Ala Gly
1               5

<210> SEQ ID NO 35
<211> LENGTH: 5
<212> TYPE: PRT
<213> ORGANISM: Artificial Sequence
<220> FEATURE:
<223> OTHER INFORMATION: cell-binding peptide

<400> SEQUENCE: 35

Ile Lys Val Ala Val
1               5

<210> SEQ ID NO 36
<211> LENGTH: 5
<212> TYPE: PRT
<213> ORGANISM: Artificial Sequence
<220> FEATURE:
```

```
<223> OTHER INFORMATION: cell-binding peptide

<400> SEQUENCE: 36

Tyr Ile Gly Ser Arg
1               5

<210> SEQ ID NO 37
<211> LENGTH: 10
<212> TYPE: PRT
<213> ORGANISM: Artificial Sequence
<220> FEATURE:
<223> OTHER INFORMATION: cell-binding peptide
<220> FEATURE:
<221> NAME/KEY: misc_feature
<223> OTHER INFORMATION: X = any amino acid
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (7)..(9)
<223> OTHER INFORMATION: Xaa can be any naturally occurring amino acid

<400> SEQUENCE: 37

Cys Xaa Xaa Arg Gly Asp Xaa Xaa Xaa Cys
1               5                   10

<210> SEQ ID NO 38
<211> LENGTH: 100
<212> TYPE: PRT
<213> ORGANISM: Euprosthenops sp

<400> SEQUENCE: 38

Ser Arg Leu Ser Ser Pro Glu Ala Ser Ser Arg Val Ser Ser Ala Val
1               5                   10                  15

Ser Asn Leu Val Ser Ser Gly Pro Thr Asn Ser Ala Ala Leu Ser Ser
                20                  25                  30

Thr Ile Ser Asn Val Val Ser Gln Ile Gly Ala Ser Asn Pro Gly Leu
            35                  40                  45

Ser Gly Cys Asp Val Leu Val Gln Ala Leu Leu Glu Val Val Ser Ala
50                  55                  60

Leu Ile His Ile Leu Gly Ser Ser Ile Gly Gln Val Asn Tyr Gly
65                  70                  75                  80

Ser Ala Gly Gln Ala Thr Gln Leu Val Gly Gln Ser Val Tyr Gln Ala
                85                  90                  95

Leu Gly Glu Phe
            100

<210> SEQ ID NO 39
<211> LENGTH: 98
<212> TYPE: PRT
<213> ORGANISM: Euprosthenops australis

<400> SEQUENCE: 39

Ser Arg Leu Ser Ser Pro Ser Ala Val Ser Arg Val Ser Ser Ala Val
1               5                   10                  15

Ser Ser Leu Val Ser Asn Gly Gln Val Asn Met Ala Ala Leu Pro Asn
                20                  25                  30

Ile Ile Ser Asn Ile Ser Ser Ser Val Ser Ala Ser Ala Pro Gly Ala
            35                  40                  45

Ser Gly Cys Glu Val Ile Val Gln Ala Leu Leu Glu Val Ile Thr Ala
50                  55                  60
```

Leu Val Gln Ile Val Ser Ser Ser Val Gly Tyr Ile Asn Pro Ser
65                  70                  75                  80

Ala Val Asn Gln Ile Thr Asn Val Val Asn Ala Met Ala Gln Val
                85                  90                  95

Met Gly

<210> SEQ ID NO 40
<211> LENGTH: 99
<212> TYPE: PRT
<213> ORGANISM: Argiope trifasciata

<400> SEQUENCE: 40

Ser Arg Leu Ser Ser Pro Gly Ala Ala Ser Arg Val Ser Ala Val
1               5                   10                  15

Thr Ser Leu Val Ser Ser Gly Gly Pro Thr Asn Ser Ala Ala Leu Ser
                20                  25                  30

Asn Thr Ile Ser Asn Val Val Ser Gln Ile Ser Ser Ser Asn Pro Gly
                35                  40                  45

Leu Ser Gly Cys Asp Val Leu Val Gln Ala Leu Leu Glu Ile Val Ser
50                  55                  60

Ala Leu Val His Ile Leu Gly Ser Ala Asn Ile Gly Gln Val Asn Ser
65                  70                  75                  80

Ser Gly Val Gly Arg Ser Ala Ser Ile Val Gly Gln Ser Ile Asn Gln
                85                  90                  95

Ala Phe Ser

<210> SEQ ID NO 41
<211> LENGTH: 89
<212> TYPE: PRT
<213> ORGANISM: Cyrtophora moluccensis

<400> SEQUENCE: 41

Ser His Leu Ser Ser Pro Glu Ala Ser Ser Arg Val Ser Ala Val
1               5                   10                  15

Ser Asn Leu Val Ser Ser Gly Ser Thr Asn Ser Ala Ala Leu Pro Asn
                20                  25                  30

Thr Ile Ser Asn Val Val Ser Gln Ile Ser Ser Ser Asn Pro Gly Leu
                35                  40                  45

Ser Gly Cys Asp Val Leu Val Gln Ala Leu Leu Glu Val Val Ser Ala
50                  55                  60

Leu Ile His Ile Leu Gly Ser Ser Ile Gly Gln Val Asn Tyr Gly
65                  70                  75                  80

Ser Ala Gly Gln Ala Thr Gln Ile Val
                85

<210> SEQ ID NO 42
<211> LENGTH: 98
<212> TYPE: PRT
<213> ORGANISM: Latrodectus geometricus

<400> SEQUENCE: 42

Ser Ala Leu Ala Ala Pro Ala Thr Ser Ala Arg Ile Ser His Ala
1               5                   10                  15

Ser Thr Leu Leu Ser Asn Gly Pro Thr Asn Pro Ala Ser Ile Ser Asn
                20                  25                  30

Val Ile Ser Asn Ala Val Ser Gln Ile Ser Ser Ser Asn Pro Gly Ala
                35                  40                  45

-continued

```
Ser Ser Cys Asp Val Leu Val Gln Ala Leu Leu Glu Leu Val Thr Ala
        50                  55                  60

Leu Leu Thr Ile Ile Gly Ser Ser Asn Val Gly Asn Val Asn Tyr Asp
65                  70                  75                  80

Ser Ser Gly Gln Tyr Ala Gln Val Val Ser Gln Ser Val Gln Asn Ala
                85                  90                  95

Phe Val

<210> SEQ ID NO 43
<211> LENGTH: 98
<212> TYPE: PRT
<213> ORGANISM: Latrodectus hesperus

<400> SEQUENCE: 43

Ser Ala Leu Ser Ala Pro Ala Thr Ser Ala Arg Ile Ser Ser His Ala
1               5                   10                  15

Ser Ala Leu Leu Ser Ser Gly Pro Thr Asn Pro Ala Ser Ile Ser Asn
                20                  25                  30

Val Ile Ser Asn Ala Val Ser Gln Ile Ser Ser Ser Asn Pro Gly Ala
            35                  40                  45

Ser Ala Cys Asp Val Leu Val Gln Ala Leu Leu Glu Leu Val Thr Ala
        50                  55                  60

Leu Leu Thr Ile Ile Gly Ser Ser Asn Ile Gly Ser Val Asn Tyr Asp
65                  70                  75                  80

Ser Ser Gly Gln Tyr Ala Gln Val Val Thr Gln Ser Val Gln Asn Val
                85                  90                  95

Phe Gly

<210> SEQ ID NO 44
<211> LENGTH: 93
<212> TYPE: PRT
<213> ORGANISM: Macrothele holsti

<400> SEQUENCE: 44

Ser His Leu Ser Ser Pro Glu Ala Ser Ser Arg Val Ser Ser Ala Val
1               5                   10                  15

Ser Asn Leu Val Ser Gly Gly Ser Thr Asn Ser Ala Ala Leu Pro Asn
                20                  25                  30

Thr Ile Ser Asn Val Val Ser Gln Ile Ser Ser Ser Asn Pro Gly Leu
            35                  40                  45

Ser Gly Cys Asp Val Leu Val Gln Ala Leu Leu Glu Val Val Ser Ala
        50                  55                  60

Leu Ile His Ile Leu Gly Ser Ser Ser Ile Gly Gln Val Asp Tyr Gly
65                  70                  75                  80

Ser Ala Gly Gln Ala Thr Gln Ile Val Gly Gln Ser Ala
                85                  90

<210> SEQ ID NO 45
<211> LENGTH: 98
<212> TYPE: PRT
<213> ORGANISM: Nephila clavipes

<400> SEQUENCE: 45

Ser Arg Leu Ser Ser Pro Gln Ala Ser Ser Arg Val Ser Ser Ala Val
1               5                   10                  15

Ser Asn Leu Val Ala Ser Gly Pro Thr Asn Ser Ala Ala Leu Ser Ser
                20                  25                  30
```

Thr Ile Ser Asn Val Val Ser Gln Ile Gly Ala Ser Asn Pro Gly Leu
            35                  40                  45

Ser Gly Cys Asp Val Leu Ile Gln Ala Leu Leu Glu Val Val Ser Ala
    50                  55                  60

Leu Ile Gln Ile Leu Gly Ser Ser Ile Gly Gln Val Asn Tyr Gly
65                  70                  75                  80

Ser Ala Gly Gln Ala Thr Gln Ile Val Gly Gln Ser Val Tyr Gln Ala
                85                  90                  95

Leu Gly

<210> SEQ ID NO 46
<211> LENGTH: 89
<212> TYPE: PRT
<213> ORGANISM: Nephila pilipes

<400> SEQUENCE: 46

Ser Arg Leu Ser Ser Pro Glu Ala Ser Ser Arg Val Ser Ser Ala Val
1               5                   10                  15

Ser Asn Leu Val Ser Ser Gly Pro Thr Asn Ser Ala Ala Leu Ser Asn
                20                  25                  30

Thr Ile Ser Asn Val Val Ser Gln Ile Ser Ser Asn Pro Gly Leu
            35                  40                  45

Ser Gly Cys Asp Val Leu Val Gln Ala Leu Leu Glu Val Val Ser Ala
    50                  55                  60

Leu Ile His Ile Leu Gly Ser Ser Ile Gly Gln Val Asn Tyr Gly
65                  70                  75                  80

Ser Ala Gly Gln Ala Thr Gln Ile Val
                85

<210> SEQ ID NO 47
<211> LENGTH: 87
<212> TYPE: PRT
<213> ORGANISM: Nephila madagascariensis

<400> SEQUENCE: 47

Ser Arg Leu Ser Ser Pro Gln Ala Ser Ser Arg Val Ser Ser Ala Val
1               5                   10                  15

Ser Asn Leu Val Ala Ser Gly Pro Thr Asn Ser Ala Ala Leu Ser Ser
                20                  25                  30

Thr Ile Ser Asn Ala Val Ser Gln Ile Gly Ala Ser Asn Pro Gly Leu
            35                  40                  45

Ser Gly Cys Asp Val Leu Ile Gln Ala Leu Leu Glu Val Val Ser Ala
    50                  55                  60

Leu Ile His Ile Leu Gly Ser Ser Ile Gly Gln Val Asn Tyr Gly
65                  70                  75                  80

Ser Ala Gly Gln Ala Thr Gln
                85

<210> SEQ ID NO 48
<211> LENGTH: 87
<212> TYPE: PRT
<213> ORGANISM: Nephila senegalensis

<400> SEQUENCE: 48

Ser Arg Leu Ser Ser Pro Glu Ala Ser Ser Arg Val Ser Ser Ala Val
1               5                   10                  15

Ser Asn Leu Val Ser Ser Gly Pro Thr Asn Ser Ala Ala Leu Ser Ser

```
                    20                  25                  30

Thr Ile Ser Asn Val Val Ser Gln Ile Gly Ala Ser Asn Pro Gly Leu
                35                  40                  45

Ser Gly Cys Asp Val Leu Ile Gln Ala Leu Leu Glu Val Val Ser Ala
        50                  55                  60

Leu Val His Ile Leu Gly Ser Ser Ile Gly Gln Val Asn Tyr Gly
65                  70                  75                  80

Ser Ala Gly Gln Ala Thr Gln
                85

<210> SEQ ID NO 49
<211> LENGTH: 89
<212> TYPE: PRT
<213> ORGANISM: Octonoba varians

<400> SEQUENCE: 49

Ser Arg Leu Ser Ser Pro Glu Ala Ser Ser Arg Val Ser Ser Ala Val
1               5                   10                  15

Ser Asn Leu Val Ser Ser Gly Pro Thr Asn Ser Ala Ala Leu Ser Asn
                20                  25                  30

Thr Ile Ser Asn Val Val Ser Gln Ile Ser Ser Asn Pro Gly Leu
                35                  40                  45

Ser Gly Cys Asp Val Leu Val Gln Ala Leu Leu Glu Val Val Ser Ala
        50                  55                  60

Pro Ile His Ile Leu Gly Ser Ser Ile Gly Gln Val Asn Tyr Gly
65                  70                  75                  80

Ser Ala Gly Gln Ala Thr Gln Ile Val
                85

<210> SEQ ID NO 50
<211> LENGTH: 89
<212> TYPE: PRT
<213> ORGANISM: Psechrus sinensis

<400> SEQUENCE: 50

Ser Arg Leu Ser Ser Pro Glu Ala Ser Ser Arg Val Ser Ser Ala Val
1               5                   10                  15

Ser Asn Leu Val Ser Ser Gly Pro Thr Asn Ser Ala Ala Leu Pro Asn
                20                  25                  30

Thr Ile Ser Asn Val Val Ser Gln Ile Ser Ser Asn Pro Gly Leu
                35                  40                  45

Ser Gly Cys Asp Val Leu Val Gln Ala Leu Leu Glu Val Val Ser Ala
        50                  55                  60

Leu Ile His Ile Leu Gly Ser Ser Ile Gly Gln Val Asn Tyr Gly
65                  70                  75                  80

Ser Ala Gly Gln Ala Thr Gln Ile Val
                85

<210> SEQ ID NO 51
<211> LENGTH: 88
<212> TYPE: PRT
<213> ORGANISM: Tetragnatha kauaiensis

<400> SEQUENCE: 51

Ser Leu Leu Ser Ser Pro Ala Ser Asn Ala Arg Ile Ser Ser Ala Val
1               5                   10                  15

Ser Ala Leu Ala Ser Gly Ala Ala Ser Gly Pro Gly Tyr Leu Ser Ser
                20                  25                  30
```

```
Val Ile Ser Asn Val Val Ser Gln Val Ser Ser Asn Ser Gly Gly Leu
        35                  40                  45

Val Gly Cys Asp Thr Leu Val Gln Ala Leu Leu Glu Ala Ala Ala Ala
 50                  55                  60

Leu Val His Val Leu Ala Ser Ser Ser Gly Gly Gln Val Asn Leu Asn
65                  70                  75                  80

Thr Ala Gly Tyr Thr Ser Gln Leu
                85

<210> SEQ ID NO 52
<211> LENGTH: 88
<212> TYPE: PRT
<213> ORGANISM: Tetragnatha versicolor

<400> SEQUENCE: 52

Ser Arg Leu Ser Ser Pro Ala Ser Asn Ala Arg Ile Ser Ser Ala Val
1               5                   10                  15

Ser Ala Leu Ala Ser Gly Gly Ala Ser Ser Pro Gly Tyr Leu Ser Ser
                20                  25                  30

Ile Ile Ser Asn Val Val Ser Gln Val Ser Ser Asn Asn Asp Gly Leu
        35                  40                  45

Ser Gly Cys Asp Thr Val Val Gln Ala Leu Leu Glu Val Ala Ala Ala
 50                  55                  60

Leu Val His Val Leu Ala Ser Ser Asn Ile Gly Gln Val Asn Leu Asn
65                  70                  75                  80

Thr Ala Gly Tyr Thr Ser Gln Leu
                85

<210> SEQ ID NO 53
<211> LENGTH: 89
<212> TYPE: PRT
<213> ORGANISM: Araneus bicentenarius

<400> SEQUENCE: 53

Ser Arg Leu Ser Ser Ser Ala Ala Ser Ser Arg Val Ser Ser Ala Val
1               5                   10                  15

Ser Ser Leu Val Ser Ser Gly Pro Thr Thr Pro Ala Ala Leu Ser Asn
                20                  25                  30

Thr Ile Ser Ser Ala Val Ser Gln Ile Ser Ala Ser Asn Pro Gly Leu
        35                  40                  45

Ser Gly Cys Asp Val Leu Val Gln Ala Leu Leu Glu Val Val Ser Ala
 50                  55                  60

Leu Val His Ile Leu Gly Ser Ser Val Gly Gln Ile Asn Tyr Gly
65                  70                  75                  80

Ala Ser Ala Gln Tyr Ala Gln Met Val
                85

<210> SEQ ID NO 54
<211> LENGTH: 97
<212> TYPE: PRT
<213> ORGANISM: Argiope amoena

<400> SEQUENCE: 54

Arg Leu Ser Ser Pro Gln Ala Ser Ser Arg Val Ser Ser Ala Val Ser
1               5                   10                  15

Thr Leu Val Ser Ser Gly Pro Thr Asn Pro Ala Ser Leu Ser Asn Ala
                20                  25                  30
```

Ile Gly Ser Val Val Ser Gln Val Ser Ala Ser Asn Pro Gly Leu Pro
        35                  40                  45

Ser Cys Asp Val Leu Val Gln Ala Leu Leu Glu Ile Val Ser Ala Leu
 50                  55                  60

Val His Ile Leu Gly Ser Ser Ile Gly Gln Ile Asn Tyr Ser Ala
 65                  70                  75                  80

Ser Ser Gln Tyr Ala Arg Leu Val Gly Gln Ser Ile Ala Gln Ala Leu
                 85                  90                  95

Gly

<210> SEQ ID NO 55
<211> LENGTH: 82
<212> TYPE: PRT
<213> ORGANISM: Argiope aurantia

<400> SEQUENCE: 55

Ser Arg Leu Ser Ser Pro Gln Ala Ser Ser Arg Val Ser Ser Ala Val
1                5                  10                  15

Ser Thr Leu Val Ser Ser Gly Pro Thr Asn Pro Ala Ala Leu Ser Asn
                20                  25                  30

Ala Ile Ser Ser Val Val Ser Gln Val Ser Ala Ser Asn Pro Gly Leu
            35                  40                  45

Ser Gly Cys Asp Val Leu Val Gln Ala Leu Leu Glu Leu Val Ser Ala
         50                  55                  60

Leu Val His Ile Leu Gly Ser Ser Ile Gly Gln Ile Asn Tyr Ala
 65                  70                  75                  80

Ala Ser

<210> SEQ ID NO 56
<211> LENGTH: 98
<212> TYPE: PRT
<213> ORGANISM: Argiope trifasciata

<400> SEQUENCE: 56

Ser Arg Leu Ser Ser Pro Gln Ala Ser Ser Arg Val Ser Ser Ala Val
1                5                  10                  15

Ser Thr Leu Val Ser Ser Gly Pro Thr Asn Pro Ala Ser Leu Ser Asn
                20                  25                  30

Ala Ile Ser Ser Val Val Ser Gln Val Ser Ser Ser Asn Pro Gly Leu
            35                  40                  45

Ser Gly Cys Asp Val Leu Val Gln Ala Leu Leu Glu Ile Val Ser Ala
         50                  55                  60

Leu Val His Ile Leu Gly Ser Ser Ile Gly Gln Ile Asn Tyr Ala
 65                  70                  75                  80

Ala Ser Ser Gln Tyr Ala Gln Leu Val Gly Gln Ser Leu Thr Gln Ala
                 85                  90                  95

Leu Gly

<210> SEQ ID NO 57
<211> LENGTH: 89
<212> TYPE: PRT
<213> ORGANISM: Gasteracantha mammosa

<400> SEQUENCE: 57

Ser Arg Leu Ser Ser Pro Gln Ala Gly Ala Arg Val Ser Ser Ala Val
1                5                  10                  15

Ser Ala Leu Val Ala Ser Gly Pro Thr Ser Pro Ala Ala Val Ser Ser

```
                 20                  25                  30

Ala Ile Ser Asn Val Ala Ser Gln Ile Ser Ala Ser Asn Pro Gly Leu
             35                  40                  45

Ser Gly Cys Asp Val Leu Val Gln Ala Leu Leu Glu Ile Val Ser Ala
         50                  55                  60

Leu Val Ser Ile Leu Ser Ser Ala Ser Ile Gly Gln Ile Asn Tyr Gly
 65                  70                  75                  80

Ala Ser Gly Gln Tyr Ala Ala Met Ile
                 85
```

<210> SEQ ID NO 58
<211> LENGTH: 90
<212> TYPE: PRT
<213> ORGANISM: Latrodectus geometricus

<400> SEQUENCE: 58

```
Ser Ala Leu Ser Ser Pro Thr Thr His Ala Arg Ile Ser Ser His Ala
 1               5                  10                  15

Ser Thr Leu Leu Ser Ser Gly Pro Thr Asn Ser Ala Ala Ile Ser Asn
             20                  25                  30

Val Ile Ser Asn Ala Val Ser Gln Val Ser Ala Ser Asn Pro Gly Ser
             35                  40                  45

Ser Ser Cys Asp Val Leu Val Gln Ala Leu Leu Glu Leu Ile Thr Ala
         50                  55                  60

Leu Ile Ser Ile Val Asp Ser Ser Asn Ile Gly Gln Val Asn Tyr Gly
 65                  70                  75                  80

Ser Ser Gly Gln Tyr Ala Gln Met Val Gly
                 85                  90
```

<210> SEQ ID NO 59
<211> LENGTH: 98
<212> TYPE: PRT
<213> ORGANISM: Latrodectus hesperus

<400> SEQUENCE: 59

```
Ser Ala Leu Ser Ser Pro Thr Thr His Ala Arg Ile Ser Ser His Ala
 1               5                  10                  15

Ser Thr Leu Leu Ser Ser Gly Pro Thr Asn Ala Ala Ala Leu Ser Asn
             20                  25                  30

Val Ile Ser Asn Ala Val Ser Gln Val Ser Ala Ser Asn Pro Gly Ser
             35                  40                  45

Ser Ser Cys Asp Val Leu Val Gln Ala Leu Leu Glu Ile Ile Thr Ala
         50                  55                  60

Leu Ile Ser Ile Leu Asp Ser Ser Ser Val Gly Gln Val Asn Tyr Gly
 65                  70                  75                  80

Ser Ser Gly Gln Tyr Ala Gln Ile Val Gly Gln Ser Met Gln Gln Ala
                 85                  90                  95

Met Gly
```

<210> SEQ ID NO 60
<211> LENGTH: 97
<212> TYPE: PRT
<213> ORGANISM: Nephila clavipes

<400> SEQUENCE: 60

```
Ser Arg Leu Ala Ser Pro Asp Ser Gly Ala Arg Val Ala Ser Ala Val
 1               5                  10                  15
```

```
Ser Asn Leu Val Ser Ser Gly Pro Thr Ser Ser Ala Ala Leu Ser Ser
            20                  25                  30

Val Ile Ser Asn Ala Val Ser Gln Ile Gly Ala Ser Asn Pro Gly Leu
        35                  40                  45

Ser Gly Cys Asp Val Leu Ile Gln Ala Leu Leu Glu Ile Val Ser Ala
    50                  55                  60

Cys Val Thr Ile Leu Ser Ser Ser Ile Gly Gln Val Asn Tyr Gly
65                  70                  75                  80

Ala Ala Ser Gln Phe Ala Gln Val Gly Gln Ser Val Leu Ser Ala
                85                  90                  95

Phe
```

<210> SEQ ID NO 61
<211> LENGTH: 82
<212> TYPE: PRT
<213> ORGANISM: Nephila madagascariensis

<400> SEQUENCE: 61

```
Ser Arg Leu Ala Ser Pro Asp Ser Gly Ala Arg Val Ala Ser Ala Val
1               5                   10                  15

Ser Asn Leu Val Ser Ser Gly Pro Thr Ser Ser Ala Ala Leu Ser Ser
            20                  25                  30

Val Ile Ser Asn Ala Val Ser Gln Ile Gly Ala Ser Asn Pro Gly Leu
        35                  40                  45

Ser Gly Cys Asp Val Leu Ile Gln Ala Leu Leu Glu Ile Val Ser Ala
    50                  55                  60

Cys Val Thr Ile Leu Ser Ser Ser Ile Gly Gln Val Asn Tyr Gly
65                  70                  75                  80

Ala Ala
```

<210> SEQ ID NO 62
<211> LENGTH: 82
<212> TYPE: PRT
<213> ORGANISM: Nephila senegalensis
<220> FEATURE:
<221> NAME/KEY: misc_feature
<222> LOCATION: (35)..(35)
<223> OTHER INFORMATION: Xaa can be any naturally occurring amino acid
<220> FEATURE:
<221> NAME/KEY: misc_feature
<222> LOCATION: (56)..(56)
<223> OTHER INFORMATION: Xaa can be any naturally occurring amino acid

<400> SEQUENCE: 62

```
Ser Arg Leu Ala Ser Pro Asp Ser Gly Ala Arg Val Ala Ser Ala Val
1               5                   10                  15

Ser Asn Leu Val Ser Ser Gly Pro Thr Ser Ser Ala Ala Leu Ser Ser
            20                  25                  30

Val Ile Xaa Asn Ala Val Ser Gln Ile Gly Ala Ser Asn Pro Gly Leu
        35                  40                  45

Ser Gly Cys Asp Val Leu Ile Xaa Ala Leu Leu Glu Ile Val Ser Ala
    50                  55                  60

Cys Val Thr Ile Leu Ser Ser Ser Ile Gly Gln Val Asn Tyr Gly
65                  70                  75                  80

Ala Ala
```

<210> SEQ ID NO 63
<211> LENGTH: 71
<212> TYPE: PRT

-continued

<213> ORGANISM: Dolomedes tenebrosus

<400> SEQUENCE: 63

Ser Arg Leu Ser Ser Pro Glu Ala Ala Ser Arg Val Ser Ser Ala Val
1               5                   10                  15

Ser Ser Leu Val Ser Asn Gly Gln Val Asn Val Asp Ala Leu Pro Ser
            20                  25                  30

Ile Ile Ser Asn Leu Ser Ser Ser Ile Ser Ala Ser Ala Thr Thr Ala
        35                  40                  45

Ser Asp Cys Glu Val Leu Val Gln Val Leu Leu Glu Val Val Ser Ala
    50                  55                  60

Leu Val Gln Ile Val Cys Ser
65                  70

<210> SEQ ID NO 64
<211> LENGTH: 97
<212> TYPE: PRT
<213> ORGANISM: Dolomedes tenebrosus

<400> SEQUENCE: 64

Ser Arg Leu Ser Ser Pro Gln Ala Ala Ser Arg Val Ser Ser Ala Val
1               5                   10                  15

Ser Ser Leu Val Ser Asn Gly Gln Val Asn Val Ala Ala Leu Pro Ser
            20                  25                  30

Ile Ile Ser Ser Leu Ser Ser Ser Ile Ser Ala Ser Ser Thr Ala Ala
        35                  40                  45

Ser Asp Cys Glu Val Leu Val Gln Val Leu Leu Glu Ile Val Ser Ala
    50                  55                  60

Leu Val Gln Ile Val Ser Ser Ala Asn Val Gly Tyr Ile Asn Pro Glu
65                  70                  75                  80

Ala Ser Gly Ser Leu Asn Ala Val Gly Ser Ala Leu Ala Ala Ala Met
                85                  90                  95

Gly

<210> SEQ ID NO 65
<211> LENGTH: 93
<212> TYPE: PRT
<213> ORGANISM: Araneus diadematus

<400> SEQUENCE: 65

Asn Arg Leu Ser Ser Ala Gly Ala Ala Ser Arg Val Ser Ser Asn Val
1               5                   10                  15

Ala Ala Ile Ala Ser Ala Gly Ala Ala Ala Leu Pro Asn Val Ile Ser
            20                  25                  30

Asn Ile Tyr Ser Gly Val Leu Ser Ser Gly Val Ser Ser Ser Glu Ala
        35                  40                  45

Leu Ile Gln Ala Leu Leu Glu Val Ile Ser Ala Leu Ile His Val Leu
    50                  55                  60

Gly Ser Ala Ser Ile Gly Asn Val Ser Ser Val Gly Val Asn Ser Ala
65                  70                  75                  80

Leu Asn Ala Val Gln Asn Ala Val Gly Ala Tyr Ala Gly
                85                  90

<210> SEQ ID NO 66
<211> LENGTH: 98
<212> TYPE: PRT
<213> ORGANISM: Araneus diadematus

```
<400> SEQUENCE: 66

Ser Arg Leu Ser Ser Pro Ser Ala Ala Arg Val Ser Ser Ala Val
1               5                   10                  15

Ser Leu Val Ser Asn Gly Gly Pro Thr Ser Pro Ala Ala Leu Ser Ser
            20                  25                  30

Ser Ile Ser Asn Val Val Ser Gln Ile Ser Ala Ser Asn Pro Gly Leu
            35                  40                  45

Ser Gly Cys Asp Ile Leu Val Gln Ala Leu Leu Glu Ile Ile Ser Ala
        50                  55                  60

Leu Val His Ile Leu Gly Ser Ala Asn Ile Gly Pro Val Asn Ser Ser
65                  70                  75                  80

Ser Ala Gly Gln Ser Ala Ser Ile Val Gly Gln Ser Val Tyr Arg Ala
                85                  90                  95

Leu Ser

<210> SEQ ID NO 67
<211> LENGTH: 98
<212> TYPE: PRT
<213> ORGANISM: Araneus diadematus

<400> SEQUENCE: 67

Ser Arg Leu Ser Ser Pro Ala Ala Ser Ser Arg Val Ser Ser Ala Val
1               5                   10                  15

Ser Ser Leu Val Ser Ser Gly Pro Thr Lys His Ala Ala Leu Ser Asn
            20                  25                  30

Thr Ile Ser Ser Val Val Ser Gln Val Ser Ala Ser Asn Pro Gly Leu
            35                  40                  45

Ser Gly Cys Asp Val Leu Val Gln Ala Leu Leu Glu Val Val Ser Ala
        50                  55                  60

Leu Val Ser Ile Leu Gly Ser Ser Ser Ile Gly Gln Ile Asn Tyr Gly
65                  70                  75                  80

Ala Ser Ala Gln Tyr Thr Gln Met Val Gly Ser Val Ala Gln Ala
                85                  90                  95

Leu Ala

<210> SEQ ID NO 68
<211> LENGTH: 94
<212> TYPE: PRT
<213> ORGANISM: Araneus diadematus

<400> SEQUENCE: 68

Ser Val Tyr Leu Arg Leu Gln Pro Arg Leu Glu Val Ser Ser Ala Val
1               5                   10                  15

Ser Ser Leu Val Ser Ser Gly Pro Thr Asn Gly Ala Ala Val Ser Gly
            20                  25                  30

Ala Leu Asn Ser Leu Val Ser Gln Ile Ser Ala Ser Asn Pro Gly Leu
            35                  40                  45

Ser Gly Cys Asp Ala Leu Val Gln Ala Leu Leu Glu Leu Val Ser Ala
        50                  55                  60

Leu Val Ala Ile Leu Ser Ser Ala Ser Ile Gly Gln Val Asn Val Ser
65                  70                  75                  80

Ser Val Ser Gln Ser Thr Gln Met Ile Ser Gln Ala Leu Ser
                85                  90

<210> SEQ ID NO 69
<211> LENGTH: 93
```

```
<212> TYPE: PRT
<213> ORGANISM: Araneus ventricosus

<400> SEQUENCE: 69

Asn Arg Leu Ser Ser Ala Glu Ala Ala Ser Arg Val Ser Ser Asn Ile
1               5                   10                  15

Ala Ala Ile Ala Ser Gly Gly Ala Ser Ala Leu Pro Ser Val Ile Ser
            20                  25                  30

Asn Ile Tyr Ser Gly Val Val Ala Ser Gly Val Ser Ser Asn Glu Ala
        35                  40                  45

Leu Ile Gln Ala Leu Leu Glu Leu Leu Ser Ala Leu Val His Val Leu
    50                  55                  60

Ser Ser Ala Ser Ile Gly Asn Val Ser Val Gly Val Asp Ser Thr
65                  70                  75                  80

Leu Asn Val Val Gln Asp Ser Val Gly Gln Tyr Val Gly
                85                  90

<210> SEQ ID NO 70
<211> LENGTH: 272
<212> TYPE: PRT
<213> ORGANISM: Artificial Sequence
<220> FEATURE:
<223> OTHER INFORMATION: Fusion protein

<400> SEQUENCE: 70

Gly Pro Asn Ser Cys Thr Gly Arg Gly Asp Ser Pro Ala Cys Gly Ser
1               5                   10                  15

Ala Ser Gly Gln Gly Gly Tyr Gly Gly Leu Gly Gln Gly Gly Tyr Gly
            20                  25                  30

Gln Gly Ala Gly Ser Ser Ala Ala Ala Ala Ala Ala Ala Ala Ala
        35                  40                  45

Ala Ala Gly Gly Gln Gly Gly Gln Gly Gln Gly Gly Tyr Gly Gln Gly
    50                  55                  60

Ser Gly Gly Ser Ala Ala Ala Ala Ala Ala Ala Ala Ala Ala Ala Ala
65                  70                  75                  80

Ala Ala Ala Gly Arg Gly Gln Gly Gly Tyr Gly Gln Gly Ser Gly Gly
                85                  90                  95

Asn Ala Ala Ala Ala Ala Ala Ala Ala Ala Ala Ala Ala Ala
            100                 105                 110

Gly Gln Gly Gly Gln Gly Gly Tyr Gly Arg Gln Ser Gln Gly Ala Gly
        115                 120                 125

Ser Ala Ala Ala Ala Ala Ala Ala Ala Ala Ala Ala Gly
    130                 135                 140

Ser Gly Gln Gly Gly Tyr Gly Gly Gln Gly Gln Gly Tyr Gly Gln
145                 150                 155                 160

Ser Ser Ala Ser Ala Ser Ala Ala Ser Ala Ala Gly Ser Tyr Ala
                165                 170                 175

Gly Ala Val Asn Arg Leu Ser Ser Ala Glu Ala Ala Ser Arg Val Ser
            180                 185                 190

Ser Asn Ile Ala Ala Ile Ala Ser Gly Gly Ala Ser Ala Leu Pro Ser
        195                 200                 205

Val Ile Ser Asn Ile Tyr Ser Gly Val Val Ala Ser Gly Val Ser Ser
    210                 215                 220

Asn Glu Ala Leu Ile Gln Ala Leu Leu Glu Leu Leu Ser Ala Leu Val
225                 230                 235                 240

His Val Leu Ser Ser Ala Ser Ile Gly Asn Val Ser Ser Val Gly Val
```

```
                245                 250                 255
Asp Ser Thr Leu Asn Val Val Gln Asp Ser Val Gly Gln Tyr Val Gly
            260                 265                 270

<210> SEQ ID NO 71
<211> LENGTH: 151
<212> TYPE: PRT
<213> ORGANISM: Euprosthenops australis

<400> SEQUENCE: 71

Gly Ser Gly Asn Ser Gly Ile Gln Gly Gln Gly Gly Tyr Gly Gly Leu
1               5                   10                  15

Gly Gln Gly Gly Tyr Gly Gln Gly Ala Gly Ser Ser Ala Ala Ala Ala
            20                  25                  30

Ala Ala Ala Ala Ala Ala Ala Ala Gly Gly Gln Gly Gly Gln Gly Gln
        35                  40                  45

Gly Gly Tyr Gly Gln Gly Ser Gly Ser Ala Ala Ala Ala Ala Ala Ala
    50                  55                  60

Ala Ala Ala Ala Ala Ala Ala Gly Arg Gly Gln Gly Gly Tyr
65                  70                  75                  80

Gly Gln Gly Ser Gly Asn Ala Ala Ala Ala Ala Ala Ala Ala
            85                  90                  95

Ala Ala Ala Ala Ala Gly Gln Gly Gly Gln Gly Gly Tyr Gly Arg
        100                 105                 110

Gln Ser Gln Gly Ala Gly Ser Ala Ala Ala Ala Ala Ala Ala Ala
        115                 120                 125

Ala Ala Ala Ala Gly Ser Gly Gln Gly Gly Tyr Gly Gly Gln Gly
    130                 135                 140

Gln Gly Gly Tyr Gly Gln Ser
145                 150

<210> SEQ ID NO 72
<211> LENGTH: 270
<212> TYPE: PRT
<213> ORGANISM: Artificial Sequence
<220> FEATURE:
<223> OTHER INFORMATION: Fusion protein

<400> SEQUENCE: 72

Gly Pro Asn Ser Arg Gly Asp Ala Gly Ala Ser Gly Gln Gly Gly
1               5                   10                  15

Tyr Gly Gly Leu Gly Gln Gly Gly Tyr Gly Gln Gly Ala Gly Ser Ser
            20                  25                  30

Ala Ala Ala Ala Ala Ala Ala Ala Ala Ala Gly Gln Gly Gly
        35                  40                  45

Gln Gly Gln Gly Gly Tyr Gly Gln Gly Ser Gly Ser Ala Ala Ala
    50                  55                  60

Ala Ala Ala Ala Ala Ala Ala Ala Ala Ala Gly Arg Gly Gln
65                  70                  75                  80

Gly Gly Tyr Gly Gln Gly Ser Gly Asn Ala Ala Ala Ala Ala
            85                  90                  95

Ala Ala Ala Ala Ala Ala Ala Gly Gln Gly Gly Gln Gly Gly
        100                 105                 110

Tyr Gly Arg Gln Ser Gln Gly Ala Gly Ser Ala Ala Ala Ala Ala
        115                 120                 125

Ala Ala Ala Ala Ala Ala Ala Gly Ser Gly Gln Gly Gly Tyr Gly
    130                 135                 140
```

-continued

```
Gly Gln Gly Gln Gly Gly Tyr Gly Gln Ser Ser Ala Ser Ala Ser Ala
145                 150                 155                 160

Ala Ala Ser Ala Ala Ser Thr Val Ala Asn Ser Val Ser Arg Leu Ser
            165                 170                 175

Ser Pro Ser Ala Val Ser Arg Val Ser Ser Ala Val Ser Ser Leu Val
            180                 185                 190

Ser Asn Gly Gln Val Asn Met Ala Ala Leu Pro Asn Ile Ile Ser Asn
        195                 200                 205

Ile Ser Ser Ser Val Ser Ala Ser Ala Pro Gly Ala Ser Gly Cys Glu
        210                 215                 220

Val Ile Val Gln Ala Leu Leu Glu Val Ile Thr Ala Leu Val Gln Ile
225                 230                 235                 240

Val Ser Ser Ser Ser Val Gly Tyr Ile Asn Pro Ser Ala Val Asn Gln
                245                 250                 255

Ile Thr Asn Val Val Ala Asn Ala Met Ala Gln Val Met Gly
            260                 265                 270
```

SPIDER SILK COATING OF SOLID SURFACES

CROSS-REFERENCE TO RELATED APPLICATIONS

The present application is a national phase under 35 U.S.C. § 371 of PCT International Application No. PCT/EP2017/061712, which has an International filing date of May 16, 2017, which claims priority of Application No. 16169789.1 filed in Europe on May 16, 2016, and Application No. 16192443.6 filed in Europe on Oct. 5, 2016, under 35 U.S.C. § 119, the entire contents of which are hereby incorporated by reference and for which priority is claimed under 35 U.S.C. § 120.

TECHNICAL FIELD OF THE INVENTION

The present invention relates to the field of surface chemistry, and more specifically to coating of surfaces, e.g. surface-coated medical devices and scientific tools. The invention provides a method for coating a solid surface with a recombinant spider silk protein, and a solid surface coated with a recombinant spider silk protein.

BACKGROUND TO THE INVENTION

Implants are widely used for orthopaedic applications such as fixing fractures, spinal reconstruction, and soft tissue anchorage. Hard implants such as tooth and hip implants are associated with a risk of implant failure. This can be due to infections or foreign body responses from the immune system that leads to encapsulation and rejection of the implant. For instance, infections of orthopaedic fracture and reconstructive devices occur in approximately 5% of cases and total about 100,000 cases per year in the USA alone.

Implant infections are not only a consequence of host factors and surgical technique. The anatomical site and characteristics of the implanted device including size, shape, material, topography and intended use are important variables. Several methods to coat the implant directly with antibiotics or other biomolecules in order to enhance osseointegration and mitigate adverse events associated with the foreign body response or infection have been suggested, se e.g. S B Goodman et al., Biomaterials 34(13): 3184-3183 (2013). It is of great interest to pre-coat the implants with a material that can enhance the acceptance of the implant to the body and reduce the risk of infections.

However, given that most implant surfaces are hydrophobic and neutrally charged, coating implants by simple absorption of biomolecules, such as short peptides, is often inefficient, which has resulted in evolvement of complicated and time-consuming methods for introducing charges to the implant surface and creation of numerous layers of coating on the implant surface. For instance, layer-by-layer (LBL) coating methods have been developed, which involve dipping implants repeatedly in polyelectrolyte solutions with opposite charges, followed by deposition of growth factors, such as BMP-2. A LBL coating method has also been used to sequentially deposit hydroxyapatite and BMP-2. Hydroxyapatite formed the base layers, while BMP-2 was presented in the outermost layers. However, most current LBL approaches require the use of a few hundred layers to avoid a burst release of the biomolecules; thus the LBL method is labor intensive, costly, and may lead to batch-to-batch variability. Second, the LBL coating process is often performed using acidic solutions for effective loading, which is not biomolecule friendly.

G. Vidal et al., Acta Biomaterialia, 9(1), 4935-4943 (2013) has reported chemical grafting of a silk fibroin protein from the silkworm *Bombyx mori* to a titanium surface via a titanium binding peptide (TiBP). After an initial adsorption phase of protein-to-surface interactions, the protein adsorption stagnates and essentially no further fibroin is attached. The resulting product is thus consisting of a fibroin surface monolayer grafted onto a titanium surface via a TiBP. Notably, a fraction of the adsorbed proteins is washed away during the buffer flow, implying that the chemically grafted silkworm coating is not stable.

Films of recombinant spider silk proteins having a thickness of 1-2 μm have previously been achieved by air-drying, see e.g. WO 2012/055854 A1. This air-drying method is time-consuming, and the resulting films are only loosely attached to the underlying surface, which means that they may easily fall off the surface, e.g. during washing conditions which are required for pre-conditioning or sterilization of the coatings. Other drawbacks of the air-drying method is that the resulting surface is rather uneven, resulting in lower reproducibility for certain applications, and rigid, i.e. has a low viscosity due to a low water content. Moreover, air-drying into films is limited to simpler open and flat surfaces.

P. H. Zeplin et al., Adv. Funct. Mater. 24: 2658-2666 (2014) discloses the formation of a micrometer film of a spider silk protein on a silicone surface by dip coating. The silicone items were dipped into a silk solution and air-dried several times and then subjected to a fixation step. This comparably complicated protocol produces rather thick films, typically between 1 and 6 μm, which inhibit cell proliferation and differentiation. The films are suggested for use as bioshields.

US 2011/0230911 discloses the formation of thick films (0.5-1.5 μm) of a spider silk protein on polystyrene and glass surfaces by dissolving the protein in a harsh organic solvent (HFIP), air-drying the HFIP solution onto the surfaces, followed by a fixation step.

Despite advances in the field, there is still a need for simple and effective methods for coating implant surfaces and other solid surfaces. There is also a need for new coatings for implants and other solid surfaces, which can be applied by simple and effective methods and which provide attractive properties to the coated surface.

SUMMARY OF THE INVENTION

It is an object of the present invention to provide a simple and effective method for coating implant surfaces and other solid surfaces with biomolecules.

It is also an object of the present invention to provide a method for coating implant surfaces and other solid surfaces with biomolecules, which can be performed in aqueous solvents having a physiological pH.

It is one object of the present invention to provide a method for stable coating of implant surfaces and other solid surfaces with biomolecules without covalent bonds between the implant surface and the coating.

It is a further object of the present invention to provide a solid surface stably coated with a biomolecule without covalent bonds between the implant surface and the coating.

It is an object of the present invention to provide a solid surface stably coated with a biomolecule, which sufficient stability to allow for pre-conditioning and sterilization of the coating.

It is an object of the present invention to provide a solid surface stably coated with a thin, nano-sized film.

It is a further object of the present invention to provide a solid surface stably coated with a nano-sized film containing a biomolecule.

It is a further object of the present invention to coat all types of surface shapes with a biomolecule.

For these and other objects that will be evident from the following disclosure, the present invention provides according to a first aspect a method for coating a solid surface according to the appended claims and as presented herein.

The present invention further provides according to a second aspect a coated solid surface according to the appended claims and as presented herein.

BRIEF DESCRIPTION OF THE DRAWINGS

FIG. 3 shows an assessment of the viscoelastic properties of the recombinant spider silk protein coatings according to the invention.

FIG. 6 shows assembly of functionalized spider silk protein coatings onto titanium and stainless steel.

FIG. 7 illustrate cell viability on functionalized spider silk protein coatings.

FIG. 8 shows adsorption behavior of functionalized spider silk protein onto gold and $SiO_2$ surfaces and demonstrates retained functionality.

FIG. 10 shows a sequence alignment of spidroin C-terminal domains.

FIG. 11 shows growth curves and micrographs of primary cells growing on functionalized spider silk protein coatings.

FIG. 12 shows (A) adsorption behavior of a recombinant spider silk protein to a gold surface, and (B) the resulting surface topography.

LIST OF APPENDED SEQUENCES

Figure 1:
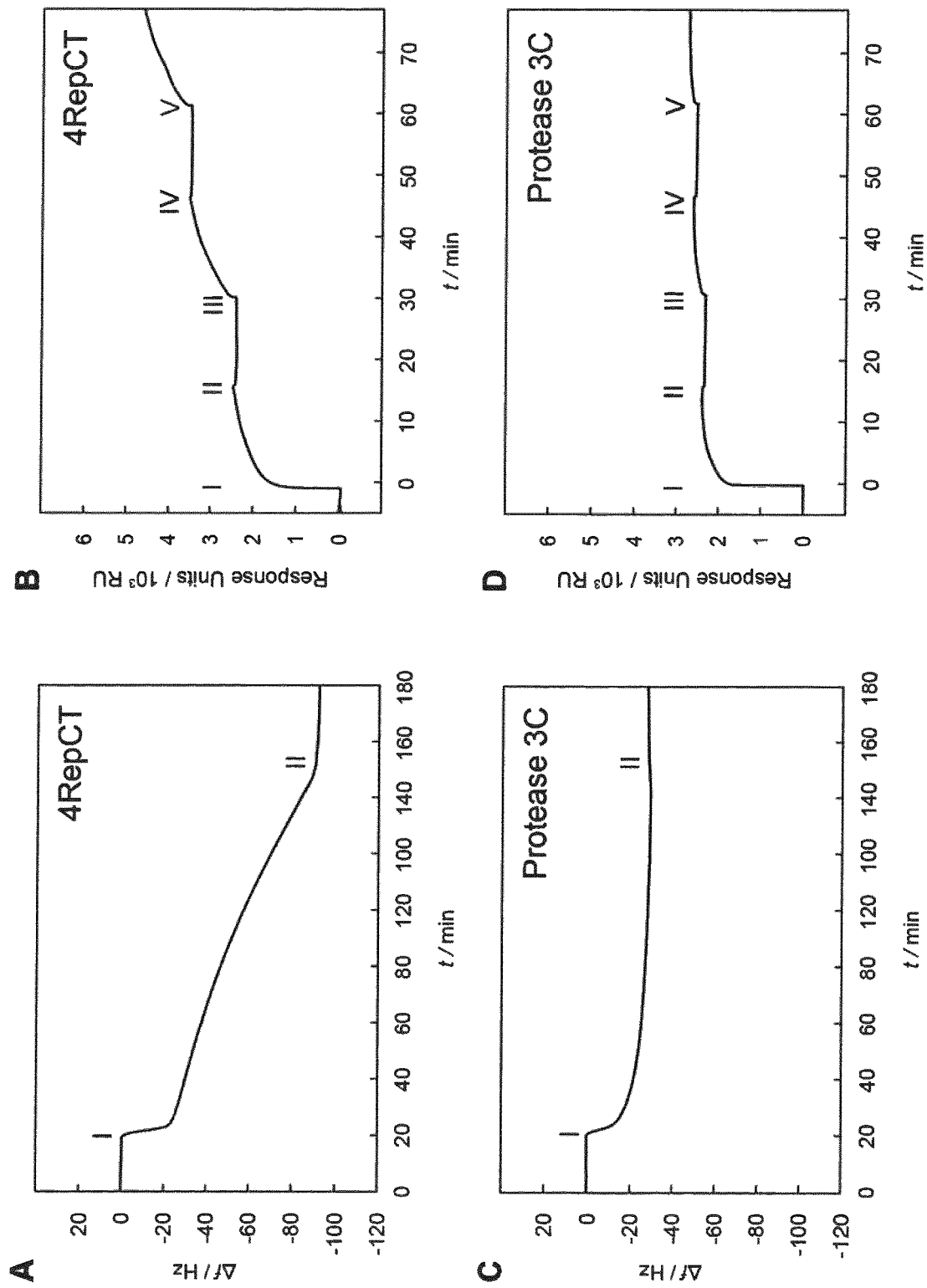
FIG. 1 shows adsorption behavior of the recombinant spider silk protein and a comparative protein (protease 3C).

| SEQ ID NO: | |
|---|---|
| 1 | RepCT (RepCT) (DNA) |
| 2 | RepCT (RepCT) |
| 3 | CT |
| 4 | consensus CT sequence |
| 5 | repetitive sequence from *Euprosthenops australis* MaSp1 |
| 6 | consensus G segment sequence 1 |
| 7 | consensus G segment sequence 2 |
| 8 | consensus G segment sequence 3 |
| 9 | MAG-RepCT |
| 10 | MAG-RepCT (DNA) |
| 11 | $FN_{cc}$-RepCT |
| 12 | $FN_{cc}$-RepCT (DNA) |
| 13 | Z-RepCT |
| 14 | Z-RepCT (DNA) |
| 15 | C2-RepCT |
| 16 | C2-RepCT (DNA) |
| 17 | ABD-RepCT |
| 18 | ABD-RepCT (DNA) |
| 19 | RepCT-FGF |
| 20 | RepCT-FGF (DNA) |
| 21 | IGF1-RepCT |
| 22 | IGF1-RepCT (DNA) |
| 23 | DspB-RepCT |
| 24 | DspB-RepCT (DNA) |
| 25 | WGR-RepCT |
| 26 | WGR-RepCT (DNA) |
| 27 | Xyl-RepCT |
| 28 | Xyl-RepCT (DNA) |
| 29 | M4-RepCT |
| 30 | M4-RepCT (DNA) |
| 31 | Linker peptide 1 |
| 32 | Linker peptide 2 |
| 33 | Linker peptide 3 |
| 34 | Linker peptide 4 |
| 35 | IKVAV |
| 36 | YIGSR |
| 37 | $FN_{cc}$ motif |
| 38 | CT *Euprosthenops sp* MaSp1 |
| 39 | CT *Euprosthenops australis* MaSp1 |
| 40 | CT *Argiope trifasciata* MaSp1 |
| 41 | CT *Cyrtophora moluccensis* Sp1 |
| 42 | CT *Latrodectus geometricus* MaSp1 |
| 43 | CT *Latrodectus hesperus* MaSp1 |
| 44 | CT *Macrothele holsti* Sp1 |
| 45 | CT *Nephila clavipes* MaSp1 |
| 46 | CT *Nephila pilipes* MaSp1 |
| 47 | CT *Nephila madagascariensis* MaSp1 |
| 48 | CT *Nephila senegalensis* MaSp1 |
| 49 | CT *Octonoba varians* Sp1 |
| 50 | CT *Psechrus sinensis* Sp1 |
| 51 | CT *Tetragnatha kauaiensis* MaSp1 |
| 52 | CT *Tetragnatha versicolor* MaSp1 |
| 53 | CT *Araneus bicentenarius* Sp2 |
| 54 | CT *Argiope amoena* MaSp2 |
| 55 | CT *Argiope aurantia* MaSp2 |
| 56 | CT *Argiope trifasciata* MaSp2 |
| 57 | CT *Gasteracantha mammosa* MaSp2 |
| 58 | CT *Latrodectus geometricus* MaSp2 |
| 59 | CT *Latrodectus hesperus* MaSp2 |
| 60 | CT *Nephila clavipes* MaSp2 |
| 61 | CT *Nephila madagascariensis* MaSp2 |
| 62 | CT *Nephila senegalensis* MaSp2 |
| 63 | CT *Dolomedes tenebrosus* Fb1 |
| 64 | CT *Dolomedes tenebrosus* Fb2 |
| 65 | CT *Araneus diadematus* ADF-1 |
| 66 | CT *Araneus diadematus* ADF-2 |
| 67 | CT *Araneus diadematus* ADF-3 |
| 68 | CT *Araneus diadematus* ADF-4 |
| 69 | CT *Araneus ventricosus* MiSp |
| 70 | $FN_{cc}$-RepCT(MiSp) |
| 71 | Rep |
| 72 | RGD-RepCT |

DETAILED DESCRIPTION OF THE INVENTION

The present invention is based on the insight that the recombinant spider silk proteins according to the invention are highly useful as coatings for solid surfaces since they spontaneously form stable coatings with the solid surfaces under physiological-like conditions, i.e. without denaturing conditions during any step of the processing. It is a great advantage that the recombinant spider silk proteins which are functional from the beginning can be rendered into functional surface coatings in physiological-like conditions, as is shown herein. It is noteworthy that the recombinant spider silk proteins according to the invention spontaneously self-assemble into fibrillar structures on the surface without any need for covalent attachment. It is highly surprising that a stable coating can be achieved without active formation of covalent bonds between the surface and the initial layer of the recombinant spider silk proteins according to the invention. This allows for a simple and effective coating process with maintained biological properties of the recombinant spider silk proteins according to the invention also when forming the coating. The process is a wet coating process. This means that the process occurs in the presence of an aqueous solution, and does not involve any step of drying-in of the solution onto the surface to form a film. The resulting coating is significantly thinner than films which are produced by drying-in methods. Thinner coatings are advantageous for cost reasons by decreasing the consumption of raw material. Thinner coatings are also advantageous for safety reasons by decreasing the load of foreign compounds if introduced into the body. Thinner coatings are also advantageous in providing a better direct contact with the underlying surface. This decreases the risk that the coating will peel off the surface and thus contributes to the stability of the coating. The stability of the coating allows for pre-conditioning and sterilization of the coatings, which is crucial for in vivo applications.

Recombinant spider silk is an interesting material for biomaterial applications for several reasons, especially its strength, elasticity and low immunogenicity. The recombinant spider silk proteins according to the invention can be recombinantly produced together with other biologically active peptides such as cell binding motifs or antimicrobial peptides. The soluble fusion proteins can then assemble into stable and flexible macroscopic materials, which retains the function of the peptide motif that was genetically fused to the silk. Furthermore, the recombinant spider silk proteins according to the invention can be recombinantly produced together with functional protein or peptide domains such as affinity domains and enzymes. The fusion protein retains the ability of the spider silk moieties to assemble into macroscopic silk structures, as well as exhibiting activity from the added functional domains.

In order to address complications associated with the surface properties of hard implants, thin silk coatings of the recombinant spider silk proteins according to the invention serve as a suitable format to modify the implant surface properties. The properties of such silk coatings can easily be altered by recombinant expression in fusion with functional peptide motifs or domains. Recombinant spider silk proteins according to the invention fused with different motifs can easily be mixed to allow formation of multi-functional silk coatings.

The recombinant spider silk proteins according to the invention are herein shown to form stable silk coatings on surfaces without covalent attachment, which means that no additional chemicals or harsh conditions are needed during the coating process.

First, the surface adsorption and assembly behavior of non-functionalized recombinant spider silk proteins according to the invention has been characterized. The assembly of the proteins into silk coatings was studied in real-time by several techniques. Quartz Crystal Microbalance with Dissipation (QCM-D) monitors molecular interactions on sensor surfaces in real time with a high sensitivity (ng/cm$^3$). This is done by oscillating the sensor at its resonance frequency and by measuring its responding frequencies. Simultaneously, the dissipation of the oscillation can be monitored, which gives information about the viscoelastic properties of the material. Water that is entrapped in the coating affects the oscillation frequency and dissipation of the sensor and thus contributes to the signal output. Surface Plasmon Resonance (SPR) and ellipsometry are optical techniques that use changes in reflection angles and light polarization changes due to interactions of proteins close to the surface, respectively. Water does not contribute to the responses in either of these two techniques. By simultaneous QCM-D and ellipsometry monitoring in a module designed for combining the two techniques, the adsorbed amount on the surface according to each technique can be determined and used to calculate the water content in the coating. To learn more about the nanostructure of the silk coatings, they were analyzed with Atomic Force Microscopy (AFM), which allows for high-resolution topographic imaging at the nanoscale. By measuring in aqueous solution, the native structure is maintained during characterization.

Second, desired bioactivities were introduced to the implant surfaces by the provision of functional coatings according to the invention from recombinant spider silk proteins fused to various bioactive proteins and peptides, such as a fibronectin peptide motif, which enhances cell adhesion and proliferation on the silk coatings, and the antimicrobial peptide Magainin I. The potential to include functional motifs in the coatings is crucial in biomaterial applications in order to optimize the acceptance of the implants in the body and to tackle infection issues, which are also challenging successful implantation. Furthermore, more advanced bioactivities were introduced using silk proteins fused to protein domains with fold-dependent functions, such as affinity domains (e.g. Z domain binding IgG), enzymes (e.g. xylanase) or growth factors (e.g. fibroblast growth factor, FGF).

According to a first aspect, the present invention provides a method for coating a solid surface with a recombinant spider silk protein capable of forming polymeric, solid structures, comprising the following steps:

exposing the solid surface to an aqueous solution of the recombinant spider silk protein and thereby forming a surface layer of the recombinant spider silk protein adsorbed on the solid surface without formation of covalent bonds between the recombinant spider silk protein and the solid surface; and further exposing the surface layer of the solid surface to an aqueous solution of the recombinant spider silk protein and thereby forming an assembled silk structure layer of the recombinant spider silk protein on the surface layer. In the method according to the invention; the coating process occurs in aqueous solution. This implies that the method does not involve any step of drying-in of the aqueous solution of the recombinant spider silk protein onto the surface. Thus, the method does not include drying-in of spider silk protein.

In the second step of forming an assembled silk structure layer, the assembly continues as long as there is protein available, a distinctive behavior associated with the self-assembling nature of the recombinant spider silk proteins according to the invention.

The inventive method for coating the solid surface with the recombinant spider silk protein in aqueous solution advantageously provide a two-layered structure with a first surface layer which is formed by non-covalent bonds between the recombinant spider silk protein and the solid surface, and a second structure layer, wherein the recombinant spider silk protein spontaneously assembles into silk structure layer on the surface layer.

The process is a wet coating process. This means that the coating process occurs in the presence of an aqueous solution, and does not involve any step of drying-in of the solution onto the surface to form a film.

Compared to conventional drying-in methods of providing films of spider silk proteins, the inventive method for coating the solid surface with the recombinant spider silk protein in aqueous solution provides several advantages:

Rapid production of coatings
Thickness of coating can be controlled
Less batch-to-batch variation and improved reproducibility
Possible to coat any shape of a three-dimensional object.

Compared to conventional dryed-in coatings of spider silk proteins, the coatings of the recombinant spider silk protein provided by the inventive method for coating in aqueous solution have several advantages:

More even coating surfaces
Thinner coatings (typically less than 50 nm thickness compared to 1-2 µm for air-dryed films), which decreases the amount of protein needed and gives better direct contact
A viscous other layer with high water content, which makes the coating more similar to living tissue.

Compared to G. Vidal et al., Acta Biomaterialia, 9(1), 4935-4943 (2013) which investigated the potential to coat titanium surfaces with silk from the silkworm B. mori, that silk type does not show the assembly phase of the recombinant spider silk proteins according to the invention. Instead, protein adsorption in Vidal et al. stagnates after the initial phase where protein-to-surface interactions are built up. Notably, a fraction of the adsorbed proteins are washed away during the buffer flow. The adsorption behavior of B. mori silk on titanium is similar to the non-assembling Protease 3C used as a reference protein in this work. Vidal et al. use chemical coupling of a titanium binding peptide to the B. mori silk proteins to improve the adsorption of the silk to the titanium sensor and avoid protein loss upon rinsing. Interestingly, the recombinant spider silk proteins according to the invention show an inherent propensity to adsorb well to titanium in a way that thereto promotes continuous silk assembly. The spider silk proteins according to the invention are surprisingly efficient in forming the assembled silk structure layer on the initial surface layer, and in the formation of a stable assembled silk structure layer. The thickness of the coating can be regulated by the time of adsorption, and it is stable for rinse with various buffers without the need of any chemical modification or specific peptide motif.

The solid surface is preferably the surface of a biomaterial, and more preferably the surface of an implant or a medical device, such as the surface of an implant.

The solid surface is a preferably a material that is hydrophobic. Preferred hydrophobic solid surfaces according to the invention have a contact angle θ of more than 30° with water, as measured by the pendant drop method. Other preferred solid surfaces according to the invention have a $pK_a$<7 of its exposed hydroxyl groups, if any. A preferred group of hydrophobic solid surfaces according to the invention exhibit both a contact angle θ of more than 30° with water and a $pK_a$<7 of its exposed hydroxyl groups, if any. It is particularly surprising that the recombinant spider silk proteins according to the invention spontaneously self-assemble onto hydrophobic surfaces and surfaces with a low degree of deprotonated hydroxyl groups without the need for complicated and time-consuming methods for introducing charges to the implant surface and creation of numerous layers of coating on the implant surface. These properties of the recombinant spider silk proteins according to the invention renders the process very efficient and yet uncomplicated.

A preferred group of solid surfaces comprise the materials selected from the group consisting of metals, metal alloys, polymers, minerals, glass and glass-like materials, aminosilanes, and hydrophobic hydrocarbons, such as selected from the group consisting of titanium, stainless steel, polystyrene, hydroxyapatite, silicon dioxide, APTES-functionalized silicon dioxide, gold, and alkyl thiol-functionalized gold, such as alkyl thiol-functionalized gold having a contact angle>30°. A preferred solid surface is polystyrene.

The method according to the invention may further comprise one or more washing steps between or after the steps of exposing the solid surface or the surface layer to an aqueous solution of the recombinant spider silk protein, wherein each washing step involves removal of soluble recombinant spider silk protein adjacent to the coated surface. Preferred washing steps include washing with alcohols, such as ethanol, acid, such as HCl and/or base, such as NaOH. The coating is advantageously resistant towards practically relevant concentrations of alcohols, acid and base. This makes it possible to wash and sterilize the coated surface without loss of biofunctionality or detachment of the coating from the surface.

As set out above, the coating process is a wet coating process. This means that the coating occurs in the presence of an aqueous solution of the recombinant spider silk protein, and does not involve any step of drying-in of this solution onto the surface to form a film. It is however possible to dry the resulting coating with immobilized spider silk protein after the aqueous solution of the recombinant spider silk protein has been removed, and preferably after one or more washing steps as set out above.

A preferred group of recombinant spider silk proteins according to the invention is further comprising a functionally exposed non-spidroin protein moiety or non-spidroin polypeptide moiety, which is a bioactive protein moiety or a bioactive peptide moiety. Advantageously, the bioactive protein/peptide moiety is functionally exposed even when the spidroin moieties are forming the assembled silk structure layer. Non-limiting examples of the bioactive protein/peptide moieties include cell binding motifs, antimicrobial peptides, affinity domains, enzymes, growth factors and recombinant antibody fragments.

The non-spidroin moiety is a protein or polypeptide fragment comprising at least 3 amino acid residues which provide a bioactivity, e.g. affinity and/or enzymatic activity. In particular, short non-spidroin moieties in the range of 3-10 amino acid residues may constitute cell-binding motifs, e.g. RGD. The non-spidroin moiety is preferably comprising more than 10 amino acid residues, such as more than 30 amino acid residues, such as more than 50 amino acid residues. The non-spidroin moiety is preferably comprising less than 1000 amino acid residues, such as less than 400 amino acid residues, more preferably less than 300 amino acid residues.

The moieties derived from the spider silk protein can be induced to rearrange structurally and as a result form polymeric, solid structures, while the non-spidroin moiety is not structurally rearranged but maintains its desirable structure and bioactivity. The protein according to the invention may thus harbors both a desired bioactivity and an internal solid support activity that is employed in the protein structure under physiological conditions. The bioactivity of the non-spidroin protein/polypeptide moiety is maintained although the non-spidroin moiety is covalently attached to the spidroin moiety when the latter is structurally rearranged to form polymeric, solid structures.

The term "non-spidroin" implies proteins that are not derived from a spider silk protein, i.e. with a low (or no) degree of identity and/or similarity to spider silk proteins. The non-spidroin moiety has preferably less than 30% identity, such as less than 20% identity, preferably less than 10(Y0 identity, to any of the spidroin amino acid sequences disclosed herein, and specifically to any of SEQ ID NO: 2-8 and 71.

A preferred group of recombinant spider silk proteins according to the invention is comprising, or consisting of, the protein moieties REP and optionally CT, and optionally a functionally exposed non-spidroin protein/polypeptide moiety, wherein REP is a repetitive fragment of from 70 to 300 amino acid residues, selected from the group consisting of $L(AG)_nL$, $L(AG)_nAL$, $L(GA)_nL$, and $L(GA)_nGL$, wherein
  n is an integer from 2 to 10;
  each individual A segment is an amino acid sequence of from 8 to 18 amino acid residues, wherein from 0 to 3 of the amino acid residues are not Ala, and the remaining amino acid residues are Ala;
  each individual G segment is an amino acid sequence of from 12 to 30 amino acid residues, wherein at least 40% of the amino acid residues are Gly; and
  each individual L segment is a linker amino acid sequence of from 0 to 30 amino acid residues; and
CT is a fragment of from 70 to 120 amino acid residues, having at least 70% identity to SEQ ID NO 3 or SEQ ID NO: 69.

The fusion protein according to the invention harbors an internal solid support activity in the spidroin fragments REP and CT, and optionally a further bioactivity in the functionally exposed non-spidroin protein/polypeptide moiety. The bioactivity of the fusion protein is maintained when it is structurally rearranged to form polymeric, solid structures. These protein structures, or protein polymers, also provide a high and predictable density of the functionally exposed non-spidroin protein/polypeptide moiety.

In most of the proteins that have been engineered to contain a functionally exposed non-spidroin protein/polypeptide moiety, this moiety has been added as a linear extension either to the N- or C-terminus, thus with a high possibility of exposure and flexibility due to minimal constraint of the chain from the rest of the protein. It is also possible to place the functionally exposed non-spidroin protein/polypeptide moiety placed within a recombinant spider silk protein, such as between a REP and a CT moiety.

The term "fusion protein" implies here a protein that is made by expression from a recombinant nucleic acid, i.e. DNA or RNA that is created artificially by combining two or more nucleic acid sequences that would not normally occur together (genetic engineering). The fusion proteins according to the invention are recombinant proteins, and they are therefore not identical to naturally occurring proteins. In particular, wildtype spidroins are not fusion proteins according to the invention, because they are not expressed from a recombinant nucleic acid as set out above. The combined nucleic acid sequences encode different proteins, partial proteins or polypeptides with certain functional properties. The resulting fusion protein, or recombinant fusion protein, is a single protein with functional properties derived from each of the original proteins, partial proteins or polypeptides. Furthermore, the fusion protein according to the invention and the corresponding genes are chimeric, i.e. the protein/gene moieties are derived from at least two different species.

The fusion protein typically consists of from 170 to 2000 amino acid residues, such as from 170 to 1000 amino acid residues, such as from 170 to 600 amino acid residues, preferably from 170 to 500 amino acid residues, such as from 170 to 400 amino acid residues. The small size is advantageous because longer proteins containing spider silk protein fragments may form amorphous aggregates, which require use of harsh solvents for solubilisation and polymerisation.

The fusion protein may contain one or more linker peptides, or L segments. The linker peptide(s) may be arranged between any moieties of the fusion protein, e.g. between the REP and CT moieties, at either terminal end of the fusion protein or between the spidroin fragment and the cell-binding motif. The linker(s) may provide a spacer between the functional units of the fusion protein, but may also constitute a handle for identification and purification of the fusion protein, e.g. a His and/or a Trx tag. If the fusion protein contains two or more linker peptides for identification and purification of the fusion protein, it is preferred that they are separated by a spacer sequence, e.g. $His_6$-spacer-$His_6$-. The linker may also constitute a signal peptide, such as a signal recognition particle, which directs the fusion protein to the membrane and/or causes secretion of the fusion protein from the host cell into the surrounding medium. The fusion protein may also include a cleavage site in its amino acid sequence, which allows for cleavage and removal of the linker(s) and/or other relevant moieties. Various cleavage sites are known to the person skilled in the art, e.g. cleavage sites for chemical agents, such as CNBr after Met residues and hydroxylamine between Asn-Gly residues, cleavage sites for proteases, such as thrombin or protease 3C, and self-splicing sequences, such as intein self-splicing sequences.

The spidroin fragments and the functionally exposed non-spidroin protein/polypeptide moiety are linked directly or indirectly to one another. A direct linkage implies a direct covalent binding between the moieties without intervening sequences, such as linkers. An indirect linkage also implies that the moieties are linked by covalent bonds, but that there are intervening sequences, such as linkers and/or one or more further moieties, e.g. 1-2 moieties.

The functionally exposed non-spidroin protein/polypeptide moiety may thus be arranged internally or at either end of the fusion protein, i.e. C-terminally arranged or N-terminally arranged. It is preferred that the cell-binding motif is arranged at the N-terminal end of the fusion protein. If the fusion protein contains one or more linker peptide(s) for identification and purification of the fusion protein, e.g. a His or Trx tag(s), it is preferred that it is arranged at the N-terminal end of the fusion protein.

A preferred fusion protein has the form of an N-terminally arranged functionally exposed non-spidroin protein/polypeptide moiety, coupled by a linker peptide of 0-30 amino acid residues, such as 0-10 amino acid residues, to a REP moiety. Optionally, the fusion protein has an N-terminal or C-terminal linker peptide, which may contain a purification tag, such as a His tag, and a cleavage site.

Without wishing to be bound to any specific theory, it is contemplated that the non-spidroin protein/polypeptide moiety is functionally displayed on the surface of the resulting coating, c.f. Examples 6-13.

The protein moiety REP is a fragment with a repetitive character, alternating between alanine-rich stretches and glycine-rich stretches. The REP fragment generally contains more than 70, such as more than 140, and less than 300, preferably less than 240, such as less than 200, amino acid residues, and can itself be divided into several L (linker) segments, A (alanine-rich) segments and G (glycine-rich) segments, as will be explained in more detail below. Typically, said linker segments, which are optional, are located at the REP fragment terminals, while the remaining segments are in turn alanine-rich and glycine-rich. Thus, the REP fragment can generally have either of the following structures, wherein n is an integer:

$L(AG)_nL$, such as $LA_1G_1A_2G_2A_3G_3A_4G_4A_5G_5L$;
$L(AG)_nAL$, such as $LA_1G_1A_2G_2A_3G_3A_4G_4A_5G_5A_6L$;
$L(GA)_nL$, such as $LG_1A_1G_2A_2G_3A_3G_4A_4G_5A_5L$; or
$L(GA)_nGL$, such as $LG_1A_1G_2A_2G_3A_3G_4A_4G_5A_5G_6L$.

It follows that it is not critical whether an alanine-rich or a glycine-rich segment is adjacent to the N-terminal or C-terminal linker segments. It is preferred that n is an integer from 2 to 10, preferably from 2 to 8, also preferably from 4 to 8, more preferred from 4 to 6, i.e. n=4, n=5 or n=6.

In some embodiments, the alanine content of the REP fragment is above 20%, preferably above 25%, more preferably above 30%, and below 50%, preferably below 40%, more preferably below 35%. It is contemplated that a higher alanine content provides a stiffer and/or stronger and/or less extendible fiber.

In certain embodiments, the REP fragment is void of proline residues, i.e. there are no Pro residues in the REP fragment.

Turning now to the segments that constitute the REP fragment, it is emphasized that each segment is individual, i.e. any two A segments, any two G segments or any two L segments of a specific REP fragment may be identical or may not be identical. Thus, it is not a general feature of the spidroin that each type of segment is identical within a specific REP fragment. Rather, the following disclosure provides the skilled person with guidelines how to design individual segments and gather them into a REP fragment, which is a part of a functional spider silk protein useful in a cell scaffold material.

Each individual A segment is an amino acid sequence having from 8 to 18 amino acid residues. It is preferred that each individual A segment contains from 13 to 15 amino acid residues. It is also possible that a majority, or more than two, of the A segments contain from 13 to 15 amino acid residues, and that a minority, such as one or two, of the A segments contain from 8 to 18 amino acid residues, such as 8-12 or 16-18 amino acid residues. A vast majority of these amino acid residues are alanine residues. More specifically, from 0 to 3 of the amino acid residues are not alanine residues, and the remaining amino acid residues are alanine residues. Thus, all amino acid residues in each individual A segment are alanine residues, with no exception or with the exception of one, two or three amino acid residues, which can be any amino acid. It is preferred that the alanine-replacing amino acid(s) is (are) natural amino acids, preferably individually selected from the group of serine, glutamic acid, cysteine and glycine, more preferably serine. Of course, it is possible that one or more of the A segments are all-alanine segments, while the remaining A segments contain 1-3 non-alanine residues, such as serine, glutamic acid, cysteine or glycine.

In an embodiment, each A segment contains 13-15 amino acid residues, including 10-15 alanine residues and 0-3 non-alanine residues as described above. In a more preferred embodiment, each A segment contains 13-15 amino acid residues, including 12-15 alanine residues and 0-1 non-alanine residues as described above.

It is preferred that each individual A segment has at least 80%, preferably at least 90%, more preferably 95%, most preferably 100% identity to an amino acid sequence selected from the group of amino acid residues 7-19, 43-56, 71-83, 107-120, 135-147, 171-183, 198-211, 235-248, 266-279, 294-306, 330-342, 357-370, 394-406, 421-434, 458-470, 489-502, 517-529, 553-566, 581-594, 618-630, 648-661, 676-688, 712-725, 740-752, 776-789, 804-816, 840-853, 868-880, 904-917, 932-945, 969-981, 999-1013, 1028-1042 and 1060-1073 of SEQ ID NO: 5. Each sequence of this group corresponds to a segment of the naturally occurring sequence of *Euprosthenops australis* MaSp1 protein, which is deduced from cloning of the corresponding cDNA, see WO 2007/078239. Alternatively, each individual A segment has at least 80%, preferably at least 90%, more preferably 95%, most preferably 100% identity to an amino acid sequence selected from the group of amino acid residues 25-36, 55-69, 84-98, 116-129 and 149-158 of SEQ ID NO: 2. Each sequence of this group corresponds to a segment of expressed, non-natural spider silk proteins, which proteins have the capacity to form silk fibers under appropriate conditions. Thus, in certain embodiments of the spidroin, each individual A segment is identical to an amino acid sequence selected from the above-mentioned amino acid segments. Without wishing to be bound by any particular theory, it is envisaged that A segments according to the invention form helical structures or beta sheets.

Furthermore, it has been concluded from experimental data that each individual G segment is an amino acid sequence of from 12 to 30 amino acid residues. It is preferred that each individual G segment consists of from 14 to 23 amino acid residues. At least 40% of the amino acid residues of each G segment are glycine residues. Typically the glycine content of each individual G segment is in the range of 40-60%.

It is preferred that each individual G segment has at least 80%, preferably at least 90%, more preferably 95%, most preferably 100% identity to an amino acid sequence selected from the group of amino acid residues 20-42, 57-70, 84-106, 121-134, 148-170, 184-197, 212-234, 249-265, 280-293, 307-329, 343-356, 371-393, 407-420, 435-457, 471-488, 503-516, 530-552, 567-580, 595-617, 631-647, 662-675, 689-711, 726-739, 753-775, 790-803, 817-839, 854-867, 881-903, 918-931, 946-968, 982-998, 1014-1027, 1043-1059 and 1074-1092 of SEQ ID NO: 5. Each sequence of this group corresponds to a segment of the naturally occurring sequence of *Euprosthenops australis* MaSp1 protein, which is deduced from cloning of the corresponding cDNA, see WO 2007/078239. Alternatively, each individual G segment has at least 80%, preferably at least 90%, more preferably 95%, most preferably 100% identity to an amino acid sequence selected from the group of amino acid residues 1-24, 37-54, 70-83, 99-115 and 130-148 of SEQ ID NO: 2. Each sequence of this group corresponds to a segment of expressed, non-natural spider silk proteins, which proteins have the capacity to form silk fibers under appropriate conditions. Thus, in certain embodiments of the spidroin in the cell scaffold material, each individual G segment is identical to an amino acid sequence selected from the above-mentioned amino acid segments.

In certain embodiments, the first two amino acid residues of each G segment are not -Gln-Gln-.

There are three subtypes of the G segment. This classification is based upon careful analysis of the *Euprosthenops australis* MaSp1 protein sequence (see WO 2007/078239), and the information has been employed and verified in the construction of novel, non-natural spider silk proteins.

The first subtype of the G segment is represented by the amino acid one letter consensus sequence GQG(G/S)QGG (Q/Y)GG (L/Q)GQGGYGQGA GSS (SEQ ID NO: 6). This first, and generally the longest, G segment subtype typically contains 23 amino acid residues, but may contain as little as 17 amino acid residues, and lacks charged residues or contain one charged residue. Thus, it is preferred that this first G segment subtype contains 17-23 amino acid residues, but it is contemplated that it may contain as few as 12 or as many as 30 amino acid residues. Without wishing to be bound by any particular theory, it is envisaged that this subtype forms coil structures or $3_1$-helix structures. Representative G segments of this first subtype are amino acid residues 20-42, 84-106, 148-170, 212-234, 307-329, 371-393, 435-457, 530-552, 595-617, 689-711, 753-775, 817-839, 881-903, 946-968, 1043-1059 and 1074-1092 of SEQ ID NO: 5. In certain embodiments, the first two amino acid residues of each G segment of this first subtype according to the invention are not -Gln-Gln-.

The second subtype of the G segment is represented by the amino acid one letter consensus sequence GQGGQGQG (G/R)Y GQG(A/S)G(S/G)S (SEQ ID NO: 7). This second, generally mid-sized, G segment subtype typically contains 17 amino acid residues and lacks charged residues or contain one charged residue. It is preferred that this second G segment subtype contains 14-20 amino acid residues, but it is contemplated that it may contain as few as 12 or as many as 30 amino acid residues. Without wishing to be bound by any particular theory, it is envisaged that this subtype forms coil structures. Representative G segments of this second subtype are amino acid residues 249-265, 471-488, 631-647 and 982-998 of SEQ ID NO: 5.

The third subtype of the G segment is represented by the amino acid one letter consensus sequence G(R/Q)GQG(G/R)YGQG (A/S/V)GGN (SEQ ID NO: 8). This third G segment subtype typically contains 14 amino acid residues, and is generally the shortest of the G segment subtypes. It is preferred that this third G segment subtype contains 12-17 amino acid residues, but it is contemplated that it may contain as many as 23 amino acid residues. Without wishing to be bound by any particular theory, it is envisaged that this subtype forms turn structures. Representative G segments of this third subtype are amino acid residues 57-70, 121-134, 184-197, 280-293, 343-356, 407-420, 503-516, 567-580, 662-675, 726-739, 790-803, 854-867, 918-931, 1014-1027 of SEQ ID NO: 5.

Thus, in preferred embodiments of the spidroin in the silk coating, each individual G segment has at least 80%, preferably 90%, more preferably 95%, identity to an amino acid sequence selected from SEQ ID NO: 6, SEQ ID NO: 7 and SEQ ID NO: 8.

In an embodiment of the alternating sequence of A and G segments of the REP fragment, every second G segment is of the first subtype, while the remaining G segments are of the third subtype, e.g. . . . $A_1G_{short}A_2G_{long}A_3G_{short}A_4G_{long}A_5G_{short}$ . . . . In another embodiment of the REP fragment, one G segment of the second subtype interrupts the G segment regularity via an insertion, e.g. . . . $A_1G_{short}A_2G_{long}A_3G_{mid}A_4G_{short}A_5G_{long}$ . . . .

Each individual L segment represents an optional linker amino acid sequence, which may contain from 0 to 30 amino acid residues, such as from 0 to 20 amino acid residues. While this segment is optional and not critical for the function of the spider silk protein, its presence still allows for fully functional spider silk proteins and polymers thereof which form fibers, films, foams and other structures. There are also linker amino acid sequences present in the repetitive part (SEQ ID NO: 5) of the deduced amino acid sequence of the MaSp1 protein from *Euprosthenops australis*. In particular, the amino acid sequence of a linker segment may resemble any of the described A or G segments, but usually not sufficiently to meet their criteria as defined herein.

As shown in WO 2007/078239, a linker segment arranged at the C-terminal part of the REP fragment can be represented by the amino acid one letter consensus sequences ASASAAASAA STVANSVS (SEQ ID NO: 31) and ASAASAAA (SEQ ID NO: 32), which are rich in alanine. In fact, the second sequence can be considered to be an A segment according to the definition herein, whereas the first sequence has a high degree of similarity to A segments according to this definition. Another example of a linker segment has the one letter amino acid sequence GSAMGQGS (SEQ ID NO: 33), which is rich in glycine and has a high degree of similarity to G segments according to the definition herein. Another example of a linker segment is SASAG (SEQ ID NO: 34).

Representative L segments are amino acid residues 1-6 and 1093-1110 of SEQ ID NO: 5; and amino acid residues 159-165 of SEQ ID NO: 2, but the skilled person will readily recognize that there are many suitable alternative amino acid sequences for these segments. In one embodiment of the REP fragment, one of the L segments contains 0 amino acids, i.e. one of the L segments is void. In another embodiment of the REP fragment, both L segments contain 0 amino acids, i.e. both L segments are void. Thus, these embodiments of the REP fragments according to the invention may be schematically represented as follows: $(AG)_nL$, $(AG)_nAL$, $(GA)_nL$, $(GA)_nGL$; $L(AG)_n$, $L(AG)_nA$, $L(GA)_n$, $L(GA)_nG$; and $(AG)_n$, $(AG)_nA$, $(GA)_n$, $(GA)_nG$. Any of these REP fragments are suitable for use with any CT fragment as defined below.

The optional but preferred CT fragment of the spidroin in the cell scaffold material has a high degree of similarity to the C-terminal amino acid sequence of spider silk proteins. As shown in WO 2007/078239, this amino acid sequence is well conserved among various species and spider silk proteins, including MaSp1, MaSp2 and MiSp (minor ampullate spidroin). A consensus sequence of the C-terminal regions of MaSp1 and MaSp2 is provided as SEQ ID NO: 4. In FIG. 10, the MaSp proteins (SEQ ID NO: 38-68) presented in Table 1 are aligned, denoted with GenBank accession entries where applicable.

TABLE 1

Spidroin CT fragments

| Species and spidroin | Entry |
|---|---|
| *Euprosthenops* sp MaSp1 (Pouchkina-Stantcheva*) | Cthyb_Esp |
| *Euprosthenops australis* MaSp1 (SEQ ID NO: 3) | CTnat_Eau |
| *Argiope trifasciata* MaSp1 | AF350266_At1 |
| *Cyrtophora moluccensis* Sp1 | AY666062_Cm1 |
| *Latrodectus geometricus* MaSp1 | AF350273_Lg1 |
| *Latrodectus hesperus* MaSp1 | AY953074_Lh1 |
| *Macrothele holsti* Sp1 | AY666068_Mh1 |
| *Nephila clavipes* MaSp1 | U20329_Nc1 |
| *Nephila pilipes* MaSp1 | AY666076_Np1 |
| *Nephila madagascariensis* MaSp1 | AF350277_Nm1 |
| *Nephila senegalensis* MaSp1 | AF350279_Ns1 |
| *Octonoba varians* Sp1 | AY666057_Ov1 |
| *Psechrus sinensis* Sp1 | AY666064_Ps1 |
| *Tetragnatha kauaiensis* MaSp1 | AF350285_Tk1 |
| *Tetragnatha versicolor* MaSp1 | AF350286_Tv1 |
| *Araneus bicentenarius* Sp2 | ABU20328_Ab2 |
| *Argiope amoena* MaSp2 | AY365016_Aam2 |
| *Argiope aurantia* MaSp2 | AF350263_Aau2 |
| *Argiope trifasciata* MaSp2 | AF350267_At2 |
| *Gasteracantha mammosa* MaSp2 | AF350272_Gm2 |

TABLE 1-continued

Spidroin CT fragments

| Species and spidroin | Entry |
|---|---|
| *Latrodectus geometricus* MaSp2 | AF350275_Lg2 |
| *Latrodectus hesperus* MaSp2 | AY953075_Lh2 |
| *Nephila clavipes* MaSp2 | AY654293_Nc2 |
| *Nephila madagascariensis* MaSp2 | AF350278_Nm2 |
| *Nephila senegalensis* MaSp2 | AF350280_Ns2 |
| *Dolomedes tenebrosus* Fb1 | AF350269_DtFb1 |
| *Dolomedes tenebrosus* Fb2 | AF350270_DtFb2 |
| *Araneus diadematus* ADF-1 | U47853_ADF1 |
| *Araneus diadematus* ADF-2 | U47854_ADF2 |
| *Araneus diadematus* ADF-3 | U47855_ADF3 |
| *Araneus diadematus* ADF-4 | U47856_ADF4 |

*Comparative Biochemistry and Physiology, Part B 138: 371-376 (2004)

It is not critical which specific CT fragment is present in the spider silk protein in the cell scaffold material. Thus, the CT fragment can be selected from any of the amino acid sequences shown in FIG. 10 and Table 1 or sequences with a high degree of similarity, such as the MiSp CT fragment SEQ ID NO: 69 from *Araneus ventricosus* (Genbank entry AFV 31615). A wide variety of C-terminal sequences can be used in the spider silk protein.

The sequence of the CT fragment has at least 50% identity, preferably at least 60%, more preferably at least 65% identity, or even at least 70% identity, to the consensus amino acid sequence SEQ ID NO: 4, which is based on the amino acid sequences of FIG. 10.

A representative CT fragment is the *Euprosthenops australis* sequence SEQ ID NO: 3 or amino acid residues 166-263 of SEQ ID NO: 2. Another representative CT fragment is the MiSp sequence SEQ ID NO: 69. Thus, in one embodiment, the CT fragment has at least 70%, such as at least 80%, such as at least 85%, preferably at least 90%, such as at least 95%, identity to SEQ ID NO: 3, amino acid residues 166-263 of SEQ ID NO: 2, any individual amino acid sequence of FIG. 10 and Table 1, or SEQ ID NO: 69. For example, the CT fragment may be identical to SEQ ID NO: 3, amino acid residues 166-263 of SEQ ID NO: 2, any individual amino acid sequence of FIG. 10 and Table 1, or SEQ ID NO: 69.

The CT fragment typically consists of from 70 to 120 amino acid residues. It is preferred that the CT fragment contains at least 70, or more than 80, preferably more than 90, amino acid residues. It is also preferred that the CT fragment contains at most 120, or less than 110 amino acid residues. A typical CT fragment contains approximately 100 amino acid residues.

The term "% identity", as used herein, is calculated as follows. The query sequence is aligned to the target sequence using the CLUSTAL W algorithm (Thompson et al, Nucleic Acids Research, 22:4673-4680 (1994)). A comparison is made over the window corresponding to the shortest of the aligned sequences. The amino acid residues at each position are compared, and the percentage of positions in the query sequence that have identical correspondences in the target sequence is reported as % identity.

The term "% similarity", as used herein, is calculated as described above for "% identity", with the exception that the hydrophobic residues Ala, Val, Phe, Pro, Leu, Ile, Trp, Met and Cys are similar; the basic residues Lys, Arg and His are similar; the acidic residues Glu and Asp are similar; the hydrophilic, uncharged residues Gln, Asn, Ser, Thr and Tyr are similar. The remaining natural amino acid Gly is not similar to any other amino acid in this context.

Throughout this description, alternative embodiments according to the invention fulfill, instead of the specified percentage of identity, the corresponding percentage of similarity. Other alternative embodiments fulfill the specified percentage of identity as well as another, higher percentage of similarity, selected from the group of preferred percentages of identity for each sequence. For example, a sequence may be 70% similar to another sequence; or it may be 70% identical to another sequence; or it may be 70% identical and 90% similar to another sequence.

In a preferred fusion protein according to the invention, the REP-CT fragment has at least 70%, such as at least 80%, such as at least 85%, preferably at least 90%, such as at least 95%, identity to SEQ ID NO: 2.

In one preferred fusion protein according to the invention, the protein has at least 70%, such as at least 80%, such as at least 85%, preferably at least 90%, such as at least 95%, identity to any one of SEQ ID NO: 9, 11, 13, 15, 17, 19, 21, 23, 25, 27, 29 and 70. In a particularly preferred embodiment, the fusion protein according to the invention is any one of SEQ ID NO: 9, 11, 13, 15, 17, 19, 21, 23, 25, 27, 29 and 70.

The functionally exposed non-spidroin protein/polypeptide moiety could be any moiety which is desirable to expose in this context, and in particular a cell-binding motif or another peptide/protein which has can provide a desirable binding functionality to the spider silk protein according to the invention.

Specific cell-binding peptides which are useful in the present invention include RGD, IKVAV (SEQ ID NO: 35), YIGSR (SEQ ID NO: 36), and in particular RGD. A particularly preferred cell-binding peptide is the $FN_{cc}$ motif, i.e. a RGD motif flanked by a first Cys as the third upstream residue and a second Cys residue as the fourth downstream residue (CXXRGDXXXC; SEQ ID NO: 37), c.f. SEQ ID NO: 11.

Other specific useful proteins are affinity domains, including staphylococcal protein A and variants thereof, such as the Z domain; streptococcal protein G and variants thereof, albumin and variants thereof, biotin and variants thereof; and streptavidin and variants thereof.

Another group of specific useful proteins include antimicrobial peptides and variants thereof, such as Magainin I.

Another group of specific useful proteins are enzymes and variants thereof, including xylanase and Dispersin B.

Another group of specific useful proteins are growth factors and variants thereof, including FGF, FGF2, IGF1, EGF1, NGF1, VEGF and variants thereof.

Another group of specific useful proteins are recombinant antibody fragments and fusions thereof, including single chain variable fragments (scFv), $F_{ab}$ fragments and variants thereof.

In this context, a protein is considered to be a "variant" if it has a specific binding affinity to a target molecule and at least 70%, such as 80%, 85%, 90% or 95% identity to the original molecule or one of its moieties over a window of at least 15 amino acid residues, preferably at least 20, 25 or 30 amino acid residues.

According to a related aspect, the present invention provides use of a recombinant spider silk protein according to the invention, wherein said recombinant spider silk protein is a fusion protein comprising a functionally exposed non-spidroin protein/polypeptide moiety. Preferred non-spidroin protein/polypeptide moieties are disclosed above.

According to a second aspect, the present invention provides a solid surface coated with a recombinant spider silk protein capable of forming polymeric, solid structures, wherein the recombinant spider silk protein coating is comprising:
- a surface layer of the recombinant spider silk protein adsorbed on the solid surface without formation of covalent bonds between the recombinant spider silk protein and the solid surface; and
- an assembled silk structure layer of the recombinant spider silk protein on the surface layer.

Compared to conventional dryed-in coatings of spider silk proteins, the coatings of the recombinant spider silk protein provided by the inventive method for coating in aqueous solution have several advantages:
- More even coating surfaces
- Thinner coatings (typically less than 50 nm thickness compared to 1-2 μm for air-dryed films), which decreases the amount of protein needed and gives better direct contact
- A viscous other layer with high water content, which makes the coating more similar to living tissue.

The inventive method for coating the solid surface with the recombinant spider silk protein in aqueous solution advantageously provide a two-layered structure with a first surface layer which is formed by non-covalent bonds between the recombinant spider silk protein and the solid surface, and a second structure layer, wherein the recombinant spider silk protein spontaneously assembles into silk structure layer on the surface layer. The spider silk proteins according to the invention are surprisingly efficient in forming the assembled silk structure layer on the initial surface layer, and in the formation of a stable assembled silk structure layer.

An interesting property of the resulting two-layered structure is that the assembled silk structure layer is more viscous than the surface layer. The initial surface layer contains less water and is therefore more rigid, while the assembled silk structure layer contains more water and is more viscous. This makes the coated structure of e.g. an implant more similar to the surrounding tissue and decreases the risk for inflammatory reactions etc. The viscosity of the two layers can be determined by comparing their dissipation to frequency ratio using Quartz Crystal Microbalance with Dissipation monitoring (QCM-D).

The assembled silk structure layer has a higher dissipation to frequency ratio than the initial surface layer, preferably at least 2 times higher, and typically 5-10 times higher.

The assembled silk structure layer is preferably in a physical form of nanofibrils, preferably having a diameter of less than 20 nm, such as 10-20 nm; and/or wherein the recombinant spider silk protein coating has a total thickness of less than 50 nm, such as 10-40 nm.

Preferred materials which can constitute the solid surface are disclosed herein. Preferred recombinant spider silk proteins are also disclosed herein.

In a preferred embodiment, the solid surface coated with a recombinant spider silk protein according to the invention is preparable, or even prepared, by the process according to the invention.

The solid surface is preferably the surface of a biomaterial, an implant or a medical device, more preferably of an implant. The coated surface is also useful as a matrix for cell culture, preferably in vitro. The coated surface according to the invention is also useful as a scaffold for cell immobilization, cell culture, cell differentiation, tissue engineering and guided cell regeneration. It is also useful in preparative and analytical separation procedures, such as chromatography, cell capture, selection and culture, active filters, and diagnostics.

In one embodiment, the solid surface coated with a recombinant spider silk protein according to the invention is further comprising eukaryotic cells growing attached onto the recombinant spider silk protein coating. Preferred cell types include fibroblast cells and endothelial cells, preferably human cells, and preferably human primary cells.

By studying surface adsorption of recombinant spider silk protein according to the invention in real-time by QCM-D, ellipsometry, and SPR, it is shown that these proteins spontaneously assemble into silk coatings as long as the surface is exposed to protein solution. Coatings were stable towards wash with up to 0.5 M HCl, 0.5 M NaOH, and 70% ethanol, as well as PBS, which means that the coatings can be sterilized and has potential to be used for in vivo applications. Protein-to-surface interactions build a rigid initial protein layer on the surface, whereas the subsequent protein-to-protein assembly incorporates large amounts of water in the coating, resulting in a viscous phase. An investigation of the surface topography of the protein coatings show that the proteins assemble into nanofibrils and form a heterogenous layer, which may be compared to the fibrillar structures of the connective tissue in the body. Silk proteins functionalized with a fibronectin motif and an antimicrobial peptide could form coatings on polystyrene, titanium, and stainless steel. The coating method is highly useful to functionalize implant materials using physiological-like conditions, in order to improve their function in the body. Culturing fibroblast cells on coatings on both types of functionalized silk showed good cell viability. Similar results were obtained from culturing endothelial cells on silk coatings with the fibronectin motif. The coating method is also highly useful to allow for versatile functionalization of solid surfaces. For instance, the Fc portion of IgG molecules having virtually any desired affinity can be immobilized to coatings with spider silk in fusion to a Z moiety.

The present invention will in the following be further illustrated by the following non-limiting examples.

EXAMPLES

Experimental Section

Materials

Proteins were recombinantly produced in *E. coli* BL21 and purified using chromatography. Proteins were used in 20 mM Tris buffer, pH 8.0 if other conditions are not stated. Protein solutions were kept on ice during adsorption measurements. Alkyl thiol solutions with 1-undecanethiol (Sigma Aldrich) were prepared as 2 mM solutions in 99.5% ethanol (Solveco). 2% polystyrene solution was prepared by dissolving petri dish pieces in toluene.

Quartz Crystal Microbalance with Dissipation Monitoring

Quartz Crystal Microbalance with Dissipation Monitoring (QCM-D) takes advantage of the piezoelectric properties of AT-cut quartz crystals to monitor changes in its oscillation frequency and dissipation of oscillation through application of pulsative voltage. Upon adsorption of mass onto the crystal sensor, the frequency decreases and the dissipation increases. By comparing dissipation changes to frequency changes, viscoelastic properties of the adsorbed layer can be assessed.

QCM-D sensors coated with titanium and stainless steel of type SS2343 (Biolin Scientific) were cleaned according to the manufacturer recommendations and used without further modification. Gold coated QCM-D sensors were cleaned by a three-step procedure starting with immersion in 98% formic acid for 10 minutes followed by extensive rinsing in Milli-Q water, 5 min plasma treatment at maximum power in a Harrick Plasma PDC-3XG plasma cleaner, and subsequent incubation in a 6:1:1 mixture of Milli-Q water, 32% ammonia, and 30% hydrogen peroxide for 8 min at 80° C. After extensive rinsing in Milli-Q water, the surfaces were dried in nitrogen gas and incubated in alkyl thiol solution over night. Excessive alkyl thiols were removed by 5 min ultra-sonication in 99.5% ethanol, repeated 5 times. The functionalization was verified by measuring the contact angle of 2 µl Milli-Q water drops on each sensor on a DataPhysics OCA40 instrument, showing hydrophobic surfaces with a contact angle of 102°±2°. Polystyrene sensors were prepared by spin coating of 2% polystyrene in toluene on gold sensors that had been cleaned according to the manufacturer recommendations.

QCM-D measurements were conducted in an E4 instrument (Q-Sense). The flow was set to 20 µl/min and the temperature was fixed at 20.0° C. The system was equilibrated with 20 mM Tris until the baseline was stabilized. The stability of the protein coatings was investigated in the same settings. After 120 minutes of protein adsorption onto hydrophobic surfaces and 60 minutes of rinsing with 20 mM Tris, the sensors were exhibited to Phosphate Buffered Saline (PBS), as well as 0.1 and 0.5 M sodium hydroxide, 0.1 and 0.5 M hydrochloric acid, or 20% and 70% ethanol. Each solution was flown over the sensors for 30 minutes, directly followed by 30 minutes of 20 mM Tris rinsing to regain the Tris baseline for evaluation of net frequency changes corresponding to changes in protein amounts on the surfaces.

Ellipsometry

Ellipsometry monitors changes in polarization of light that is reflected on the surface. As proteins adsorb onto the surface, the light polarization is changed. By monitoring this, changes in refractive index and adsorbed mass can be calculated. Alkyl thiol functionalized gold sensors were mounted in a Q-Sense Ellipsometry module to allow simultaneous data collection using an E1 instrument (Q-sense AB) for QCM-D monitoring and an ellipsometer (Physics Instruments) to record changes in dielectric properties of the protein coatings during adsorption.

For the ellipsometry, a 532 nm laser was used at an angle of incidence of 65°. The same settings were used as for measurements in the E4 instrument, except for the flow rate, which was set to 25 µl/min. The QTools software (Biolin Scientific) was used to calculate the mass adsorption from the frequency and dissipation shifts. With this technique, water that is incorporated into the coatings is contributing to the signals so that the mass obtained with these calculations is the wet mass. The dry mass was calculated from the ellipsometry data using the Ellipsometry software (Plamen Petrov) and a 3-layer model.

Surface Plasmon Resonance

In Surface Plasmon Resonance (SPR), the angle of incidence upon which plasmon resonance occurs in a thin gold layer on the crystal chip is registered. As molecules interact with the chip surface, this angle is changed, which correlates to changes in refractive index and it thereby indirectly correlates to mass changes close to the chip surface.

PROTEON™ GLM sensor chips were demounted from their holders and cleaned as described above for QCM-D gold sensors. The PROTEON™ XPR36 Protein Interaction Array System (Bio-Rad) was used with the temperature set to 25.0° C. for both the chip and the rack, and the flow rate was set to 25 µl/min. The maximum injection volume was used, leading to 960 s of protein injection at the given flow rate. Three protein injections were performed. After each injection, 20 mM Tris buffer was flown over the chip during the automated syringe refill periods.

Atomic Force Microscopy

After QCM-D analyses, sensors with adsorbed proteins were used for Atomic Force Microscopy imaging, in which the surface topography is determined by measuring the deflection changes of a tip in close proximity to the surface that is scanning selected areas on the sample. Protein coatings were imaged in 20 mM Tris buffer using PeakForce Tapping mode in a Bruker Dimension FastScan instrument. ScanAsyst Fluid+tips were used.

Cell Culture and Cell Seeding on Silk Coatings

Primary endothelial cells from small vessels of human origin (Human dermal microvascular endothelial cells, HDMECs, Promocell) were cultured in Endothelial cell growth medium MV2 (Promocell) containing 5% FBS. Human primary dermal fibroblasts (HDFn, ECACC, UK) were cultured in DMEM F12 ham supplemented with 5% FBS and 1% penicillin/streptomycin. The cells were seeded at 5000/cm$^2$ onto silk coatings in 96 well plates (Sarstedt Tc suspension cells).

Live/Dead Staining

At day 2 and 8, cells were washed in PBS and stained for 30 minutes with Calcein-AM and EthD-1 (Live/dead Viability kit, Molecular probes) in medium for live and dead cells respectively. Micrographs were taken at 10× magnification in an inverted fluorescence microscope (Nikon TSi-u).

ALAMAR BLUE® Viability Assay

Cell viability at day 0, 3, 8 and 11 was analysed with ALAMAR BLUE® viability assay diluted 1:10 in culture medium for 2 h. Fluorescence intensity of the supernatants was measured in a ClarioStar plate reader at excitation/emission 540/595. Medium without cells was used as blank, which was subtracted from the values. Wells were run in triplicates.

Example 1

Real-Time Monitoring of Silk Coating Formation Reveals Continuous Adsorption

The recombinant spider silk protein RepCT (SEQ ID NO: 2) is flown over gold surfaces using a QCM-D sensor and a SPR sensor, respectively. FIG. 1 shows protein adsorption onto alkylthiol-modified gold sensors. Adsorption of 0.1 g L$^{-1}$ RepCT studied by QCM-D (A) and SPR (B), and 0.1 g L$^{-1}$ Protease 3C studied by QCM-D (C) and SPR (D) are shown. I, III, and V indicate the start of a protein flow over the surfaces, while at time points II and IV, the surfaces are rinsed with buffer.

When RepCT is flown over a QCM-D sensor, it adsorbs onto the surface in two distinct phases (FIG. 1A). During the very first minutes, protein-surface interactions leads to a fast frequency shift of −23 Hz (n=6, σ=4) and the formation of a surface layer. Curiously, the adsorption does not stagnate when the surface has been covered with the initial surface layer of protein. Instead, the bulk proteins interact with the surface adsorbed proteins to build thicker coatings through protein-protein interactions. This process continues as long as there are proteins present in the bulk. We interpret this as silk assembly, i.e. the formation of an assembled silk structure layer onto the initial surface layer. When the protein solution is exchanged for a buffer solution to rinse the surface, the frequency and dissipation of the sensor stays unchanged, which means that the adsorbed mass and the viscoelastic properties of the coating are maintained. Thus, no proteins are washed away during buffer flow, indicating that the protein-protein interactions are stable.

The same experiment was conducted using the non-silk protein Protease 3C, which is similar to RepCT in size (24 kDa and 23 kDa respectively) and major secondary structure motifs (55% β-sheets in a PDB-sequence similar to the Protease 3C herein, and 30-60% β-sheets in RepCT in silk form as predicted from the percentage of regions prone to beta-sheet formation). After the initial minutes of Protease 3C adsorption, driven by protein-to-surface interactions, no more adsorption occurs, since these proteins cannot self-assemble (FIG. 1C).

The same adsorption patterns were seen in SPR analyses with RepCT and Protease 3C. Here, the syringe volume limited the adsorption time to 15 minutes for each injection. In order to study adsorption after longer time periods, three protein injections were performed (phase I, III, and V in FIGS. 1B and D) with buffer rinse in between (phase II and IV in FIGS. 1B and D). As was seen with QCM-D, adsorption of Protease 3C reaches a saturation whereas the adsorption of RepCT continuous as soon as proteins are available in the bulk solution. These experiments clearly show that silk assembly occurs upon adsorption onto surfaces, as the continuous adsorption behavior is distinct from the saturating adsorption of a non-assembling protein.

Example 2

Concentration Dependence of the Assembly Process

The concentration dependence of the assembly process of the recombinant spider silk protein RepCT (SEQ ID NO: 2) was studied using QCM-D by flowing increasing protein concentrations over gold surfaces.

Figure 2:
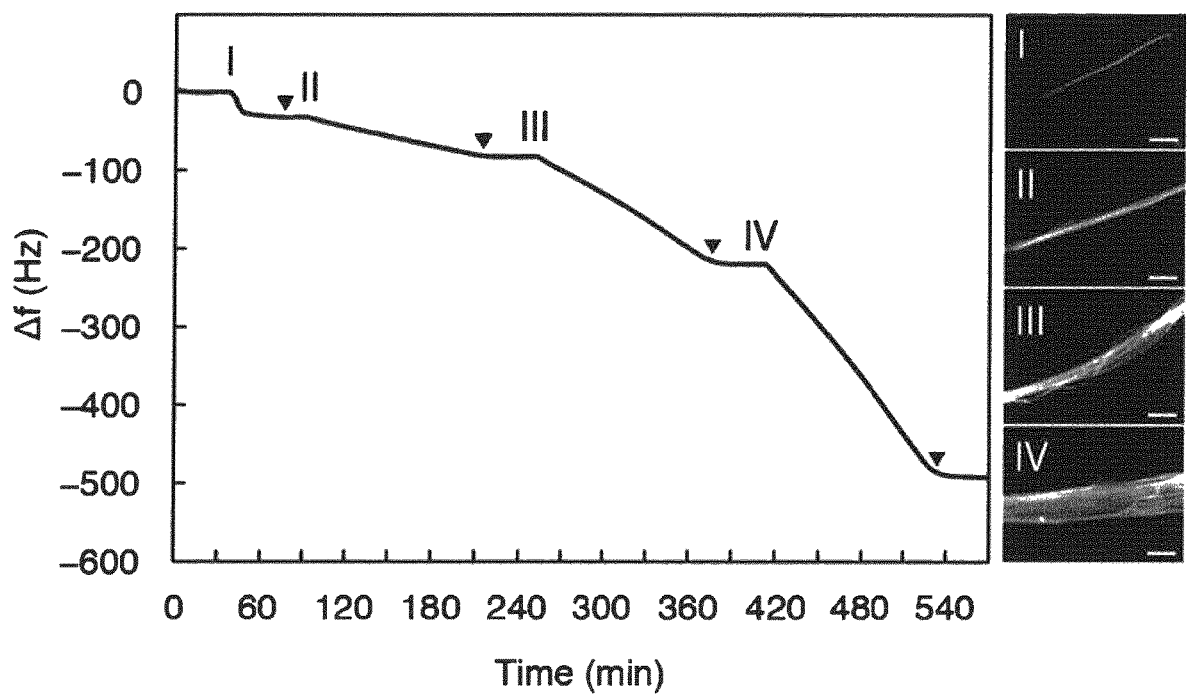
FIG. 2 shows a QCM-D measurement of adsorption of various concentrations of the recombinant spider silk protein.

FIG. 2, left panel, shows QCM-D measurement of RepCT adsorption onto hydrophobic alkyl thiolyzed gold sensors. At each arrow, buffer is flown over the surface for 30 min. Protein concentration is increased at each numbered mark: I) 0.05 mg/ml, II) 0.1 mg/ml, III) 0.3 mg/ml, and IV) 0.5 mg/ml. Images to the right are light microscope photographs of silk fibers of the same concentrations. The scale bar is 1.0 mm.

Increasing the concentration of RepCT from 0.05 to 0.1, 0.3, and finally 0.5 mg/ml during adsorption leads to faster adsorption in the assembly phase for each increase in concentration without saturating the surface (FIG. 2). This proves once again that the observed adsorption patterns are due to the self-assembling nature of RepCT proteins. The same concentration dependence is seen for fiber formation from protein solution of corresponding concentrations (FIG. 2).

Example 3

Self-Assembled Silk Coatings are Water-Rich

Viscoelastic properties of the adsorbed layer can be derived from QCM-D measurements using the dissipation (D) to frequency (f) ratio. The formation of a rigid layer gives a low D-value and thus a low $\Delta D/\Delta f$, whereas formation of a viscous layer results in a high $\Delta D/\Delta f$. For the recombinant spider silk protein RepCT (SEQ ID NO: 2), the initial adsorption phase results in a $\Delta D/\Delta f$ of 0.014 (n=6, σ=0.017) and during the assembly phase, $\Delta D/\Delta f$ is 0.118 (n=6, σ=0.017). Thus, the initial surface layer is rigid, and the continuous silk assembly results in a more viscous layer, the assembled silk structure layer.

This viscoelastic properties of the silk coatings are visualized in FIG. 3 by plotting the dissipation against the frequency shifts. In FIG. 3A, the change in dissipation during adsorption to QCM-D sensors is plotted against the corresponding frequency change for RepCT (black, long curve) and Protease 3C (triplicates shown, shorter grey curves), both proteins were used in 20 mM Tris buffer. In FIG. 3B, the water content (dotted line) of RepCT coatings were determined by calculation of the wet mass from QCM-D measurements (solid line) and the dry mass from simultaneous ellipsometry measurement (dashed line).

At frequencies close to zero, i.e. in the beginning of the coating formation, the dissipation change is much slower than the frequency change. At a certain point, the slope of the curve adopts a higher value, which remains the rest of the measurement, leading to high dissipation and frequency values. This behavior should be compared to the dissipation-frequency plot of Protease 3C adsorption (FIG. 3A, the three lower curves correspond to triplicates of Protease 3C adsorption measurements). These proteins cannot self-assemble into continuous coatings as RepCT can. Thus, these curves never reach frequencies below −30 Hz. The slopes are constantly low during the main part of the experiment, implying formation of a rigid protein layer. After reaching a frequency minimum, the slope is reversed as a result of the buffer rinse. This is interpreted as a removal of a few loosely bound proteins, at the same time decreasing the viscoelasticity slightly.

By comparing the adsorbed masses as calculated from QCM-D and ellipsometry data that was obtained from simultaneous measurements on the same surfaces, the mass with and without water can be extracted, respectively, and the water content in the protein coating can be determined (FIG. 3B). The water content of Protease 3C layers is 40% (n=3, σ=10) whereas RepCT coatings have a water content as high as 77% (n=3, σ=11), in accordance with its fairly high D/f-values.

Example 4

Silk Assembles into Fibrillar Structures

The structure of coatings of the recombinant spider silk protein RepCT (SEQ ID NO: 2) was visualized with microscopy. Alkyl thiolyzed gold sensors were imaged with Atomic Force Microscopy after adsorption during QCM-D measurements.

Figure 4:
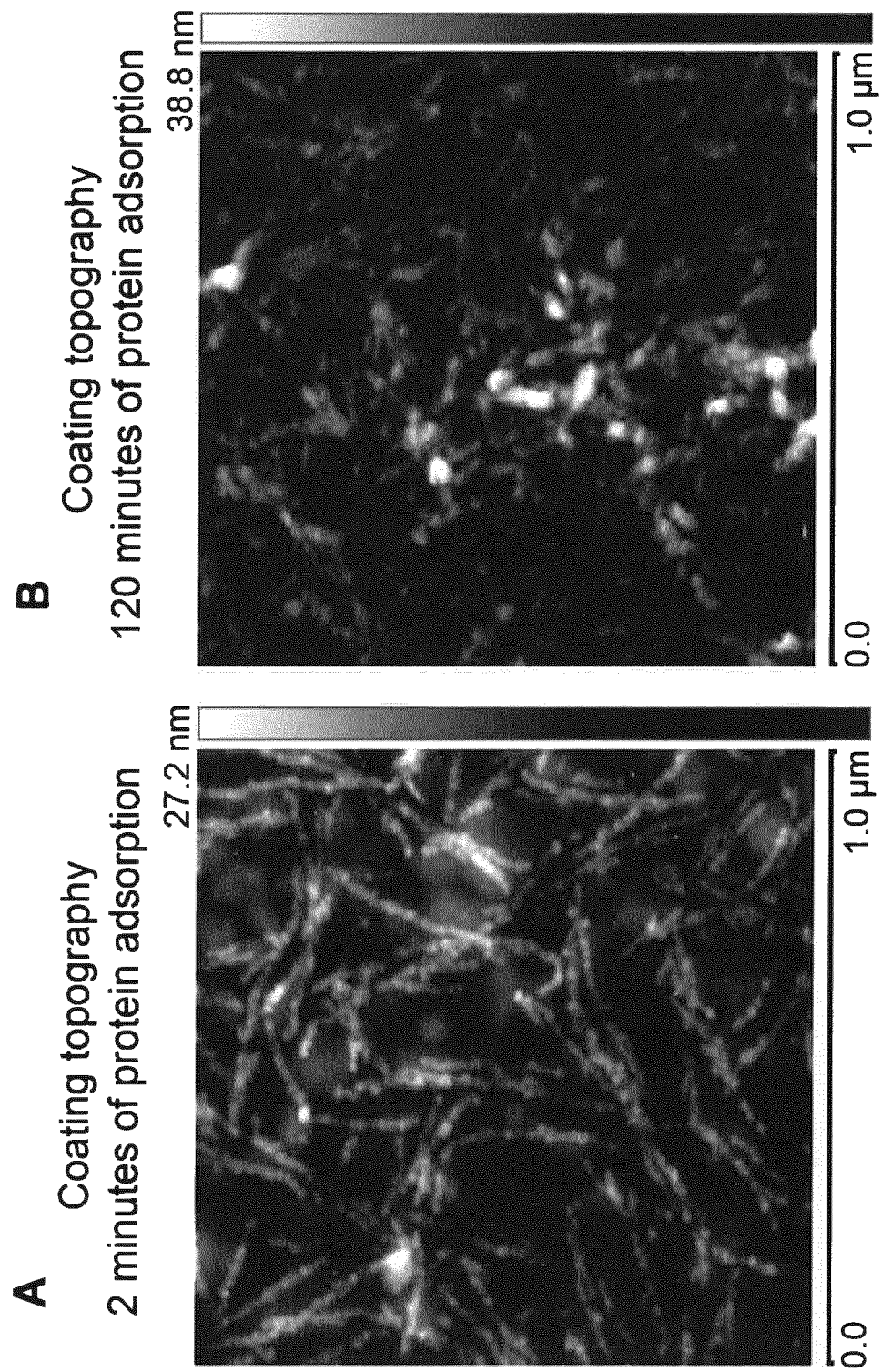
FIG. 4 shows topographic images of nanofibrils of the recombinant spider silk protein coatings according to the invention.

FIG. 4 shows topographic images of RepCT proteins after 2 minutes adsorption (A) and 120 minutes adsorption (B) on alkyl thiol functionalized gold QCM-D sensors, obtained by AFM in Tris buffer. Interestingly, we found that the proteins do not adsorb as homogenous layers but as nanofibrils (FIG. 4). The nanofibrils are 10-20 nm wide and stack into strings, seemingly like rows of pearls, at various lengths ranging from 70-400 nm.

Example 5

Coatings are Stable Towards Chemical Wash

The coating stability of coatings of the recombinant spider silk protein RepCT (SEQ ID NO: 2) was evaluated during QCM-D measurement by flowing PBS, 0.1 and 0.5 M HCl, 0.1 and 0.5 M NaOH, as well as 20% and 70% ethanol over the coatings. In between each of these washings, Tris buffer was flown over the surfaces to distinguish between buffer bulk effects from actual changes of the coatings. Any net shift to higher frequencies after changing back to Tris buffer would indicate that proteins have been washed away.

Figure 5:
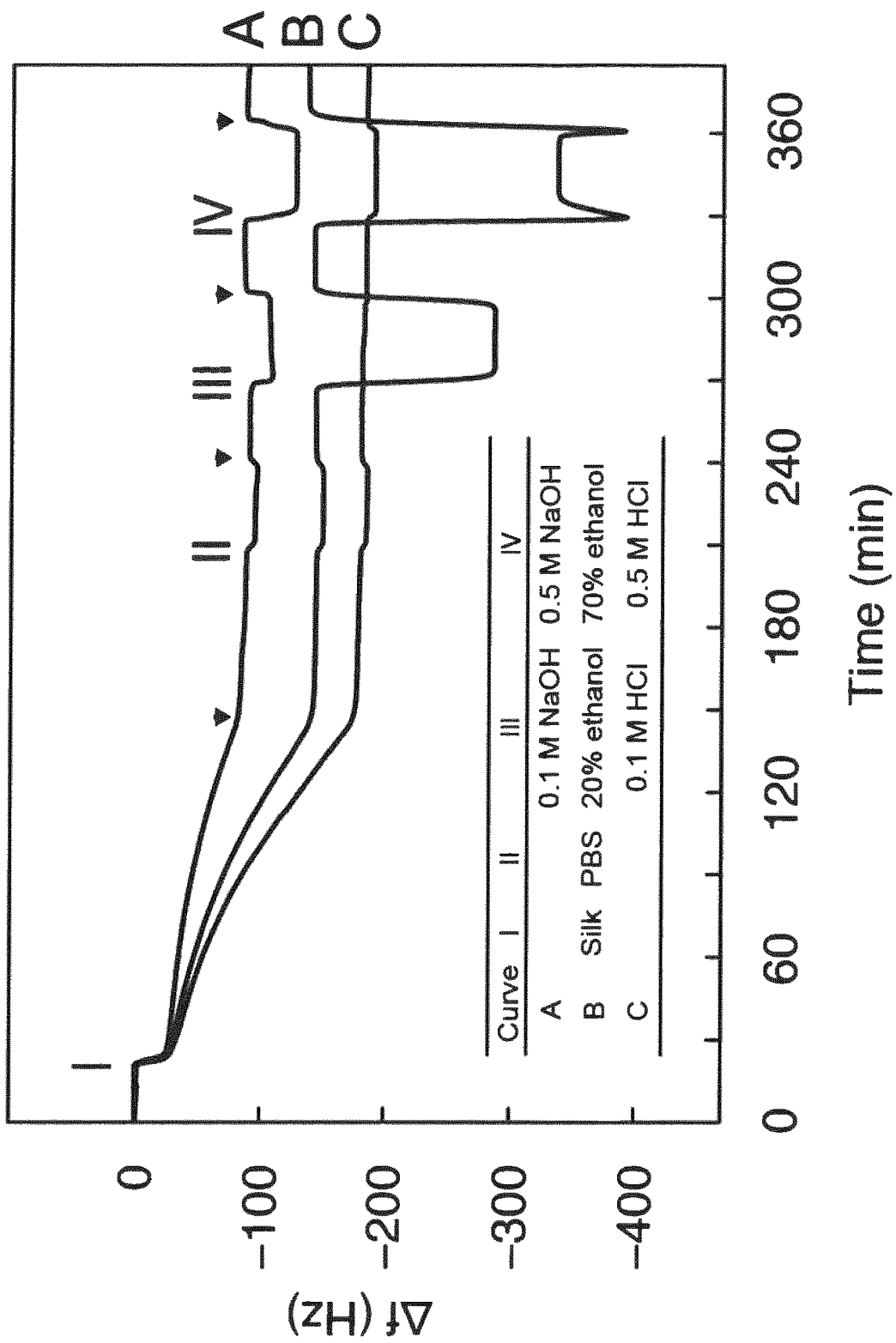
FIG. 5 shows chemical wash stability of spider silk protein coatings according to the invention.

FIG. 5 shows a QCM-D analysis of RepCT assembly on hydrophobic surfaces, subsequently followed by rinsing with solutions as stated in the figure table. Arrows show when rinsing solutions were changed to Tris buffer. As is evident in FIG. 5, no mass loss occurred after any of the washing steps, which means that the silk coatings are stable towards all tested solutions.

Example 6

Easy and Chemical-Free Functionalization of Implant Surfaces

Recombinant spider silk proteins fused with the antimicrobial peptide Magainin I (MAG-RepCT; SEQ ID NO: 9) and a fibronectin motif ($FN_{cc}$-RepCT; SEQ ID NO: 11), respectively, was used to evaluate the possibility to functionalize clinically relevant implant materials. Adsorption of each silk type was studied in real-time by QCM-D while flowing them over polystyrene, titanium and stainless steel coated sensors. Both silk types could adsorb well onto all surfaces without any pre-treatments.

FIG. 6 shows a QCM-D study of silk assembly onto titanium (solid line) and stainless steel (dashed line) with $FN_{cc}$-RepCT (A) and MAG-RepCT (B). The assembling ability was retained for both MAG-silk and $FN_{cc}$-silk, resulting in equally good coating formation on surfaces of functional silk as non-functional silk.

This opens up for easy, non-covalent functionalization of clinically relevant implant materials, where peptide motifs that can improve implant performances in vivo can be immobilized on the implant surfaces without any need for chemical attachment.

The QCM-D technology was further used to investigate the potential to coat other surfaces constituting different chemical and physical properties with various types of (MAG-RepCT, $FN_{cc}$-RepCT and Z-RepCT) Z-RepCT (SEQ ID NO: 13) is a recombinant spider silk protein fused with a Z domain, i.e. an engineered analogue of the IgG-binding domain B of protein A from *Staphylococcus aureus*. A summary of the results is presented in Table 2.

TABLE 2

Substrates for silk coatings through self-assembly

| Surface | Properties | Silk type | Initial adsorption | Assembly adsorption |
|---|---|---|---|---|
| Titanium | Metal, hydrophilic | FN-RepCT, MAG-RepCT | Yes | Yes |
| Stainless steel | Metal alloy, hydrophilic | FN-RepCT, MAG-RepCT | Yes | Yes |
| Polystyrene | Polymer, hydrophobic | FN-RepCT, MAG-RepCT | Yes | Yes |
| Hydroxyapatite | Mineral, bone-like | RepCT | Yes | Yes |
| Silicon dioxide | Glass-like | RepCT, Z-RepCT | Yes | Yes |
| APTES-func. silicon dioxide | Aminosilane | Z-RepCT | Yes | Yes |
| Gold | Metal | RepCT | Yes | Yes |
| Alkyl thiol-func. gold, θ > 30° | Hydrocarbon, Medium/high hydrophobicity | RepCT | Yes | Yes |
| Alkyl thiol-func. gold, θ < 30° | Hydrocarbon, hydrophilic | RepCT | Partly | No |

Example 7

Functional Coatings Enhance Cell Interactions with Implant Surfaces

In order to evaluate the cell compatibility of the recombinant spider silk coatings according to the invention, human fibroblasts and endothelial cells of dermal origin were allowed to grow on the coatings for 11 days, during which growth was monitored by ALAMAR BLUE® viability assay (FIGS. 7A and B). After 2 and 8 days, the cells were stained to investigate the presence of live and dead cells, but also to visualize cell morphology and cell spreading on the matrices (green staining) (FIGS. 7C and D).

FIG. 7 illustrate cell viability on silk coatings of $FN_{cc}$-RepCT (SEQ ID NO: 9) and MAG-RepCT (SEQ ID NO: 11) on polystyrene. The cell counts are shown for HDF (A) and HDMEC (B). Live/dead images at day 2 (d2) and day 8 (d8) of HDF (C) and HDMEC (D) on each silk type is shown to the right.

The results indicate that both cell types survive and proliferate on the silk coatings. On MAG silk, the fibroblasts show a growth curve very similar to the RepCT silk (SEQ ID NO: 2), i.e. recombinant spider silk according to the invention without any specific function added to it, whereas endothelial cells show a slightly increased growth on MAG-RepCT silk compared to RepCT silk.

The Live/dead staining showed high levels of viable cells, and only occasional dead cells for both coatings. Fibroblasts appeared with normal morphology and spreading on both FN silk and MAG silk. The endothelial cells had a slightly poor spreading at day 2, though improving during the culture period and the cells showed normal morphology at day 8, though not as high confluence as on FN silk. The results suggest that the silk coatings are able to enhance interaction with cells and to support their growth and survival on the coated surface.

Example 8

Coating Formation of Affinity Silk Fusions

Three different silk fusions with affinity domains; Z-RepCT, C2-RepCT and ABD-RepCT was separately flown over gold surfaces using a QCM-D sensor. Z-RepCT (SEQ ID NO: 13; FIG. 8A) is a recombinant spider silk protein fused with a Z domain, i.e. an engineered analogue of the IgG-binding domain B of protein A from *Staphylococcus aureus*. C2-RepCT (SEQ ID NO: 15; FIG. 8B) is a recombinant spider silk protein fused with a C2, derived from the $F_c$ binding domain B1 of Staphylococcal Protein G. ABD-RepCT (SEQ ID NO: 17; FIG. 8C) is a recombinant spider silk protein fused with a albumin binding domain derived from Staphylococcal Protein G.

FIGS. 8A-C shows typical adsorption behavior of 0.1 mg/ml silk fusion protein in 20 mM Tris. At time point I the surfaces are exposed to protein solution, and at time point II the surfaces are rinsed with buffer. During the very first minutes, protein-surface interactions lead to a fast frequency shift due to the formation of a surface layer. Thereafter, the bulk proteins interact with the surface adsorbed proteins to build thicker coatings through protein-protein interactions, see by a continuing slope frequency shift. This process continues as long as there are proteins present in the bulk, but then the frequency stabilizes when the surfaces are rinsed with buffer.

In order to confirm maintained affinity of the Z-RepCT coating (SEQ ID NO: 13; FIG. 8D), a SiO$_2$ surface was first coated with a Z-RepCT solution (I), washed with Tris (II) and thereafter exposed to IgG (III), to display binding functionality of the exposed Z moiety. The bound IgG was retained in the presence of Tris buffer (IV). The functional coating was finally regenerated with HCl (V) to remove the bound IgG.

Example 9

Coating Formation of Growth Factor Silk Fusions

Figure 9:
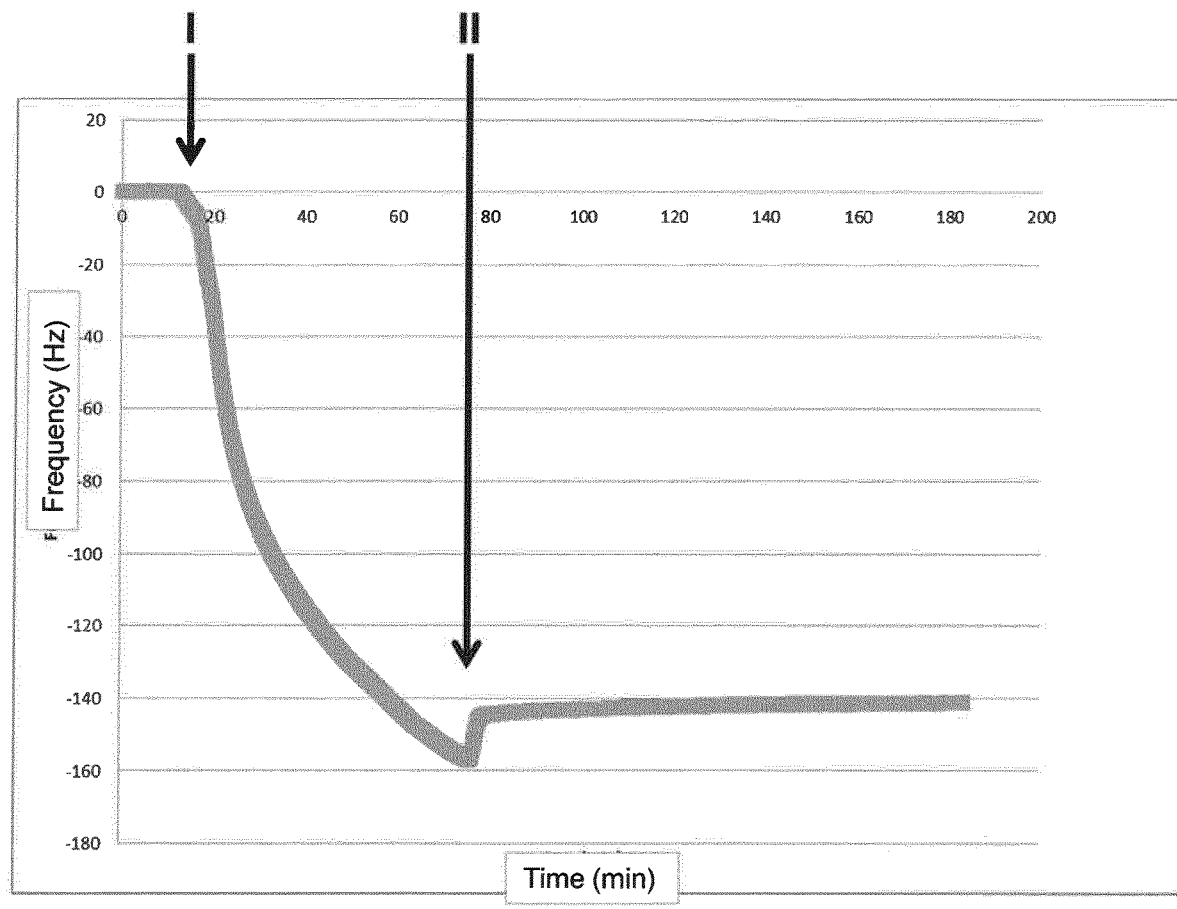
FIG. 9 shows adsorption behavior of functionalized spider silk protein onto gold surfaces.

Two different silk fusions with growth factors; RepCT-FGF (SEQ ID NO: 19) and IGF1-RepCT (SEQ ID NO: 21), were separately flown over gold surfaces using a QCM-D sensor. FIG. 9 shows typical adsorption behavior of 0.1 mg/ml RepCT-FGF in 20 mM Tris. At time point I the surfaces are exposed to RepCT-FGF protein solution, and at time point II the surfaces are rinsed with Tris buffer.

During the very first minutes, protein-surface interactions lead to a fast frequency shift due to the formation of a surface layer. Thereafter, the bulk proteins interact with the surface adsorbed proteins to build thicker coatings through protein-protein interactions, seen by a continuing slope frequency shift. This process continues as long as there are proteins present in the bulk, but then the frequency stabilizes when the surfaces are rinsed with buffer.

In order to confirm functional growth factors within the coatings, endothelial cells were cultured on silk coatings formed on polystyrene wells in defined cell culture media with or without supplemented soluble growth factors. The ability of the cells to adhere and spread out on the coatings was analyzed using a Quick adhesion assay. The proliferative behavior was analyzed using repeated ALAMAR BLUE® viability assay over one week of culture. These assays confirmed that the growth factors within the coatings were functional.

Example 10

Coating Formation of Antimicrobial Silk Fusions

Two different silk fusions with antimicrobial sequences; DspB-RepCT (SEQ ID NO: 23; including the enzyme Dispersin B which hydrolyzes glycoside in biofilms) and WGR-RepCT (SEQ ID NO: 25; including an engineered antimicrobial peptide) are flown over gold surfaces and analyzed using a QCM-D sensor, in order to verify protein adsorption and protein-protein interaction.

In order to investigate the antimicrobial effect, two types of bacteria (*Staphylococcus aureus* and *Pseudomonas aeruginosa*) are incubated onto coated surfaces, and thereafter subjected to live/dead staining and analysis with confocal microscopy to determine the ratio of viable bacteria.

Example 11

Coating Formation of Antibody Fragment Silk Fusions

Silk in fusion with recombinant antibody fragments from scFv libraries are flown over gold surfaces and analyzed using a QCM-D sensor, in order to verify protein adsorption and protein-protein interaction.

In order to verify their ability to bind its target antigen, a fluorofor labeled antigen is added to the coated surface, followed by extensive washing and analysis with fluorescence microscopy and image analysis.

Example 12

Coating Formation of Enzyme Silk Fusions

Silk in fusion with the enzyme Xylanase (Xyl-RepCT; SEQ ID NO: 27) were flown over gold surfaces and analyzed using a QCM-D sensor, which verified protein adsorption and protein-protein interaction.

Enzymatic activity in the coatings was verified using a colorimetric assay for cleavage of xylane. Briefly, 40 mM PNX (p-nitrophenyl-xylopyranoside) substrate was added, followed by incubation, e.g. 50° C. for 10 min to overnight. Then, 100 µl of stop solution (0.5 M Na$_2$CO$_3$) was added to each film, followed by absorbance measurements at 410 nm to identify the product from the enzymatic reaction.

Example 13

Coating Formation of Streptavidin Silk Fusions

Silk in fusion with a monomeric streptavidin (M4-RepCT; SEQ ID NO: 29) is flown over gold surfaces and analyzed using a QCM-D sensor, in order to verify protein adsorption and protein-protein interaction.

In order to verify binding of biotinylated molecules, the coatings are incubated with a solution containing Atto-565-biotin. After extensive washings, the coatings are subjected to fluorescence microscope analysis using an inverted Nikon Eclipse Ti instrument (excitation at 563 nm, emission at 592 nm) to investigate presence of bound labeled biotin.

TABLE 3

Fusion proteins for silk coatings through self-assembly

| Surface | Silk type | Initial adsorption | Assembly adsorption | Effect of added moiety |
|---|---|---|---|---|
| Silicon dioxide | Z-RepCT | Yes | Yes | IgG binding |
| Alkyl thiol-func. gold, θ > 30° | ABD-RepCT | Yes | Yes | Albumin binding |
| Alkyl thiol-func. gold, θ > 30° | C2-RepCT | Yes | Yes | IgG binding |
| Alkyl thiol-func. gold, θ > 30° | RepCT-FGF | Yes | Yes | Cell binding & proliferation |
| Alkyl thiol-func. gold, θ > 30° | IGF1-RepCT | Yes | Yes | Cell binding & proliferation |
| Alkyl thiol-func. gold, θ > 30° | DspB-RepCT | Yes | Yes | Antibacterial effect |
| Alkyl thiol-func. gold, θ > 30° | WGR-RepCT | Yes | Yes | Antibacterial effect |
| Alkyl thiol-func. gold, θ > 30° | scFV-RepCT | Yes | Yes | Antigen binding |
| Alkyl thiol-func. gold, θ > 30° | Xyl-RepCT | Yes | Yes | Activity (cleavage of xylans) |
| Alkyl thiol-func. gold, θ > 30° | M4-RepCT | Yes | Yes | Streptavidin binding |

Example 14

Coating Formations of Silk Fused to a Cell Binding Motif

Coatings for cell cultures were prepared by incubation of sterile filtered FN$_{cc}$-RepCT(MiSp)-silk proteins (SEQ ID NO: 70) (0.3 g L$^{-1}$) in 96 well non-treated plates (Sarstedt) for 0.5 hours. The liquid was removed and the wells were washed twice with Tris buffer (20 mM) before set to dry overnight under sterile conditions.

Primary endothelial cells from capillaries of human origin (HUVEC, PromoCell) were cultured in Endothelial cell growth medium MV2 (PromoCell) containing fetal bovine serum (FBS, 5%). The cells were used at passage 6 and seeded at 5000/well onto silk coatings in 96 well plates, with uncoated wells as controls. Cells were cultured at 37° C. with controlled levels of $CO_2$ (5%) and humidity (95%).

Cell viability at day 1, 4, and 7 was analyzed with ALAMAR BLUE® Cell Viability Reagent (Invitrogen) diluted 1:10 in culture medium for 2 h. Fluorescence intensity of the supernatants was measured in a CLARIOstar microplate reader (BMG LABTECH GmbH) at excitation=540 nm and emission=595 nm. ALAMAR BLUE® viability assay in medium without cells was used as blank and subtracted from the values. Wells were run in triplicates. FIG. 11 shows a graph of the growth curves, where it is clear that the coating of $FN_{cc}$-RepCT(MiSp)-silk proteins promotes adhesion and expansion of cells, while the control wells without coating does not support cell culture.

At day 9, cells were washed in PBS and stained for 30 minutes with calcein-AM and ethidium homodimer-1 (LIVE/DEAD® Viability/Cytotoxicity Kit L3224, Molecular Probes) in medium for detection of living and dead cells, respectively. Micrographs were captured at 10× magnification in an inverted fluorescence microscope (Nikon Ti-S). As can be seen in the upper micrograph in FIG. 11, the $FN_{cc}$-RepCT(MiSp)-silk coated well is covered with viable cells, and almost no dead cells (lower micrograph).

Example 15

Coating Formation of a Spidroin Lacking the C-Terminal Domain

A solution of the protein Rep (SEQ ID NO: 71), lacking any C-terminal (CT) domain, was flown over gold surfaces using a QCM-D sensor. FIG. 12A shows typical adsorption behavior of 0.3 mg/ml Rep in 20 mM Tris. After equilibration with 20 mM Tris buffer, the surfaces were exposed to protein solution. During the very first minutes, protein-surface interactions lead to a fast frequency shift due to the formation of a surface layer. Thereafter, the bulk proteins interact with the surface adsorbed proteins to build thicker coatings through protein-protein interactions, seen as a continuing slope frequency shift. This process continues as long as there are proteins present in the bulk (140 min). We interpret this as silk assembly, i.e. the formation of an assembled silk structure layer onto the initial surface layer, also for spidroins lacking the C-terminal domain. When the protein solution is exchanged for a buffer solution to rinse the surface, the frequency and dissipation of the sensor stays unchanged, which means that the adsorbed mass and the viscoelastic properties of the coating are maintained.

A surface with Rep protein adsorbed for 45 min was used for Atomic Force Microscopy imaging, in which the surface topography is determined by measuring the deflection changes of a tip in close proximity to the surface that is scanning selected areas on the sample. Protein coatings were imaged in 20 mM Tris buffer using PeakForce Tapping mode in a Bruker Dimension FastScan instrument, shown in FIG. 12B. ScanAsyst Fluid+ tips were used. A fibrillar coating can be observed, although less even than corresponding coatings of spidorins with the C-terminal domain.

Example 16

Films and Wet Coatings of Recombinant Spider Silk Proteins for Cell Culture Applications After purification, solutions of the recombinant spider silk proteins RepCT (SEQ ID NO: 2) and RGD-RepCT (SEQ ID NO: 72) were filter sterilized (0.22 µm) and concentrated by centrifugal filtration (Amicon Ultra, Millipore).

Films were prepared by casting solutions of protein concentration of 0.3 mg/ml into 96-well cell culture plates (Sarstedt, for suspension cells) and letting it dry over night at 25° C. and 30% relative humidity (rh) under sterile conditions. Wet coatings were prepared by the method according to the present invention, by covering the culture well with a protein solution of 0.3 mg/ml for 2 h before the liquid was removed. Both films and coated surfaces were washed twice with sterile 20 mM phosphate buffer, pH 7.4, and pre-incubated with complete cell culture medium for 1 h at 37° C. with 5% $CO_2$ before cell seeding.

Primary human dermal fibroblasts from juvenile foreskin (HDF) (ECACC) were cultured in DMEM F12 ham (Sigma) supplemented with 5% fetal bovine serum (Sigma) and 1% penicillin-streptomycin (VWR). Cells were expanded for 7 days after thawing, and cell viability was checked with trypan blue prior to seeding at 20.000 viable cells/cm$^2$. Cells were allowed to adhere to the films or coatings for 1 h in a cell incubator before gentle washing twice with pre-warmed phosphate buffered saline (PBS) followed by 10 min fixation with 96% Ethanol. After three washings in water, cells were stained for 30 min with 0.1% Crystal Violet in $H_2O$. Plates were dried after extensive washing in water.

Attachment and morphology of cells bound to the films were documented by taking micrographs at 2× and 10× magnification in an inverted bright field microscope. The color was then dissolved in 40 µL 20% acetic acid for 10 min, and 35 µL of the solution was transferred to a 384-well plate for optical density measurement at 595 nm (TECAN Infinite M200).

The amounts of adhered cells were comparable between film and coatings of same protein type (WT 60%, RGD 100%). However, detached pieces of the films were often observed, especially on the edges of the film. This phenomenon was never observed for the corresponding coatings, prepared by the wet coating method according to the invention.

The invention claimed is:

1. A method for coating a solid surface with a recombinant spider silk protein capable of forming polymeric, solid structures, comprising the following steps:
   a first adsorption step of exposing the solid surface to an aqueous solution of the recombinant spider silk protein until an initial surface layer of the recombinant spider silk protein adsorbed on the solid surface has been formed, without formation of covalent bonds between the recombinant spider silk protein and the solid surface;
   optionally washing the initial surface layer to remove soluble recombinant spider silk protein adjacent to the initial surface layer; and
   a second assembly step of exposing the initial surface layer of the solid surface to an aqueous solution of the recombinant spider silk protein and thereby forming an assembled silk structure layer of the recombinant spider silk protein on the initial surface layer;
   washing the assembled silk structure layer to remove soluble recombinant spider silk protein adjacent to the assembled silk structure layer;
   wherein the method does not include actively of spider silk protein between the first adsorption step and the second assembly step; wherein the recombinant spider silk protein comprises a repetitive (REP) fragment of from 70 to 300 amino acid residues and a CT fragment of from 70 to 120 amino acid residues, having at least 70% identity to SEQ ID NO: 3 or SEQ ID NO: 69.

2. The method according to claim 1, wherein the solid surface is a material that is hydrophobic.

3. The method according to claim 2, wherein the solid surface is a material selected from the group consisting of metals, metal alloys, polymers, minerals, glass and glass-like materials, aminosilanes, and hydrophobic hydrocarbons.

4. The method according to claim 3, wherein the solid surface is a material selected from the group consisting of titanium, stainless steel, polystyrene, hydroxyapatite, silicon dioxide, (3-Aminopropyl)triethoxysilane-functionalized silicon dioxide, gold, and alkyl thiol-functionalized gold.

5. The method according to claim 2, wherein the solid surface is a material that has a contact angle θ of more than 30° with water.

6. The method according to claim 5, wherein the solid surface is a material that has a pKa<7 of its exposed hydroxyl groups.

7. The method according to claim 2, wherein the solid surface is a material that has a pKa<7 of its exposed hydroxyl groups.

8. The method according to claim 1, wherein the recombinant spider silk protein is comprising a functionally exposed non-spidroin protein moiety or non-spidroin polypeptide moiety.

9. The method according to claim 1, wherein
   the REP is selected from the group consisting of L(AG)$_n$L, L(AG)$_n$AL, L(GA)$_n$L, and L(GA)$_n$GL, wherein
   n is an integer from 2 to 10;
   each individual A segment is an amino acid sequence of from 8 to 18 amino acid residues, wherein from 0 to 3 of the amino acid residues are not Ala, and the remaining amino acid residues are Ala;
   each individual G segment is an amino acid sequence of from 12 to 30 amino acid residues, wherein at least 40% of the amino acid residues are Gly; and
   each individual L segment is a linker amino acid sequence of from 0 to 3( )amino acid residues;
   and optionally a functionally exposed non-spidroin protein/polypeptide moiety.

10. The method according to claim 1, wherein the first adsorption step of exposing the solid surface to the aqueous solution of the recombinant spider silk protein is performed for less than 15 minutes.

* * * * *

UNITED STATES PATENT AND TRADEMARK OFFICE
CERTIFICATE OF CORRECTION

| | | |
|---|---|---|
| PATENT NO. | : 11,484,624 B2 | Page 1 of 1 |
| APPLICATION NO. | : 16/301819 | |
| DATED | : November 1, 2022 | |
| INVENTOR(S) | : My Hedhammar et al. | |

It is certified that error appears in the above-identified patent and that said Letters Patent is hereby corrected as shown below:

In the Claims

Column 111, Line 47; Claim 1:
Change:
"wherein the method does not include actively of spider"
To:
--wherein the method does not include actively drying-in of spider--

Signed and Sealed this
Tenth Day of October, 2023

Katherine Kelly Vidal
*Director of the United States Patent and Trademark Office*